(12) United States Patent
Paloheimo et al.

(10) Patent No.: US 12,031,168 B2
(45) Date of Patent: Jul. 9, 2024

(54) METHODS FOR CONTROLLING PROTEASE PRODUCTION

(71) Applicant: ROAL OY, Rajamäki (FI)

(72) Inventors: Marja Paloheimo, Rajamäki (FI); Susanna Mäkinen, Rajamäki (FI); Peter Punt, Zeist (NL); Kari Juntunen, Rajamäki (FI); Terhi Puranen, Rajamäki (FI); Jari Vehmaanperä, Rajamäki (FI)

(73) Assignee: ROAL OY, Rajamäki (FI)

( * ) Notice: Subject to any disclaimer, the term of this patent is extended or adjusted under 35 U.S.C. 154(b) by 0 days.

(21) Appl. No.: 17/116,353

(22) Filed: Dec. 9, 2020

(65) Prior Publication Data

US 2021/0102231 A1    Apr. 8, 2021

Related U.S. Application Data

(63) Continuation of application No. 15/552,387, filed as application No. PCT/FI2016/050108 on Feb. 19, 2016, now Pat. No. 10,883,131.

(30) Foreign Application Priority Data

Feb. 20, 2015 (FI) .................................. 20155112

(51) Int. Cl.
*C12P 21/02* (2006.01)
*C07K 14/37* (2006.01)
*C07K 16/14* (2006.01)
*C12N 9/02* (2006.01)
*C12N 9/24* (2006.01)
*C12N 9/42* (2006.01)
*C12N 9/48* (2006.01)
*C12N 15/80* (2006.01)

(52) U.S. Cl.
CPC .............. *C12P 21/02* (2013.01); *C07K 14/37* (2013.01); *C07K 16/14* (2013.01); *C12N 9/0061* (2013.01); *C12N 9/2405* (2013.01); *C12N 9/2437* (2013.01); *C12N 9/48* (2013.01); *C12N 15/80* (2013.01); *C12Y 110/03002* (2013.01); *C12Y 302/01004* (2013.01)

(58) Field of Classification Search
CPC ......... A61K 39/00; A61K 39/02; A61K 48/00
USPC ........... 424/93.2, 130.1, 139.1, 150.1, 164.1, 424/185.1, 234.1; 536/23.1, 23.7
See application file for complete search history.

(56) References Cited

FOREIGN PATENT DOCUMENTS

CA        2994320      *  6/2007
WO   WO2015/187697   * 10/2015
WO   WO 2016/132021  *  8/2016

* cited by examiner

*Primary Examiner* — Jana A Hines
(74) *Attorney, Agent, or Firm* — Ziegler IP Law Group LLC.

(57) ABSTRACT

The present description is related to the field of protein production. It introduces novel host cells with low protease activity, a novel protease regulator, its use in expression systems and protein production, and a method of producing host cells for protein production.

10 Claims, 12 Drawing Sheets

Specification includes a Sequence Listing.

```
1141  atgttccatc aaccgccgga aaagcctcgc gcgcctggct tcgacgatga tccgttcggg
       M  F  H   Q  P  P   E  K  P   R  A  P   G  F  D  D   D  P  F  G
1201  tttgtcaccc aggcctggga gagatatggc ctgggcagtg tgtcgtcgcc tccgcctgcg
       F  V  T   Q  A  W   E  R  Y   G  L  S   V  S  S   P  P  P  A
1261  atgcctccgc agcccatcca gaggaccgga cgggcctatt ccaccgcttc ggtaatggac
       M  P  P   Q  P  I   Q  R  T   G  R  A  Y   S  T  A   S  V  M  D
1321  tggacgccg agatcgatac caccttcac caccacggcg acggagtggc catgtcgccg
       W  T  P   E  I  D   T  T  F   H  H  H  G   D  G  V   A  M  S  P
1381  gtggaacacg tcgaactgga cagccttggt tcgcctcagg gagggggagg ggttggccgc
       V  E  H   V  E  L   D  S  L   G  S  P  Q   G  G  G   G  V  G  R
1441  ttggtcgcgc actttgagaa taaaggctat gtcccgccat gcctccgcg gccatcaac
       L  V  A   H  F  E   N  K  G   Y  V  P  P   L  P  P   R  P  I  N
1501  aatcagccgc atcaaccgca tcacatgggc cacagtcctt caatgtcgtc gcagtttggc
       N  Q  P   H  Q  P   H  H  M   G  H  S  P   S  M  S   S  Q  F  G
1561  agtctaaact ctgtagccca tacgcatagg atatcgagtc ccgttgctag cccaggtgaa
       S  L  N   S  V  A   H  T  H   R  I  S  S   P  V  A   S  P  G  E
1621  tcccaatatg gctcgctcgg ggtgcattcg cccccaacac ccacctcaat cgtcaccaac
       S  Q  Y   G  S  L   G  V  H   S  P  P  T   P  T  S   I  V  T  N
1681  atgaaccgct ccggcagtat aagctatggc agcttccatg acactcagca ggtgcatagt
       M  N  R   S  G  S   I  S  Y   G  S  F  H   D  T  Q   Q  V  H  S
1741  cccggtattg gtacgccttt tgggagcatg gatggcttta tgagttctgc ccgcgtgaac
       P  G  I   G  T  P   F  G  S   M  D  G  F   M  S  S   A  R  V  N
1801  agccgatgg tggcgacacc aatggcatcg acgccatga tgcccagtcc catggccgct
       S  P  M   V  A  T   P  M  A   S  T  P  M   M  P  S   P  M  A  A
1861  ccggagtgc ctggtacccc tggattcgag atttggcgac ctcctcccctc gatgactcca
       P  G  V   P  G  T   P  G  F   E  I  W  R   P  P  P   S  M  T  P
1921  aaacctgaac cctctcaaat caccaaccca gccaatttcg gcggctattt cagacctcca
       K  P  E   P  S  Q   I  T  N   P  A  N  F   G  G  Y   F  R  P  P
1981  gtgccgacga ctcccaagcc ggtagtcaac acaggtaatc agttcatctt ggaattcaac
       V  P  T   T  P  K   P  V  V   N  T  G  N   Q  F  I   L  E  F  N
2041  cccagcgcca aggcagccaa agggaaagct ccggcaaagc ctccaggcc tcgattgcct
       P  S  A   K  A  A   K  G  K   A  P  A  K   P  P  R   P  R  L  P
2101  cctcggaaac ccaaccttc acaatcacaa ctctcggcac aaacaccagc agcacctgtg
       P  R  K   P  N  L   S  Q  S   Q  L  S  A   Q  T  P   A  A  P  V
2161  caagcgtcgg tttcaacacc ggcaccggca tcggcaccga caccgacacc agccgttgcc
       Q  A  S   V  S  T   P  A  P   A  S  P  T   P  T  P   A  V  A
2221  tcaactccag gtccaatgtc tcctcctcct aaaccgcctc gcccttcaga accgtcttct
       S  T  P   G  P  M   S  P  P   P  K  P  P   R  P  S   E  P  S  S
2281  tcatccacac ccattgttgt gagcaatgcc gctaaaccaa gagaatcctt gcagctaggt
       S  S  T   P  I  V
2341  gtactaacgc gcatgtctag gcacagcggc gggattcgat ggctcttcgt gcccaggcag
                                    A  Q  R   R  D  S   M  A  L  R   A  Q  A
2401  gtactaggcc gtcacgggaa caggttcctg cagaggcctg ggagcaatac aaatccacta
       G  T  R   P  S  R  E   Q  V  P   A  E  A   W  E  Q  Y   K  S  T
2461  tccgtaccct ctatctcgag gagagaaaac ccttgaaaga agtcatgagt gtcatggctg
       I  R  T   L  Y  L  E   E  R  K   P  L  K   E  V  M  S   V  M  A
2521  aacaatatgg gtttcaagca acgtgagtcg aagattgatt cctcttctgc ttcatcgttc
       E  Q  Y   G  F  Q  A
2581  gggttcttgg ttcgttgtaa actaattcga cgcccttcct aggccaaaga tgtataaaac
                                                                    T  P  K  M  Y  K
2641  aaggttctct caatggggtt ttgtgaagaa taacacggag gaagaagtga aacggctgtt
       T  R  F  S   Q  W  G   F  V  K   N  N  T  E   E  E  V  K  R  L
```

SEQ ID NO: 11         Fig. 3

```
2701  gtcgatgaag ttccagcgag atgccgaggg caaagtttcc gagtttgttc gaaacggcag
      L  S  M  K  F  Q  R  D  A  E  G  K  V  S  E  F  V  R  N  G
2761  ggtggtgaac ctaggtacct atttgaaacg gaaaggagtg acggagtatg acctcgttga
      R  V  V  N  L  G  T  Y  L  K  R  K  G  V  T  E  Y  D  L  V
2821  tttcgaacta ccggccgacc ttccagcaca tatccgatgc agaacaccga caccacctcc
      D  F  E  L  P  A  D  L  P  A  H  I  R  C  R  T  P  T  P  P
2881  ggctctgcga tcacccgatc tgctccgtgc acaggaggta gtcgttggaa atatgcgcaa
      P  A  L  R  S  P  D  L  L  R  A  Q  E  V  V  G  N  M  R
2941  ggcattccta cactgtcggc aattcgagat ggagactgag actcagattg gttggccatc
      K  A  F  L  H  C  R  Q  F  E  M  E  T  E  Q  I  G  W  P
3001  aaccatggtt tggggtgctg gatcgagtga actcctggtc gaggccaact tttacttcga
      S  T  M  V  W  G  A  G  S  S  E  L  L  V  E  A  N  F  Y  F
3061  agctcgcgac gcagatcaag gcggtgacta cctgatgcga gctttcaagc agctcgagct
      E  A  R  D  A  D  Q  G  G  D  Y  L  M  R  A  F  K  Q  L  E
3121  ggacctcaga aagctctcgc acaaggcat catggaacta atcctggta tgatcaatcg
      L  D  L  R  K  L  S  P  Q  G  I  M  E  L  I  L  G  M  I  N
3181  ggatcccggc atgatgacgg ccctttgcaa gtaccttgca gcatattcga caaccaatct
      R  D  P  G  M  M  T  A  L  C  K  Y  L  A  A  Y  S  T  T  N
3241  ggagcgaacc catcctctcc ggcaaatctt cacttgtctg tatgaagtgc aacaaaagca
      L  E  R  T  H  P  L  R  Q  I  F  T  C  L  Y  E  V  Q  Q  K
3301  tggggcgcag acgttgtctg agctcctgtg gactagcatc tcgacaattg cggaggaact
      H  G  A  Q  T  L  S  E  L  L  W  T  S  I  S  T  I  A  E  E
3361  cgaggccatc tatggacgca agcatccgta tgtggctcgc acatgggccg atcttgcgct
      L  E  A  I  Y  G  R  K  H  P  Y  V  A  R  T  W  A  D  L  A
3421  gttttacagc caggtgaacc cggaaaggct ggagaagttg gttgttgagc ttcgtgtgct
      L  F  Y  S  Q  V  N  P  E  R  L  E  K  L  V  V  E  L  R  V
3481  ccagaggcag ctcgagcaac gacatgggca ttccagtgtc gaagtggttt ccatccgata
      L  Q  R  Q  L  E  Q  R  H  G  H  S  S  V  E  V  V  S  I  R
3541  tgccattctg ctgttggtct atgcgtcgtc tccccagtcg gatgcctcga agcaagccgc
      Y  A  I  L  L  V  Y  A  S  S  P  Q  S  D  A  S  K  Q  A
3601  aaatgattat tggaacctgc tgcggaatat gaacaccatg tttcccatgc gcgactcccg
      A  N  D  Y  W  N  L  L  R  N  M  N  T  M  F  P  M  R  D  S
3661  tccgaatagt tactgctatc acagcccgct caaggtcgat ccgtggacaa agaggtgccg
      R  P  N  S  Y  C  Y  H  S  P  L  K  V  D  P  W  T  K  R  C
3721  caggcggtac gacacactcg tcaccatatt cgaggagcat gtaggcgtta gaatcaatcc
      R  R  R  Y  D  T  L  V  T  I  F  E  E  H  V  G  V  R  I  N
3781  ctatttcgaa gaggacttcc acacgaccga gcacgctcaa gaaacgcagg atgcctgggc
      P  Y  F  E  E  D  F  H  T  T  E  H  A  Q  E  T  Q  D  A  W
3841  ggcagctctg caaatgggtt cgacgaatag atcttggggc ttcatctag  3889
      A  A  A  L  Q  M  G  S  T  N  R  S  W  G  F  I  -
```

SEQ ID NO: 11

Fig. 3 (continued)

Pea1 SEQ ID NO: 13, F. Oxysporum SEQ ID NO: 22, G. Fujikuroi SEQ ID NO: 23, S. chartatum SEQ ID NO: 24, C. purpurea SEQ ID NO: 25, O. sinensis SEQ ID NO: 26, N. haematococca SEQ ID NO: 27, M. acridum SEQ ID NO: 28, V. virens SEQ ID NO: 29, A. chrysogenum SEQ ID NO: 30

```
Pea1            402  RPSREQVPAEAWEQYKSTIRTLYLEERKPLKEVMSVMAEQYGFQATPKMY
F. Oxysporum    386  RPSREQVPAEAWESFKHTIRKLYLEERKPLKEVMSVMADQYGFQATPKMY
G. Fujikuroi    386  RPSREQVPAEAWESFKHTIRKLYLEERKPLKEVMSVMADQYGFQATPKMY
S. chartarum    379  RPSREQVPAEAWEQFKTTIRSLYLEERKPLKEVMSIMADKYGFQATPKMY
C. purpurea     468  RPPREQVPAEAWEQFKGTIRTLYLEERKPLKEVMSIMAERFGFQATPKMY
O. sinensis     397  RPSREQVPAEAWEQFKSTIRALYLDERRPLKEVMNVMAEKYKFQATPKMY
N. haematococca 854  RPSREQVPAEAWESFKNTIRTLYLDERKPLKEVMSIMADKYGFQATPKMY
M. acridum      460  RPSREQVPAEAWEQFKGTIRSLYLEDRKPLKEVMAIMAEKYNFQATPKMY
V. virens       479  RPSREQVPAEAWEHFKGIIRALYLEERKPLKEVMAIMADKYSFQATPKMY
A. chrysogenum  556  RPSREQVPAEAWEGLKSTIRDLYLEQRKPLKEVMSIMAEKYNFQATPKMY
                     **  **********  *   **  ***  *  *******   ***   ********

Pea1            452  KTRFSQWGFVKNNTEEEVKRLLSMKFQRDAEGKVSEFVPNGRVVNLGTYL
F. oxysporum    436  KTRFSQWGFVKNNTEEEVKRLLSMKFQRDAEGKVSEFVRNGKVVNLGTYL
G. fujikuroi    436  KTRFSQWGFVKNNTEEEVKRLLSMKFQRDAEGKVSEFVRNGKVVNLGTYL
S. Chartarum    429  KTRFSQWGFVKNNTEDEVKRLLSMKFQRDAEGKVSEFVRNGRVVNLGTYL
C. purpurea     518  KTRFSQWGFVKNNTEEEVKRLLSKKFQRDAEGKISEFVRNGRVVNLGTYL
O. Sinensis     447  KTRFSQWGFVKNNTEDEVKRLLSMKFQRDAEGKVSEFVRNGRVVNLGTYL
N. Haematococca 904  KTRFSQWGFVKNNTEEEVKRLLSKKFQRDAEGKVSEFVRNGKVVNLGTYL
M. acridum      510  KTRFSQWGFVKNNTEEEVKKLLSMKFQRDAEGKVSEFVRNGRVVNLGTYL
V. virens       529  KTRFSQWGFVKNNTEEEVKRLLSMKFQRDAEGKVSEFVRNGRVVNLGTYL
A. chrysogenum  606  KTRFSQWGFVKNNTEDEVKKLLSMKFQRDAEGKVSEFVRNGKIVNLGTYL
                     **************:***:***  ********:******::*******

Pea1            502  KRKGVTEYDLVDFELPADLPAHIRCRTPTPPP
F. oxysporum    486  KRKGVTEYDLVDFELPADLPAHIRCRTPTPPP
G. Fujikuroi    486  KRKGVTEYDLVDFELPADLPAHIRCRTPTPPP
S. chartarum    479  KRKGVTEYDLVDFELPADLPAHIRCRTPTPPP
C. purpurea     568  KRKGVTEYDLVDFELSADLPAHVRCRTPTPPP
O. Sinensis     497  KRKGVTEYDLIDFELPADLPAHVKCRTPTPPP
N. Haematococca 954  KRKGVTEYDLIDFELPAELPAHIRCRTPTPPP
M. acridum      560  KRKGVTEYDLVDFELSADLPAHVRCRTPTPPP
V. virens       579  KRKGVTEYDLVDFELPADLPAHVRCRTPTPPP
A. Chrysogenum  656  KRKGVTEYDLVDFELPANLPSHIRCRTPTPPP
                     **********:**** *:**:*::********
```

Fig. 4 pALK4107 deletion cassette (7615 bps)

```
31UV#22     MFHQPPEKPRAPGFDDDPFGFVTQAWERYGLGSVSSPPPAMPPQPIQRTGRAYSTASVMD
31SP#4      MFHQPPEKPRAPGFDDDPFGFVTQAWERYGLGSVSSPPPAMPPQPIQRTGRAYSTASVMD
A21         MFHQPPEKPRAPGFDDDPFGFVTQAWERYGLGSVSSPPPAMPPQPIQRTGRAYSTASVMD
33SP#9      MFHQPPEKPRAPGFDDDPFGFVTQAWERYGLGSVSSPPPAMPPQPIQRTGRAYSTASVMD
pALK4106    MFHQPPEKPRAPGFDDDPFGFVTQAWERYGLGSVSSPPPAMPPQPIQRTGRAYSTASVMD

31UV#22     WTPEIDTTFHHHGDGVAMSPVEHVELDSLGSPQGGGGVGRLVAHFENKGYVPPLPPRPIN
31SP#4      WTPEIDTTFHHHGDGVAMSPVEHVELDSLGSPQGGGGVGRLVAHFENKGYVPPLPPRPIN
A21         WTPEIDTTFHHHGDGVAMSPVEHVELDSLGSPQGGGGVGRLVAHFENKGYVPPLPPRPIN
33SP#9      WTPEIDTTFHHHGDGVAMSPVEHVELDSLGSPQGGGGVGRLVAHFENKGYVPPLPPRPIN
pALK4106    WTPEIDTTFHHHGDGVAMSPVEHVELDSLGSPQGGGGVGRLVAHFENKGYVPPLPPRPIN

31UV#22     NQPHQPHHMGHSPSMSSQFGSLNSVAHTHRISSPVASPGESQYGSLGVHSPPTPTSIVTN
31SP#4      NQPHQPHHMGHSPSMSSQFGSLNSVAHTHRISSPVASPGESQYGSLGVHSPPTPTSIVTN
A21         NQPHQPHHMGHSPSMSSQFGSLNSVAHTHRISSPVASPGESQYGSLGVHSPPTPTSIVTN
33SP#9      NQPHQPHHMGHSPSMSSQFGSLNSVAHTHRISSPVASPGESQYGSLGVHSPPTPTSIVTN
pALK4106    NQPHQPHHMGHSPSMSSQFGSLNSVAHTHRISSPVASPGESQYGSLGVHSPPTPTSIVTN

31UV#22     MNRSGSISYGSFHDTQQVHSPGIGTPFGSMDGFMSSARVNSPMVATPMASTPMMPSPMAA
31SP#4      MNRSGSISYGSFHDTQQVHSPGIGTPFGSMDGFMSSARVNSPMVATPMASTPMMPSPMAA
A21         MNRSGSISYGSFHDTQQVHSPGIGTPFGSMDGFMSSARVNSPMVATPMASTPMMPSPMAA
33SP#9      MNRSGSISYGSFHDTQQVHSPGIGTPFGSMDGFMSSARVNSPMVATPMASTPMMPSPMAA
pALK4106    MNRSGSISYGSFHDTQQVHSPGIGTPFGSMDGFMSSARVNSPMVATPMASTPMMPSPMAA

31UV#22     PGVPGTPGFEIWRPPPSMTPKPEPSQITNPANFGGYFRPPVPTTPKPVVNTGNQFILEFN
31SP#4      PGVPGTPGFEIWRPPPSMTPKPEPSQITNPANFGGYFRPPVPTTPKPVVNTGNQFILEFN
A21         PGVPGTPGFEIWRPPPSMTPKPEPSQITNPANFGGYFRPPVPTTPKPVVNTGNQFILEFN
33SP#9      PGVPGTPGFEIWRPPPSMTPKPEPSQITNPANFGGYFRPPQCRRLPSR------------
pALK4106    PGVPGTPGFEIWRPPPSMTPKPEPSQITNPANFGGYFRPPVPTTPKPVVNTGNQFIL----

31UV#22     PSAKAAKGKAPAKPPRPRLPPRNPTFHNHNSRHKHQQHLCKRRFQHRHRHRHRHQPLP
31SP#4      PSAKAAKGKAPAKPPRPRLPPRKPNLSQSQLSAQTPAAPVQASVSTPAPASAPTPTPAVA
A21         PSAKAAKGKAPAKPPRP--------------------------------------------
33SP#9      ------------------------------------------------------------
pALK4106    ------------------------------------------------------------

31UV#22     QLQVQCLLLLNRLALQNRLLHPHPLLHSGGIRWLFVPRQVLGRHGNRFLQRPGSNTNPLS
31SP#4      STPGPMSPPPKPPRPSEPSSSSTPIVA---------------------------------
A21         ------------------------------------------------------------
33SP#9      ------------------------------------------------------------
pALK4106    ------------------------------------------------------------

31UV#22     VPSISRRENP
31SP#4      ----------
A21         ----------
33SP#9      ----------
pALK4106    ----------
```

Fig. 7

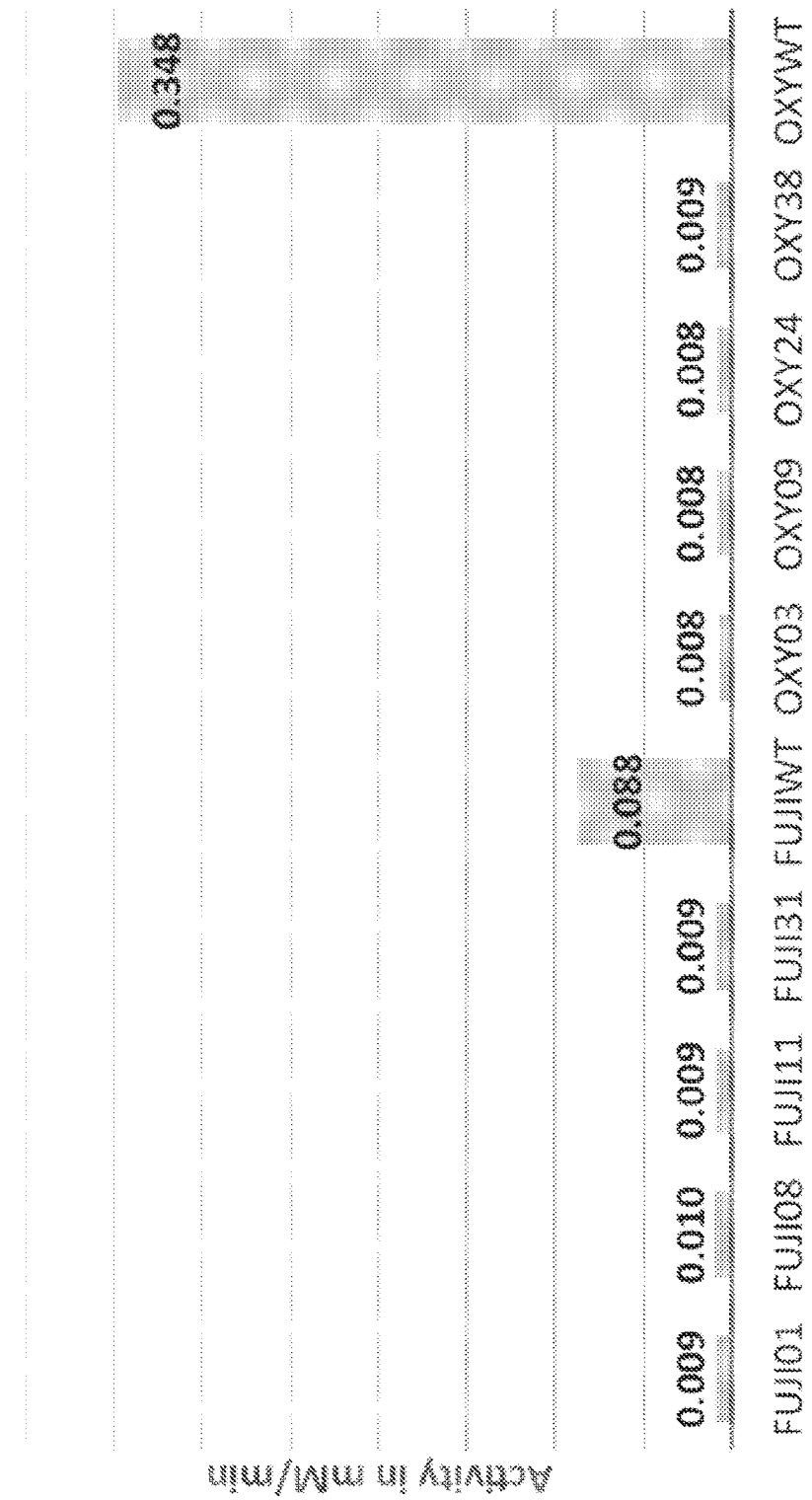

METHODS FOR CONTROLLING PROTEASE PRODUCTION

FIELD

The present description is related to the field protein production. More specifically, it discloses a novel protease expression regulator and its use in the production of proteins of interest in host cells.

BACKGROUND

Microorganisms, such as fungi and filamentous fungi, are widely used as host cells for expression and extracellular secretion of proteins of interest, such as recombinant proteins. One disadvantage frequently encountered with microorganisms, when used as host cells, is their inherent production and secretion of proteolytic enzymes that degrade the protein of interest. This problem is particularly difficult when producing proteins of interest that are sensitive, unstable, or both. Thus, endogenous proteases of the host cell at least reduce the yield of the protein of interest and may even prevent its production. Additionally, proteolytic activity of the endogenous proteases may lead into formation of fragmented or degraded proteins, which lowers the quality of proteins produced in host cells. Protein authenticity may be affected by proteolysis due to trimming of N and/or C terminal amino acids by exopeptidases. Further, the presence of endogenous proteases decreases the stability and shelf life of protein compositions when the endogenous proteases are present in the protein compositions. In case longer shelf-life or stability of protein composition is desired the endogenous proteases have to be removed from the protein composition or their protease activity has to be inhibited, e.g. by protease inhibitors.

Various solutions to circumvent the above problems have been envisaged. For example, one could delete or disrupt genes encoding the various endogenous proteases, if the proteases are properly identified and characterised. WO 90/00192 describes mutant filamentous fungal hosts which have been rendered incapable of secreting an enzymatically active aspartic protease. By such mutation, it was shown that the yield of the heterologous polypeptide, bovine chymosin, could be increased. WO2013/102674 describes filamentous fungal cells that are deficient in at least three endogenous proteases, and wherein the endogenous proteases are inactivated by a mutation at the genes encoding the endogenous proteases. Attempts have also been made to inactivate endogenous proteases by random mutagenesis, but they may lead to unknown and unwanted pleiotropic effects on fermentation performance, such as problems in gene expression and poor growth rate of the host cell. Random mutagenesis produces mutations non-specifically throughout the genome of the host cell. The mutated genes producing desirable or undesirable characteristics for the host cell cannot be easily identified. The resulting mutant strains have to be used as such, even though some of the mutations might lead to non-desired outcome regarding the characteristics of the strain and/or its products.

Another approach to prevent problems of endogenous proteases has been to optimize raw materials and cultivation conditions in such a way that endogenous protease production is reduced or prevented.

However, it is well known that fungi produce a large number of endogenous proteases. Thus, strain tailoring by individually inactivating each endogenous protease is impractical. In addition, it has been shown that disruption of one protease gene may lead to a compensatory increase in the expression and production of another proteinase gene or genes. Consequently, there is an interest to develop for industrial use strains of filamentous fungi exhibiting no, or very low levels of, proteolytic activity originating from endogenous proteases. Further, it would be advantageous to provide methods that allow preventing production of endogenous proteases in host cells. In particular *Trichoderma reesei* with low endogenous protease activity would be particularly desirable because it is a suitable host cell for many recombinant proteins.

Some enzymes are exceptionally sensitive even to low amounts of proteases and they may need further modifications to remain stable in products such as in enzyme compositions. For example many proteins having a multi domain structure wherein the domains are linked by flexible linker regions, such as cellulases with a cellulose binding moiety, may be particularly susceptible to protease cleavage. Consequently, such enzymes may be difficult to develop into products with an acceptable shelf life and they often require careful engineering of the joining sequence in addition to using a low protease host and optimization of cultivation conditions.

SUMMARY

It is an object to at least partially solve above problems of prior art. A related object is to improve production of proteins, especially such proteins which are sensitive to host proteases or are unstable when produced in a fungal expression system.

It is also an object to provide a method for regulating endogenous protease expression in micro-organisms.

Another object is to provide a protease regulator, a gene encoding it, and a vector comprising said gene.

It is another object to provide a protease regulator variant, a gene encoding it, and a vector comprising said gene.

It is another object to provide a method of producing a protein of interest in a host cell.

It is yet another object to provide an alternative polynucleotide and a polypeptide which regulates endogenous protease expression in a host cell.

The present inventors have surprisingly found that endogenous expression of several proteases can be suppressed in a host cell by inactivating a gene encoding a protease regulator named pea1 by the present inventors. Suppression of endogenous proteases by preventing action of pea1 in a host cell resulted into e.g. improved yield and stability of recombinant proteins produced in the host cell.

According to the first aspect of the invention there is provided a polynucleotide comprising a nucleotide sequence encoding a protein comprising an amino acid sequence having at least 90% sequence identity to amino acids 402-533 of SEQ ID NO: 13, wherein inactivation of a chromosomal gene comprising the polynucleotide results into suppression of production of endogenous proteases of the host cell compared to a host cell wherein the chromosomal gene comprising the polynucleotide is not inactivated.

The polynucleotide of the first aspect has been shown by the inventors to be responsible for producing a gene product which regulates expression of many fungal endogenous proteases. Thus, the gene is herein called a protease regulator, protease expression affecting 1, or pea1 and it is characterised at least by the presence of the sequence encoding the highly conserved region residues 402-533 of SEQ ID NO:13. The corresponding pea1 gene product (when a polypeptide) is herein called Pea1. Inhibiting the pea1 resulted in lowered levels of endogenous protease expression, as shown in Examples below. By repressing, down-regulating, inactivating or inhibiting pea1 expression it was shown to be possible to suppress, i.e. to down-regulate, expression of several endogenous proteases of the fungal host cell. The dramatic decrease in the endogenous protease activity resulted into lower degradation of proteins expressed by the host cell and, consequently, increased yield of proteins of interest, such as heterologous recombinant proteins produced by the host cell. A further advantage may be that less inactive or fragmented protein of interest may be produced because fewer endogenous proteases are produced and secreted. The protein of interest produced by the host cell may also be less prone to degradation which leads into improved authenticity, stability and shelf-life. Variants, fragments, and nucleotides that are hybridisable can be used e.g. to detect presence of the protease regulator or a sequence similar to it. The polynucleotide according to the first aspect and the gene product encoded by it are useful in industrial production of proteins.

According to the second aspect there is provided a fragment or a variant of the polynucleotide of the first aspect.

According to the third aspect there is provided a modified polynucleotide comprising the polynucleotide of the first aspect and containing at least one modification resulting into incapability of a gene product obtainable by transcribing and/or translating a chromosomal gene comprising the modified polynucleotide to induce expression of endogenous proteases in a host cell.

The modified polynucleotide of the third aspect encodes an inactive form or a fragment of the protease regulator encoded by the polynucleotide of the first aspect. It can be used to inactivate normal function of the protease regulator and, consequently, suppress endogenous protease expression in a host cell.

According to the fourth aspect there is provided a vector comprising the polynucleotide of the first aspect or the fragment or variant of the second aspect or the modified polynucleotide of the third aspect.

The polynucleotide can be inserted into the genome of a host cell for example in a vector. In certain embodiments the polynucleotide may encode an active or an inactive form of Pea1 and it may comprise genetic elements necessary for inserting the isolated polynucleotide at the region of the genome (locus) encoding the active protein by double crossover or replacement recombination. Thus, such a polynucleotide can be used in a method for activating or inactivating the gene encoding the protease regulator of the first aspect. In an embodiment the vector is a plasmid or a phage vector. Said polynucleotides and vectors may comprise 5' and 3' untranslated regions, regulatory sequences of pea1 for incorporating the genetic construction into the host genome and optionally at least one marker.

According to the fifth aspect there is provided a host cell comprising at least one inactivated chromosomal gene wherein the inactivated chromosomal gene comprises a nucleic acid sequence encoding a polypeptide comprising a sequence having at least 90% sequence identity with the amino acids 402-533 of SEQ ID NO: 13.

The host cell of the fifth aspect may produce less endogenous proteases than it would normally do when the chromosomal gene is active, or not inactivated. Thus, the protein degrading activity of the endogenous proteases of the host cells can be at least partially prevented in the host cell of the fifth aspect.

According to the sixth aspect there is provided a protein preparation comprising protein produced in the host cell of the fifth aspect. In certain embodiments the protein preparation comprises host cells according to the fifth aspect.

The protein preparation may have a higher content of the protein than a corresponding protein preparation produced using the same host cell with an intact pea1. Thus, when the protein preparation is used, a smaller total volumetric amount of the protein preparation may be required to obtain the same effect that would be required when using a protein preparation produced correspondingly but in which the biological effect of the protease regulator is the same than that of a native protease regulator. Further, the authenticity, stability and the shelf life of the protein preparation may be improved when the protein preparation contains less endogenous proteases of the host cell.

According to the seventh aspect there is provided a use of the protein preparation of the sixth aspect for biomass processing or in the industry of biofuel, starch, textile, detergent, pulp and paper, food, baking, feed, beverage or pharmaceutical industry.

The use of the seventh aspect is advantageous in that as the protein preparation comprises more protein, more protein activity can be obtained from a given amount of the protein preparation and the total amount of the protein preparation used can be decreased. Also problems related to endogenous protease activity in said industrial processes may be avoided.

According to an eighth aspect there is provided a method of producing a protein comprising
  a. growing the host cell of the fifth aspect in conditions suitable for producing the protein; and optionally
  b. recovering the protein.

The method of the eighth aspect provides improved yield and stability of the protein. Further, the method allows producing proteins that are difficult or in some cases even impossible to produce in a host cell because of their sensitivity to endogenous proteases of the host cell. In certain embodiments the protein is a recombinant protein.

According to the ninth aspect there is provided a composition comprising at least one of: the protein preparation of the sixth aspect; and the protein obtainable by the method of the eighth aspect. In certain aspects the composition may comprise at least one additional constituent such as buffer, salt, solvent, water or detergent.

The composition is advantageous in that it may have a higher content of the protein compared to a composition produced accordingly, but in a host cell with an active pea1 capable of inducing expression of endogenous proteases. Further, the composition may have a low content of endogenous proteases. In certain embodiments the protein may be sensitive to protease degradation and obtaining a stable composition produced in a host cell with an active pea1 would require purification steps to remove endogenous proteases induced by pea1. In such a case the composition may be easier to obtain with the method of the eighth aspect, because the initial level of endogenous proteases is low. Also, the composition may have improved shelf life and stability.

According to the tenth aspect there is provided a method for making a host cell for protein production comprising suppressing endogenous protease gene expression in a host cell by at least partially inhibiting transcription or translation of the polynucleotide of the first aspect.

The method is advantageous because it can be used to suppress many endogenous proteases simultaneously. The resulting host cell may be used to produce higher yields of any protein, such as endogenous proteins, recombinant proteins, heterologous proteins or any protein produced and optionally secreted by the host cell. Non-limiting examples of types of proteases the expression of which can be at least partially suppressed are listed in Table 2. In certain embodiment the method provides a host cell which has reduced expression level of at least one protease.

According to the eleventh aspect there is provided a host cell obtainable using the method of the tenth aspect.

According to the twelfth aspect there is provided a protease regulator selected from the group consisting of
- a) a polypeptide or a gene product encoded by the coding sequence of the polynucleotide of the first or the second aspect;
- b) a polypeptide or a gene product encoded by the coding sequence of the polynucleotide of the third aspect;
- c) a polypeptide encoded by the SEQ ID NO: 11 or 12;
- d) a polypeptide comprising an amino acid sequence which has at least 90% sequence identity to amino acids 402-533 of SEQ ID NO: 13; and
- e) a variant or a fragment of a polypeptide or a gene product of any one of a) to d).

The protease regulator of the twelfth aspect can be provided in a host cell to induce or suppress endogenous protease expression: a protease regulator having a biological effect of a native protease regulator may induce endogenous protease expression whereas an inactivated protease regulator may suppress endogenous protease expression. Further, fragments and variants may be used to interact with binding partners of the native pea1 gene product, e.g. to bind in a host cell an inactive fragment or variant of a pea1 gene product to a natural binding partner of a pea1 gene product.

According to the thirteenth aspect there is provided an antibody having binding specificity to the protease regulator of the twelfth aspect.

The antibody can be produced by methods known in the art. The antibody can be used to specifically bind the protease regulator. Thus, the presence of the protease regulator can be detected e.g. in an immunoassay when the antibody is directly or indirectly linked to a detectable label. Alternatively, the antibody can be used to bind the protease regulator to prevent binding of a binding partner to the protease regulator. In a further embodiment, when an antibody is used which binds a part of the protease regulator which does not participate in binding with its binding partner, the protease regulator with its binding partner can be bound in a complex with the antibody, and the binding partner can be identified with methods known in the art of protein chemistry. Thus, in an embodiment the antibody can be used as a research tool to identify biomolecules participating in regulation of protease expression.

According to the fourteenth aspect there is provided a method of inducing protease expression in a host cell by providing the protease regulator of the item a), c), d) or item e) referring to item a), c) or d) of the twelfth aspect inside or in contact with the host cell. In certain embodiments the method may comprise expressing the protease regulator in the host cell under control of promoter.

Embodiments of the present disclosure provide certain benefits. Depending on the embodiment, one or several of the following benefits may be achieved: improved protein production, possibility to produce proteins that are sensitive to proteases or otherwise unstable, improved authenticity, stability and shelf-life of compositions, decreased chemical consumption, decreased need for stabilizing agents, and decreased amounts of chemical, water and energy consumption when used in industrial processes.

Sequence Listings
- SEQ ID NO: 1: Nucleotide sequence of the QM6a genome v2.0 gene ID: 123125
- SEQ ID NO: 2: Nucleotide sequence of the QM6a genome v2.0 ID: 123125 cDNA
- SEQ ID NO: 3: Amino acid sequence of the QM6a genome v2.0 ID: 123125
- SEQ ID NO: 4: Nucleotide sequence of the RutC-30 genome v1.0 gene ID: 85889
- SEQ ID NO: 5: Nucleotide sequence of the RutC-30 genome v1.0 ID: 85889 cDNA
- SEQ ID NO: 6: Amino acid sequence of the RutC-30 genome v1.0 ID: 85889
- SEQ ID NO: 7: Nucleotide sequence of the pea1 gene in strain 33SP #9
- SEQ ID NO: 8: Nucleotide sequence of the pea1 gene in strain 31SP #4
- SEQ ID NO: 9: Nucleotide sequence of the pea1 gene in strain 31UV #22
- SEQ ID NO: 10: Nucleotide sequence of the pea1 gene in strain A21
- SEQ ID NO: 11: Nucleotide sequence of the pea1 gene cloned from QM6a (including 1140 bp upstream and 821 bp downstream sequences)
- SEQ ID NO: 12: Nucleotide sequence of the pea1 cDNA determined from QM6a (including 654 bp 5'UTR and 821 bp 3'-UTR sequences)
- SEQ ID NO: 13: The deduced amino acid sequence of the full-length Pea1 protein
- SEQ ID NO: 14: The deduced amino acid sequence of the Pea1 protein in strain 33SP #9
- SEQ ID NO: 15: The deduced amino acid sequence of the Pea1 protein in strain 31SP #4
- SEQ ID NO: 16: The deduced amino acid sequence of the Pea1 protein in strain 31UV #22
- SEQ ID NO: 17: The deduced amino acid sequence of the Pea1 protein in strain A21
- SEQ ID NO: 18: The truncated Pea1 protein encoded by pALK4106
- SEQ ID NO: 19: primer S-ppea1
- SEQ ID NO: 20: primer AS-3UTRout16
- SEQ ID NO: 21: primer S-5UTR26
- SEQ ID NO: 22: *Fusarium oxysporum* FOVG_08585
- SEQ ID NO: 23: *Gibberella fujikuroi* FFUJ_12153
- SEQ ID NO: 24: *Stachybotrys chartarum* S40293_07230
- SEQ ID NO: 25: *Claviceps purpurea* CPUR_05697
- SEQ ID NO: 26: *Ophiocordyceps sinensis* OCS_06053
- SEQ ID NO: 27: *Nectria haematococca* NECHADRAFT_85885
- SEQ ID NO: 28: *Metarhizium acridum* MAC_08836
- SEQ ID NO: 29: *Villosiclava virens* UV8b_6262
- SEQ ID NO: 30: *Acremonium chrysogenum* ACRE_079620

BRIEF DESCRIPTION OF THE FIGURES

FIG. 1, panel B shows SDS-PAGE analysis of culture supernatants from bioreactor batch cultivations of transformants producing the 20K+CBD protein from the pALK1769 expression cassette. Lane 1, sample deriving from the culture of a non-low-protease host of the same strain lineage as the transformation hosts; 2-6, samples from the cultures of strains transformed with pALK1769; one 33UV #82 transformant, two parallel 33SP #9 transformants, one 33UV #48 and one 33SP #11 transformant, respectively. Samples were taken after four days of cultivation in bioreactors. Equal amounts of the culture supernatants were loaded on each lane.

Figure 2:
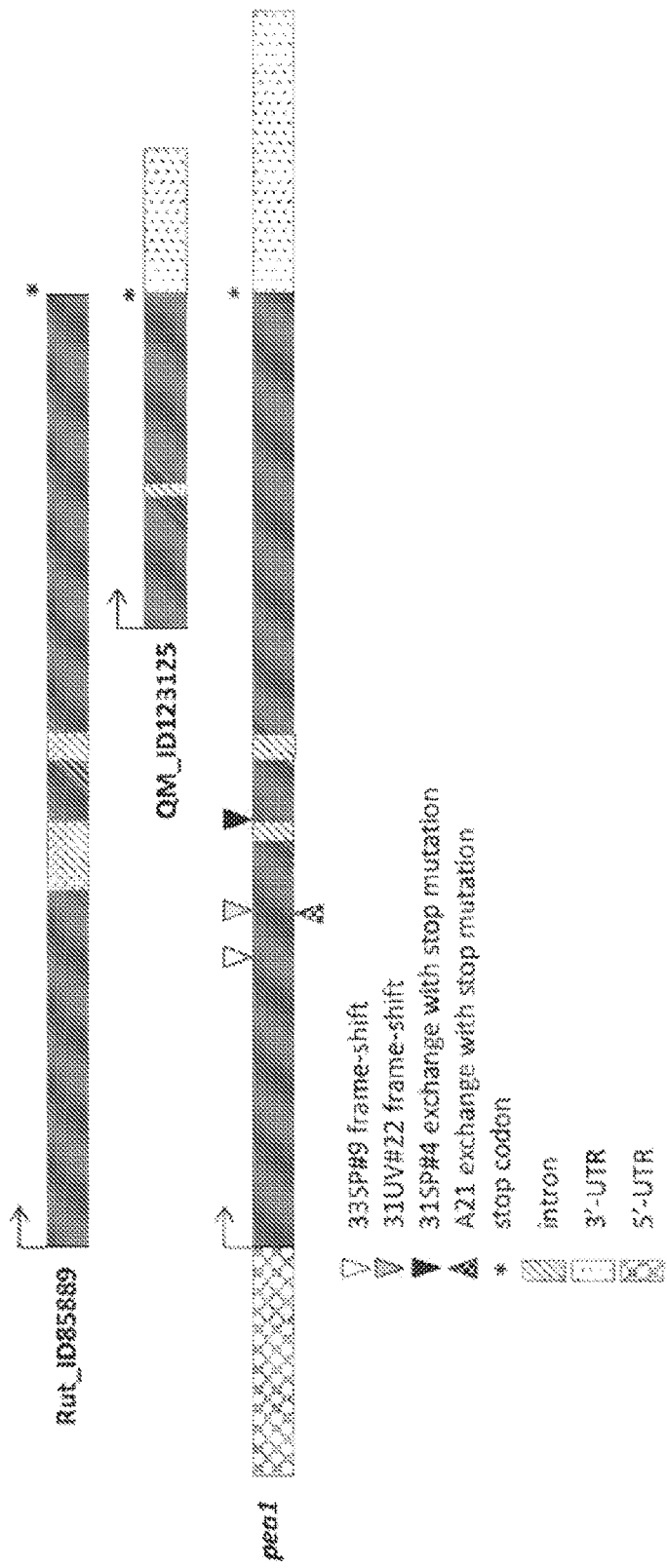

FIG. 2 schematically shows the annotations of the QM_ID123125, Rut_ID85889 and the annotation deduced from the cDNA derived from QM6a (pea1). The location of the mutations in strains 33SP #9, 31SP #4, 31UV #22 and A21 are shown with triangles in the pea1 annotation scheme.

FIG. 3 shows the nucleotide sequence of the pea1 gene (nucleotides 1141-3889 from SEQ ID NO: 11) and the deduced amino acid sequence. The length and location of the introns was determined from cDNA analysis and are shown in underlined, italics letters.

FIG. 4 shows the alignment of the amino acids of the Pea1 highly conserved region (amino acids 402-533 from SEQ ID NO: 13) with the corresponding regions of similar sequences from multiple species. Below the alignment is a symbol representing identical residues (*), conservative residues (:) and non-conservative residues ( ) according to a sequence alignment performed with Clustal Omega (on the world wide web at ebi.ac.uk/Tools/msa/clustalo/).

Figure 5A:
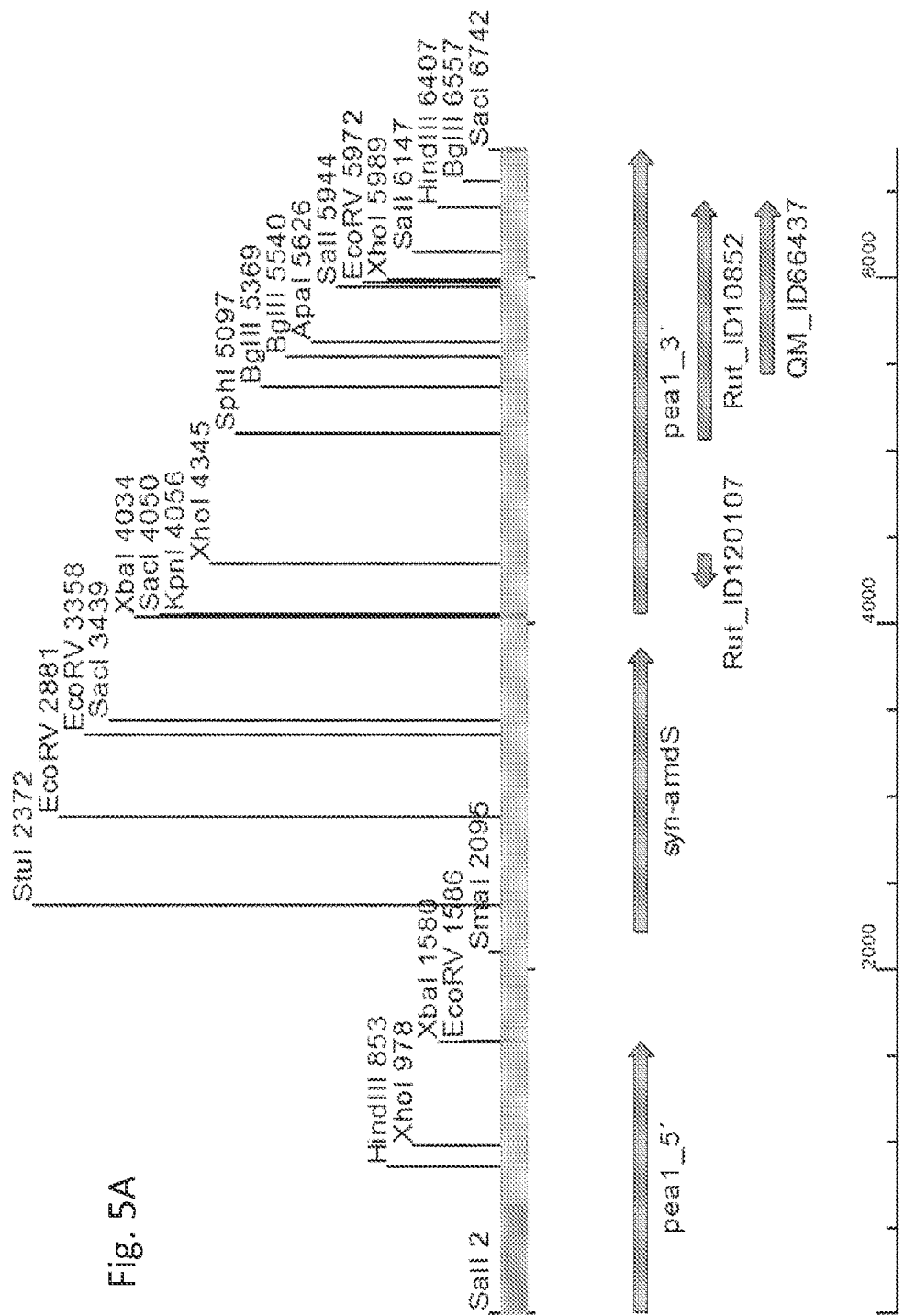

FIG. 5A shows the pALK4104 cassette for full-length pea1 gene deletion, the 6748 bp EcoRI-PstI fragment cleaved from the plasmid pALK4104. A selection of restriction enzyme sites is shown. pea1_5' and pea1_3', 5'- and 3'-flanking regions of the pea1 gene, respectively, used for targeting the deletion cassette to the pea1 locus for pea1 gene replacement with the marker gene; syn-amdS, synthetic amdS gene encoding acetamidase for selection of transformants; Rut_ID120107 and Rut_ID10852, the location and ID numbers of annotated genes according to RutC-30 public genome sequence; QM_ID66437, the location and ID number of an annotated gene, according to QM6a public genome sequence.

Figure 5B:
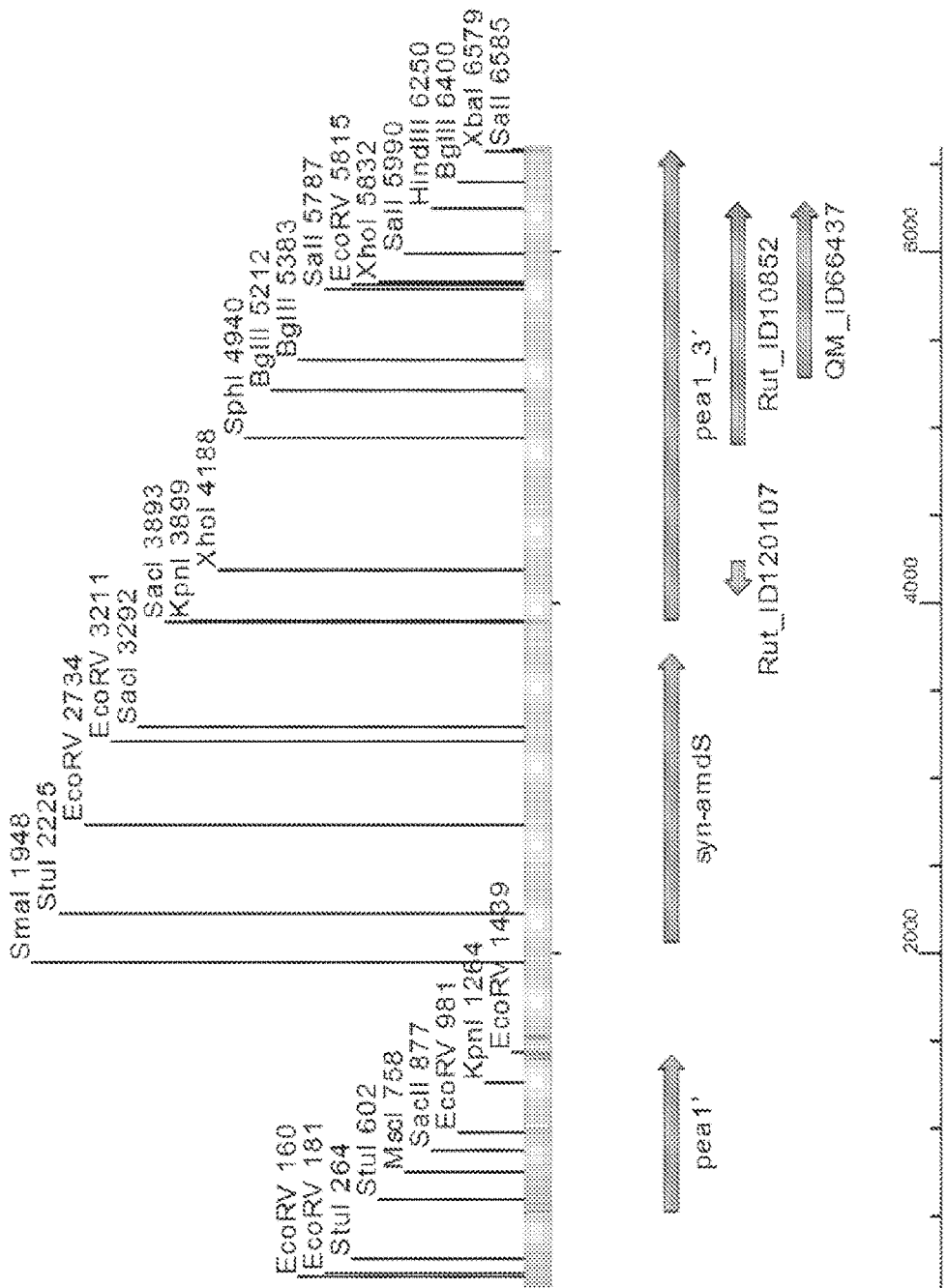

FIG. 5B shows the pALK4106 cassette for pea1 truncation, the 6595 bp EcoRI-PstI fragment cleaved from the plasmid pALK4106. A selection of restriction enzyme sites is shown. pea1', a truncated pea1 gene; pea1_3', syn-amdS, Rut_ID120107, Rut_ID10852 and QM_ID66437; identical genes/regions to those described for pALK4104 cassette (FIG. 5A).

Figure 6:
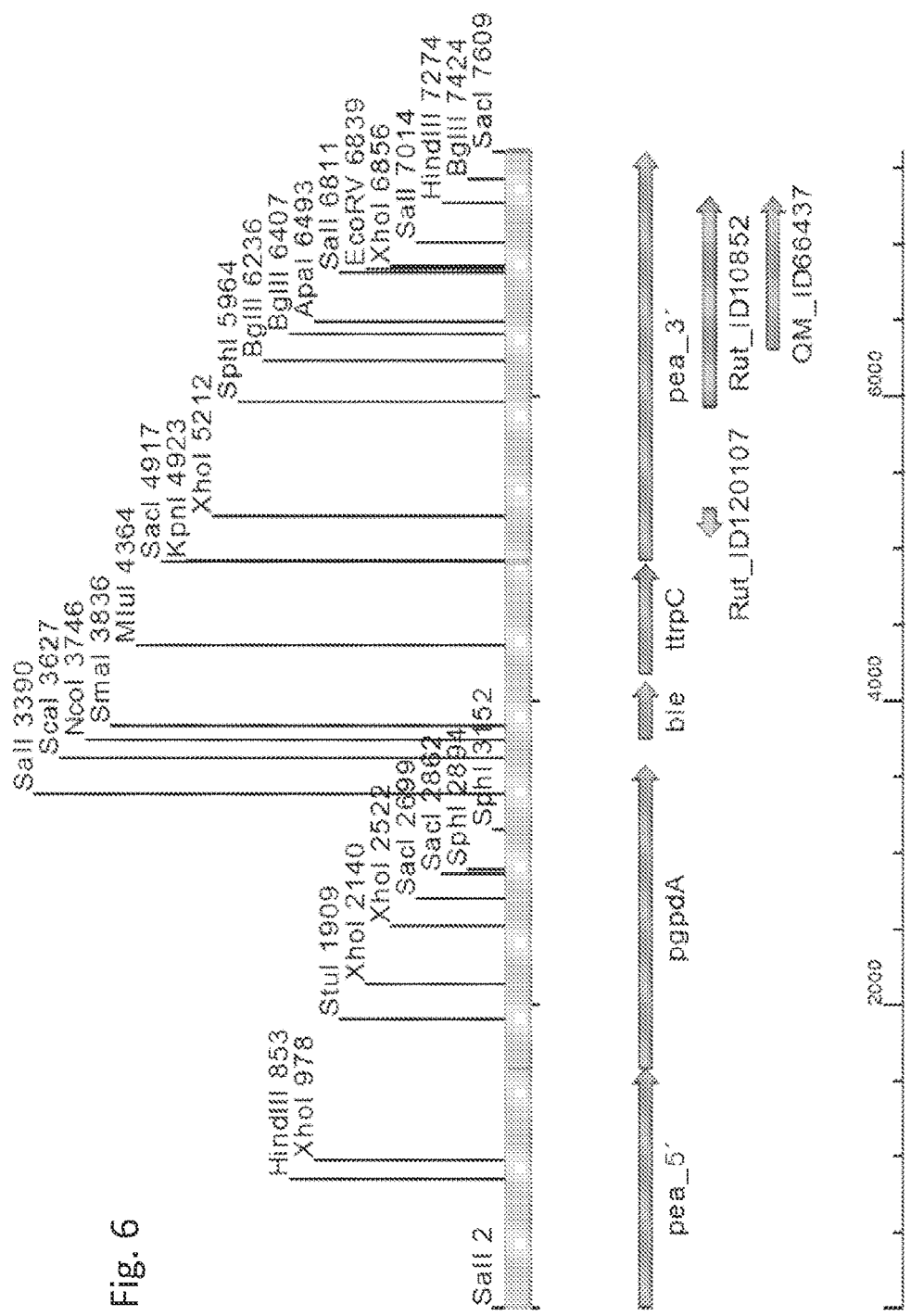

FIG. 6 shows the pALK4107 cassette for full-length pea1 gene deletion using the ble marker gene, the 7615 bp EcoRI-PstI fragment cleaved from the plasmid pALK4107. A selection of restriction enzyme sites is shown. pea_5', pea_3', Rut_ID120107, Rut_ID10852 and QM_ID66437, identical to those described for pALK4104 cassette (FIG. 5A); ble, gene originating from Streptoalloteichus hindustanus and encoding ShBle, giving resistance to antibiotics of the phleomycin family; pgpdA and ttrpC, originating from Aspergillus nidulans, the promoter from glyceraldehyde-3-phosphate dehydrogenase gene and terminator from a gene encoding polypeptide acting in the tryptophan biosynthesis, respectively. The ble with promoter and terminator were isolated from pAN8-1 plasmid (Mattern et al., 1988; NCBI gi: 475899).

FIG. 7 shows a sequence alignment of the deduced amino acid sequences of the truncated Pea1 proteins in strains 33SP #9 (SEQ ID NO: 14), 31SP #4 (SEQ ID NO: 15), 31UV #22 (SEQ ID NO: 16) and A21 (SEQ ID NO: 17) and the deduced amino acid sequence of the truncated Pea1 protein (SEQ ID NO: 18) encoded by the truncated pea1 in pALK4106 (FIG. 5B). The amino acids not matching to the amino acid sequence of the native Pea1 (SEQ ID NO: 13), i.e. amino acids generated by a frame-shift, are underlined.

Figure 8:
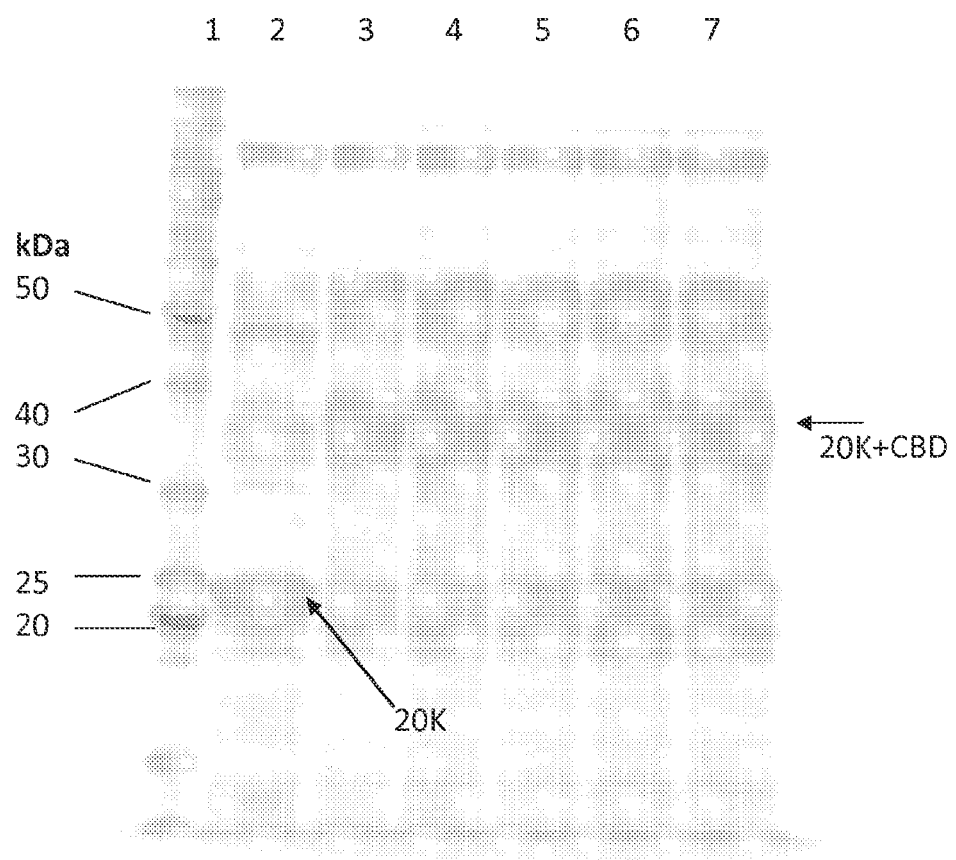

FIG. 8. SDS-PAGE analysis of Δpea1 transformants and host producing a recombinant cellulase protein. Samples were run into 12% SDS-polyacrylamide gel from culture supernatants of laboratory scale fermentations run for four days (same amount of sample from each fermentation). The gel was stained with Coo-massie Blue. 1, molecular mass marker; 2, culture supernatant from RF5969 cultivation; 3-7, culture supernatants from cultivations of five separate RF5969 transformants with pea1 deletion.

Figure 9:
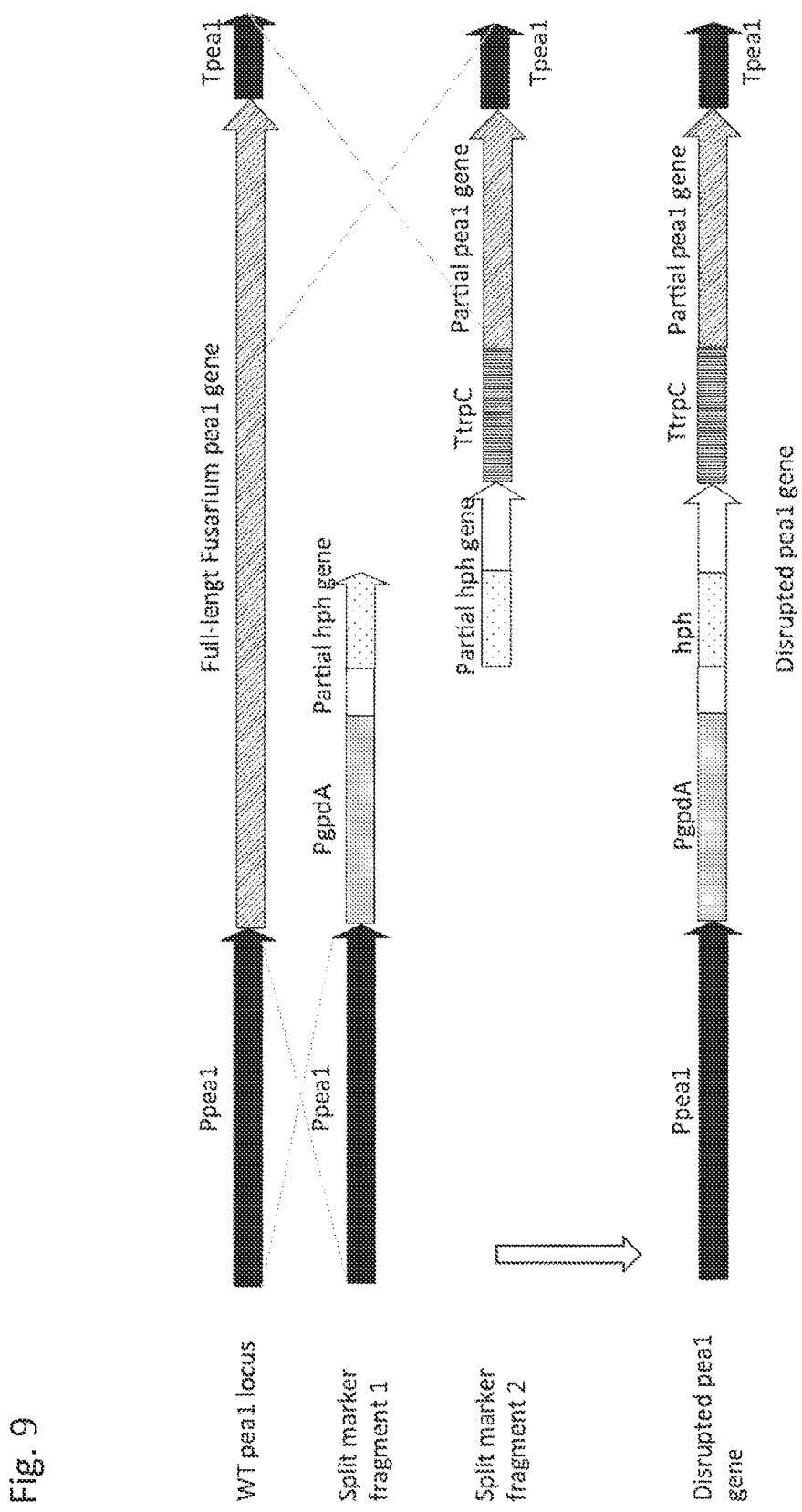

FIG. 9. Design of split marker approach to disrupt the pea1 homologues from Fusarium species. Ppea1, promoter region of the Fusarium oxysporum pea1 gene; pea1, F. oxysporum pea1 gene; Tpea1, terminator region of the F. oxysporum pea1 gene, PgpdA, promoter of Aspergillus glyseraldehyde-3-phosphate dehydrogenase gene; hph, gene encoding hygromycin phosphotransferase (for hygromycin resistance); TtrpC, terminator of the Aspergillus trpC (tryptophan C) gene. The regions for possible homologous recombinations are shown by crosses. The fragment sizes are not in scale.

FIG. 10. Protease activities from the culture supernatants of Fusarium oxysporum, F. fujikuroi and their transformants with disrupted pea1 gene. OXY WT and OXY-03, OXY-09, OXY-24, OXY-38, the protease activity analysed from the culture supernatants of F. oxysporum Fo47 and its four transformants, respectively; FUJI WT and FUJI-01, FUJI-08, FUJI-11 and FUJI-31, the protease activity results from the culture supernatants of F. fujikuroi MI58289 and its four transformants, respectively.

DEPOSITS

The following strain depositions according to the Budapest Treaty on the International Recognition of Deposit of Microorganisms for the Purposes of Patent Procedure were made:

The E. coli strain RF11697 including the plasmid pALK3535 was deposited at the Deutsche Sammlung von Mikroorganismen und Zellkulturen GmbH (DSMZ), Inhoffenstrasse 7 b, D-38124 Braunschweig, Germany on 4 Feb. 2015 and assigned accession number DSM 32007.

The E. coli strain RF11698 including the plasmid pALK3536 was deposited at the Deutsche Sammlung von Mikroorganismen und Zellkulturen GmbH (DSMZ), Inhoffenstrasse 7 b, D-38124 Braunschweig, Germany on 4 Feb. 2015 and assigned accession number DSM 32008.

DETAILED DESCRIPTION

Contrary to observations in prior art, the present inventors have identified and characterized a fungal protease expression regulator and successfully engineered a host cell suitable for industrial use which lacks the functional protease expression regulator or in which the protease regulator is inactivated. Without being bound to any theory, the present disclosure shows that by inactivating the protease regulator, expression levels of several endogenous proteases of the host cell can be significantly reduced. Thus, when the endogenous protease regulator is suppressed in a host cell, production of a protein of interest may be enhanced, resulting into improved yield and reduced proteolytic degradation of produced and/or secreted proteins. Simultaneously, fermentation performance, proliferation and protein production capabilities of the host cell may be maintained at levels required in industrial production of proteins.

As used herein, "pea1" means a polynucleotide comprising the sequence of SEQ ID NO: 11 nucleotides 1141-3889, as well as the sequence of the coding region in SEQ ID NO: 12 and sequences having similarity with said SEQ ID NOs. The pea1 gene encodes a gene product the suppression of which results into lowered expression of many fungal endogenous proteases. Thus, the gene is called a protease regulator, protease expression affecting 1, or pea1. 5' and 3' untranslated regions, promoter regions, introns, exons and regulatory sequences may have an effect on the function of pea1.

In certain embodiments the polynucleotide or the polypeptide of any aspect or embodiment is an isolated polynucleotide or an isolated polypeptide.

As used herein, "isolated" means a substance in a form or environment that does not occur in nature. Non-limiting examples of isolated substances include (a) any non-naturally occurring substance, (2) any substance including any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing or decreasing the amount of the substance relative to other components with which it is naturally associated (e.g., recombinant production in a host cell; multiple copies of a gene encoding the substance; and use of an alternative promoter to the promoter naturally associated with the gene encoding the substance).

As used herein, the term "comprising" includes the broader meanings of "including", "containing", and "comprehending", as well as the narrower expressions "consisting of" and "consisting only of".

As used herein, "fragment" means a protein or a polynucleotide having one or more amino acids or nucleotides deleted. In the context of DNA, a fragment includes both single stranded and double stranded DNA of any length. A fragment may be an active fragment which has the biological function, such as enzyme activity or regulatory activity, of the protein or the polynucleotide. A fragment may also be an inactive fragment, i.e. it does not have one or more biological effects of the native protein or polynucleotide.

As used herein, "variant" means a fragment of sequence (nucleotide or amino acid) inserted or deleted by one or more nucleotides/amino acids or which is chemically modified.

As used herein, a "peptide" and a "polypeptide" are amino acid sequences including a plurality of consecutive polymerized amino acid residues. For purpose of this invention, peptides are molecules including up to 20 amino acid residues, and polypeptides include more than 20 amino acid residues. The peptide or polypeptide may include modified amino acid residues, naturally occurring amino acid residues not encoded by a codon, and non-naturally occurring amino acid residues. As used herein, a "protein" may refer to a peptide or a polypeptide of any size. A protein may be an enzyme, a protein, an antibody, a membrane protein, a peptide hormone, regulator, or any other protein.

As used herein, "modification", "modified", and similar terms in the context of polynucleotides refer to modification in a coding or a non-coding region of the polynucleotide, such as a regulatory sequence, 5' untranslated region, 3' untranslated region, up-regulating genetic element, down-regulating genetic element, enhancer, suppressor, promoter, exon, or intron region. The modification may in some embodiments be only structural, having no effect on the biological effect, action or function of the polynucleotide. In other embodiments the modification is a structural modification which provides a change in the biological effect, action or function of the polynucleotide. Such a modification may enhance, suppress or change the biological function of the polynucleotide.

As used herein, "identity" means the percentage of exact matches of amino acid residues between two aligned sequences over the number of positions where there are residues present in both sequences. When one sequence has a residue with no corresponding residue in the other sequence, the alignment program allows a gap in the alignment, and that position is not counted in the denominator of the identity calculation. In this case, identity is a value determined with the Pairwise Sequence Alignment tool EMBOSS Needle at the EMBL-EBI website (www.ebi.ac.uk/Tools/psa/emboss_needle/).

As used herein, "similarity" means the percentage of matches between two sequences over the reported aligned region. In addition to identically matching amino acids (identity), similarity allows conservative substitutions (change to an amino acid with similar physical-chemical properties) to be factored into the percentage value. In this case, similarity is a value determined with the Pairwise Sequence Alignment tool EMBOSS Needle at the EMBL-EBI website (www.ebi.ac.uk/Tools/psa/emboss_needle/).

As used herein, "host cell" means any cell type that is susceptible to transformation, transfection, transduction, or the like with a nucleic acid construct or expression vector comprising a polynucleotide. The term "host cell" encompasses any progeny that is not identical due to mutations that occur during replication. Non-limiting examples of a host cell are fungal cells, filamentous fungal cells from Division Ascomycota, Subdivision Pezizomycotina; preferably from the group consisting of members of the Class Sordariomycetes, Subclass Hypocreomycetidae, Orders Hypocreales and Microascales and *Aspergillus, Chrysosporium, Myceliophthora* and *Humicola*; more preferably from the group consisting of Families Hypocreacea, Nectriaceae, Clavicipitaceae, Microascaceae, and Genera *Trichoderma* (anamorph of *Hypocrea*), *Fusarium, Gibberella, Nectria, Stachybotrys, Claviceps, Metarhizium, Villosiclava, Ophiocordyceps, Cephalosporium,* and *Scedosporium*; more preferably from the group consisting of *Trichoderma reesei (Hypocrea jecorina), T. citrinoviridae, T. longibrachiatum, T. virens, T. harzianum, T. asperellum, T. atroviridae, T. parareesei, Fusarium oxysporum, F. graminearum, F. pseudograminearum, F. venenatum, Gibberella fujikuroi, G. moniliformis, G. zeaea, Nectria (Haematonectria) haematococca, Stachybotrys chartarum, S. chlorohalonata, Claviceps purpurea, Metarhizium acridum, M. anisopliae, Villosiclava virens, Ophiocordyceps sinensis, Acremonium (Cephalosporium) chrysogenum,* and *Scedosporium apiospermum,* and *Aspergillus niger, Aspergillus awamori, Aspergillus oryzae, Chrysosporium lucknowense, Myceliophthora thermophila, Humicola insolens,* and *Humicola grisea*, most preferably *Trichoderma reesei*. In an embodiment the host cell is selected from the following group of strains obtainable from public collections: QM6a, ATC 3631; RutC-30, ATCC56765; QM9414, ATCC26921, and derivatives thereof.

As used herein, low stringency conditions mean for probes of at least 100 nucleotides in length conditions corresponding to hybridizing at prehybridisation and hybridisation at 55° C. in 5×SSC, 0.1% N-lauroylsarcosine, 0.02% SDS, 1% blocking reagent (Roche 11 096 176 001), following standard Southern blotting procedures for 12 to 24 hours. The carrier material is finally washed two to three times each for 15 minutes using 2×SSC, 0.1% SDS at 55° C.

As used herein, high stringency conditions mean for probes of at least 100 nucleotides in length conditions corresponding to hybridizing at prehybridisation and hybridization at 65° C. in 5×SSC, 0.1% N-lauroylsarcosine, 0.02% SDS, 1% blocking reagent (Roche 11 096 176 001), following standard Southern blotting procedures for 12 to 24 hours. The carrier material is finally washed two to three times each for 15 minutes using 0.1×SSC, 0.1% SDS at 65° C.

As used herein, "expression" includes any step involved in the production of a polypeptide in a host cell including, but not limited to, transcription, translation, post-translational modification, and secretion. Expression may be followed by the harvesting, i.e. recovering, the host cells or the expressed product.

As used herein, inhibiting, inactivating, suppressing and down-regulating mean at least partially preventing the biological action of pea1 gene or the gene product. As understood in the art, this can be accomplished at transcriptional, translational or protein level, i.e. by preventing reading or expressing the pea1 gene, preventing correct translation of the Pea1 protein or by preventing the pea1 gene product from binding to its binding partner(s) that in natural conditions participate in action of pea1 gene product.

As used herein a protease induced by the protease regulator of the first aspect can be any protease whose expression is induced by the protease regulator, and whose expression and/or protease activity is reduced when the protease regulator is inactivated. Non-limiting examples of such proteases are aspartic proteases, serine proteases, glutamic proteases and metalloproteases (Table 2). Thus, a biological effect of pea1 may be to regulate expression of endogenous proteases.

As used herein, a "gene product" is RNA or protein resulting from expression of a polynucleotide. Examples of gene products include mRNA, siRNA, cDNA, protein, polypeptide, and peptide.

In an example embodiment of the first aspect the host cell is *Trichoderma*.

In an example embodiment of the first aspect the nucleotide sequence encodes a protein comprising an amino acid sequence with 90%, 91%, 92%, 93%, 94%, 95%, 96%, 97%, 98%, 99% or 100% sequence identity to amino acids 402-533 of SEQ ID NO: 13. In another embodiment the nucleotide sequence encodes a protein comprising an amino acid sequence with 90%, 91%, 92%, 93%, 94%, 95%, 96%, 97%, 98%, 99% or 100% sequence similarity to amino acids 402-533 of SEQ ID NO: 13.

In an example embodiment of the first aspect the polynucleotide is selected from the group consisting of the coding sequence of SEQ ID NO: 11 and 12.

In an example embodiment of the first aspect the polynucleotide is selected from the group consisting of:
 a) a polynucleotide comprising a sequence having at least 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with the nucleotides 1141-3889 of SEQ ID NO: 11;
 b) the polynucleotide of SEQ ID NO: 12 or the coding sequence thereof; c) the polynucleotide of SEQ ID NO: 11 or the coding sequence thereof; and d) a nucleotide sequence hybridisable with a nucleotide sequence which is complementary to any one of a) to c) under high stringency conditions.

In an example embodiment of the first aspect the polynucleotide or its non-coding region contains at least one modification. In certain embodiments of the first aspect the modification makes it structurally different compared to any naturally occurring protease regulator, or the modification makes its expression and/or translation different, e.g. in terms of efficiency or stability compared to those of any naturally occurring protease regulator. The modification may have an effect on a biological function or another property of the protease regulator. In another embodiment the modification does not substantially change a biological function or other property of the protease regulator. Thus, in certain embodiments the modification does not substantially diminish the capability of the polynucleotide of the first aspect to induce expression of endogenous proteases in a host cell.

In an example embodiment the polynucleotide of the first aspect, the fragment or variant of the second aspect, or the modified polynucleotide of the third aspect comprises genetic elements to allow its transcription and/or translation in a host cell. In another embodiment the polynucleotide additionally comprises genetic elements that allow secreting the protein outside the host cell.

In an example embodiment of the fourth aspect the vector comprises genetic elements for incorporating the polynucleotide of the second aspect or the above embodiment into the genome of a host cell. In certain embodiments the genetic elements comprise 5' untranslated region and/or 3' untranslated region optionally in a form of a cassette.

In an example embodiment of the fifth aspect the host cell is selected from the group consisting of filamentous fungal cells from Division Ascomycota, Subdivision Pezizomycotina; preferably from the group consisting of members of the Class Sordariomycetes, Subclass Hypocreomycetidae, Orders Hypocreales and Microascales and *Aspergillus, Chrysosporium, Myceliophthora* and *Humicola*; more preferably from the group consisting of Families Hypocreacea, Nectriaceae, Clavicipitaceae, Microascaceae, and Genera *Trichoderma* (anamorph of *Hypocrea*), *Fusarium, Gibberella, Nectria, Stachybotrys, Claviceps, Metarhizium, Villosiclava, Ophiocordyceps, Cephalosporium,* and *Scedosporium*; more preferably from the group consisting of *Trichoderma reesei* (*Hypocrea jecorina*), *T. citrinoviridae, T. longibrachiatum, T. virens, T. harzianum, T. asperellum, T. atroviridae, T. parareesei, Fusarium oxysporum, F. gramineanum, F. pseudograminearum, F. venenatum, Gibberella fujikuroi, G. moniliformis, G. zeaea, Nectria (Haematonectria) haematococca, Stachybotrys chartarum, S. chlorohalonata, Claviceps purpurea, Metarhizium acridum, M. anisopliae, Villosiclava virens, Ophiocordyceps sinensis, Acremonium (Cephalosporium) chrysogenum,* and *Scedosporium apiospermum,* and *Aspergillus niger, A. awamori, A. oryzae, Chrysosporium lucknowense, Myceliohpthora thermophila, Humicola insolens, Humicola grisea,* most preferably *Trichoderma reesei*. In an embodiment the host cell is selected from the following group of strains obtainable from public collections: QM6a, ATC 3631; RutC-30, ATCC56765; QM9414, ATCC26921, and derivatives thereof.

In an example embodiment of the fifth aspect the inactivated chromosomal gene comprises the polynucleotide of the first aspect.

In an example embodiment of the fifth aspect the inactivated chromosomal gene is inactivated by disruption e.g.

with a selectable marker, inhibition of translation or transcription of the chromosomal gene, at least partial deletion, truncation, deletion, insertion, mutation, or silencing, by RNAi or by CRISPR/Cas9 technology. When RNAi is used, double stranded RNA can be used to post-translationally silence expression levels of a specific gene, such as pea1, due to sequence-specific degradation mediated by small double-stranded RNAs. E.g. in vitro synthesised dsRNA and siRNA molecules or in vivo synthesised dsRNA or stem-loop hairpin RNA can be designed and used as triggers for targeting. When CRISPR/Cas9 technology is used in the inactivation, the Cas9 protein and appropriate guide RNAs (according to target sequence, such as pea1) are delivered into the cell, resulting to cleavage at desired location.

In an example embodiment of the fifth aspect the host cell comprises genetic elements to allow expressing, under conditions suitable for promoting expression, at least one protein of interest encoded by a recombinant polynucleotide. It is within the level of skill in the art to choose the suitable conditions, including reagents and conditions for RNA expression from the expression construct, followed by translation of the encoded polypeptide. Exemplary reagents and conditions are described in the examples that follow. The methods of this embodiment may also be carried out in a cell free translation system or in vivo. In a preferred embodiment, the protein expression is carried out in a recombinant host cell.

In an example embodiment of the fifth aspect the protein of interest is selected from the list consisting of a pharmacologically active protein, antibody, antibody fragment, therapeutic protein, biosimilar, multi-domain protein, peptide hormone, antimicrobial peptide, peptide, carbohydrate binding module, enzyme such as cellulase, protease, protease inhibitor, aminopeptidase, amylase, carbohydrase, carboxypeptidase, catalase, chitinase, cutinase, deoxyribonuclease, esterase, alpha-galactosidase, beta-galactosidase, glucoamylase, alpha-glucosidase, beta-glucosidase, invertase, laccase, lipase, mannanase, mutanase, oxidase, pectinolytic enzyme, peroxidase, phospholipase, phytase, phosphatase, polyphenoloxidase, redox enzyme, proteolytic enzyme, ribonuclease, transglutaminase and xylanase. One or more proteins of interest may be expressed by the same host cell.

In an example embodiment of the sixth aspect the protein preparation comprises at least one further component selected from stabilizer, preservative, fragrant, buffer, salt and colorant.

In an example embodiment of the tenth aspect the inhibiting is provided by making an inactivating modification in the gene comprising the sequence of the polynucleotide of the first aspect. The modification may be deletion, truncation or mutation of at least part of the protease regulator, including its control sequence, which results into suppression or at least partial inhibition of the capability of the protease regulator to induce expression of endogenous proteases in the host cell. In another embodiment the function of the protease regulator gene is inactivated post-translationally, e.g. by inhibiting protein-protein interaction or by inhibiting binding of the protease regulator to any of its natural binding partners. In yet another embodiment the protease regulator is inactivated by a deleting a promoter or other regulatory region of the present protease regulator.

In an example embodiment of the tenth aspect the inhibition is achieved by mutation, deletion, insertion, RNA interference, antibody, or small molecule inhibitor.

In an example embodiment of the eleventh aspect the host cell further comprises a nucleic acid encoding a heterologous protein.

In an example embodiment of the eleventh aspect the host cell is a fungal cell, preferably a filamentous fungal cell, such as Trichoderma or Trichoderma reesei.

Examples

Example 1. Isolation of Low Protease Mutants from Trichoderma reesei Strains

The Trichoderma reesei A21 is a low protease UV mutant deriving from the T. reesei QM9414 strain lineage. A21 strain was screened from the mutants obtained after ultraviolet light irradiation of parent spore batches by using a skim milk plate assay. It produced a reduced halo in the selection plate compared to its parent, indicating lowered protease production. A21 was confirmed to produce clearly lowered amounts of protease activities into its culture supernatants compared to its parent, both in shake flask cultivations and in laboratory scale bioreactors in cellulase inducing medium. It was shown by FPLC analysis that A21 lacks e.g. a protein peak which in the parent strain showed protease activity that could be inhibited by pepstatin A, indicating no or lower production of at least an aspartic type of a protease or proteases, compared to the parent.

To develop mutants with decreased production levels of native proteases from a different T. reesei mutant strain lineage, the proprietary industrial strains A31 and A33 were chosen for a strain development program. A31 is a T. reesei mutant strain with high protein (cellulase) production capacity. A33 is a genetically modified derivative from A31 from which the four major native cellulases encoding genes cbh1 (cel7A), cbh2 (cel6A), egl1 (cel7B) and egl2 (cel6A) have been deleted using the pyr4 counter selection method (for the method, see Seidl and Seiboth, 2010). The A31 and A33 mutants were generated by using UV mutagenesis and by selecting spontaneous low protease mutants using the suicide (SUI) method (Braaksma A M., Punt P. J. 2008. Aspergillus as a cell factory for protein production Controlling protease activity in fungal production. In: Goldman G H, Osmani S A, editors. The Aspergilli. Genomics, Medical Aspects, Biotechnology, and Research Methods. Boca Raton, Florida: CRC Press; Taylor & Francis) developed at TNO (The Netherlands). This method is based on a proprietary SUI chemical to which the strains producing lowered amounts of proteases are more resistant than the parent strains. By using the SUI approach the screening of low protease mutants (strains) is quick and efficient. However, the screening of such mutants can also be performed by direct plating of the mutated spores (or spores) on skim milk or other suitable protease detection plates.

The T. reesei strains were inoculated and cultivated on PD (potato dextrose agar) plates for generating spores for mutagenesis. The UV mutagenesis was conducted using BioRad UV chamber and irradiation time of 40-80 s (with survival rate of 5-50%). Non-mutagenised and UV-treated spore batches were plated on Trichoderma minimal medium (TMM; Penttilä M, H Nevalainen, M Rättö, E Salminen, and J Knowles. 1987. A versatile transformation system for the cellulolytic filamentous fungus Trichoderma reesei. Gene 61:155-164) based agar plates containing different concentrations of the SUI reagent (50-500 μg/ml) and AMMNH4-plates (Bennett, J. W. and Lasure, L. L. 1991. Growth media. In More Gene Manipulations in Fungi, pp 441-447. Edited by J. W. Bennett & L. L. Lasure, San Diego, Cal.; Academic Press. ISBN 0-12-088642-1) with 25-500 µg/ml of SUI to select for low protease mutants.

From both *T. reesei* strains about $5 \times 10^7$ non-mutagenized and $1-2 \times 10^7$ mutagenized spores were screened on the SUI plates. After the first SUI selection round 200-300 SUI resistant colonies from each strain were rescreened on SUI plates. About 75% of the strains still showed SUI resistant phenotype. The above type of strains were then analysed on TMM-NO$_3$+skim milk plates (100 ml of 10% skim milk added to TMM after autoclaving, (NH$_4$)$_2$SO$_4$ replaced with 6 g/l of NaNO$_3$). In skim milk plates about 20-40 strains (about 15% from both A31 and A33) showed no or reduced halo compared to the parental strains indicating very low or low protease production. A selection of strains was purified via single spores. These strains were further characterized on cellulose (0.5% Walseth) and xylan (0.5% oat spelt xylan) plates (A31 derived strains) or on xylan plates (A33 derived strains) to confirm that they still were capable of producing cellulase and/or xylanase activities. A selection of strains with lowered protease production, but similar cellulase and/or xylanase production on plates compared to the parents, were chosen for further analysis and characterisation. Their growth and protein and protease production levels were analysed in shake flask and bioreactor cultivations (Example 2). The suitability of chosen strains as hosts for production of protease sensitive proteins was also tested (Example 3).

Example 2. Characterisation of the Low Protease Mutant Strains

A selection of low protease mutants, based on the plate assay results, were cultivated in shake flasks using cellulase inducing lactose based minimal medium (Bailey, M. J.; Askolin, S.; Horhammer, N.; Tenkanen, M.; Linder, M.; Penttila, M.; Nakari-Setala, T. (2002): Process technological effects of deletion and amplification of hydrophobins I and II in transformants of *Trichoderma reesei*. In Applied microbiology and biotechnology 58(6), pp. 721-727). The protease activities were measured from the culture supernatants using dimethylated casein or BSA (bovine serum albumin) as substrates, based on the procedure described by Holm (Holm K. A. 1980. Automated colorimetric determination of acid proteinase activity in fermentation samples using a trinitrobenzenesulphonic acid reagent. Analyst. 105(1246): 18-24) and using glycine for calibration. For the casein assay, the pHs used in the activity measurements were 5.5, 7.0 and 8.5 and for the BSA assay pHs 4.0 and 6.0 were used. Various protease activity levels were seen in the culture supernatants among the mutant strains. However, a number of mutants (but not all) that had showed a reduced protease activity in milk halo assay also showed reduced protease activities in the liquid cultures. Some of the selected mutants showed similar or better cellulase and/or xylanase activities compared to the host. However, some of the selected mutants showed reduced cellulase and/or xylanase activities, indicating a general deficiency in protein secretion in these strains.

Based on the results from the skim milk plate assay and the minimal medium cultivation, altogether 22 A31 and 23 A33 derived low protease strains were chosen to be cultivated in shake flasks using a complex lactose-based cellulase inducing medium (Joutsjoki, V. V., T. K. Torkkeli, and K. M. H. Nevalainen. 1983. Transformation of *Trichoderma reesei* with the *Hormoconis resinae* glucoamylase P (gamP) gene: production of a heterologous glucoamylase by *Trichoderma reesei*, Curr. Genet. 24:233-228) buffered with 5% KH$_2$PO$_4$. The strain selection included both spontaneous and UV mutants. The protease activities as well as the amounts of secreted proteins and relevant enzyme activities (e.g. cellulase, xylanase) were quantified from the culture supernatants to confirm that the protease activities were decreased compared to the parent strain, but the amounts of other secreted proteins were not. The strains were inoculated from PD slants to shake flasks (50 ml volume of medium in 250 ml flask). Each of the strains was cultivated in two flasks with pH of the medium adjusted (prior to autoclaving the culture media) to 5.5 and 6.0. The cultivations were performed at 30° C., 250 rpm for 7 days. Samples were taken and analysed after 3, 5 and 7 days of cultivation. The pH (representing strain growth), the amount of secreted proteins (BioRad DC method), cellulase activities (hydroxyethylcellulose and 4-methylumbelliferyl-β-D-lactoside as substrates), xylanase activity (birch xylan as a substrate; Bailey, M. J.: Biely, P.; Poutanen, K. (1992): Interlaboratory testing of methods for assay of xylanase activity. In *Journal of Biotechnology* 23, pp. 257-270) and protease activities were measured from the culture supernatants. The protease activities were measured using haemoglobin (4.0 g in 100 ml water; at pH 4.7, 40° C., 30 min reaction; resulting to HUT activity units) and casein (1.2 g in 100 ml 30 mM ammoniumphosphate buffer; pH 7.0, 30° C., 60 min reaction) as substrates.

Some of the strains produced clearly lowered protease activities compared to their parents (Table 1). Also, a selection of the strains produced at least similar amounts of secreted proteins, cellulase and/or xylanase activities as their parent strain. Some of the strains even produced increased amounts of proteins and cellulase/xylanase activities compared to their parent. No obvious differences between the parent and the low protease strains in the protein patterns of the culture supernatants were detected in 12% SDS-PAGE gels. (Criterion XT, Biorad).

TABLE 1

Relative protease (HUT) activities measured from the culture supernatants of the low-protease mutants grown in shake flasks for 7 days. A. A31 derived low protease mutants. B. A33 derived low protease mutants. Results are included from a selection of strains which produced less protease activities, but at least similar amounts of secreted proteins and enzyme activities as the parent strain in the cultivation. Strains with the code NSP or SP are spontaneous mutants, those with the code UV derive from spores treated with UV irradiation. TMM and AMM, selection plate used (see Example 1 for details); SUI50-SUI500, concentration of the SUI reagent on plate used in primary screening. pH 5.5 and pH 6.0, the pH of the culture medium, adjusted prior to autoclaving.

A.

| Strain No. | Primary screening plate | Protease activity (relative HUT) | |
|---|---|---|---|
| | | pH 5.5 | pH 6.0 |
| A31 | | 100 | 100 |
| 31NSP#1 | TMM-SUI50 | 105 | 35 |
| 31SP#4 | TMM-SUI100 | 21 | 41 |
| 31SP#7 | TMM-SUI500 | 37 | 49 |
| 31UV#22 | TMM-SUI50 | 14 | 95 |
| 31NSP#6 | TMM-SUI50 | 36 | 44 |
| 31NSP#7 | TMM-SUI50 | 35 | 107 |
| 31NSP#8 | TMM-SUI50 | 62 | 42 |

TABLE 1-continued

Relative protease (HUT) activities measured from the culture supernatants of the low-protease mutants grown in shake flasks for 7 days. A. A31 derived low protease mutants. B. A33 derived low protease mutants. Results are included from a selection of strains which produced less protease activities, but at least similar amounts of secreted proteins and enzyme activities as the parent strain in the cultivation. Strains with the code NSP or SP are spontaneous mutants, those with the code UV derive from spores treated with UV irradiation. TMM and AMM, selection plate used (see Example 1 for details); SUI50-SUI500, concentration of the SUI reagent on plate used in primary screening. pH 5.5 and pH 6.0, the pH of the culture medium, adjusted prior to autoclaving.

B.

| Strain No. | Primary screening | Protease activity (relative HUT) | |
|---|---|---|---|
| | | pH 5.5 | pH 6.0 |
| A33 | | 100 | 100 |
| 33SP#9 | AMM-SUI25 | 29 | 43 |
| 33SP#11 | AMM-SUI100 | 27 | 44 |
| 33SP#12 | AMM-SUI150 | 26 | 34 |
| 33UV#48 | TMM-SUI50 | 26 | 50 |
| 33UV#64 | AMM-SUI50 | 27 | 39 |
| 33UV#68 | AMM-SUI50 | 30 | 37 |
| 33UV#82 | AMM-SUI50 | 37 | 45 |

A selection of A31 and A33 derived strains were cultivated in laboratory scale bioreactors in cellulase inducing complex medium. The amounts of secreted proteins, relevant enzyme activities (e.g. cellulase and xylanase activities) and protease activities were analysed from the spent culture media. The results obtained confirmed the low protease characteristics of most of the strains. The chosen samples from the fermentations were further used for analysis and identification of proteases secreted into the culture media by using protein separation, IEF and zymogram analysis and peptide mass mapping (Example 4). Samples of fungal mycelia were collected from the fermentations for Northern blot expression analysis (Example 4).

Example 3. Low Protease Strains as Hosts for Production of Homologous and Heterologous Proteins Chosen low protease strains deriving from A31 (31SP #4, 31UV #22 and 31 NSP #6) and A33 (33SP #11, 33UV #82, 33SP #9 and 33UV #48) were tested as host for expressing two genes encoding heterologous proteins, known from previously performed expression studies to be protease sensitive when produced in *T. reesei* strains. The genes expressed in the chosen low protease strains were as follows: *Melanocarpus albomyces* derived, modified endoglucanase named as 20K+CBD (with a protease sensitive linker "WGEI"; expressed from the pALK1769 cassette; EP1874927) and *Streptomyces mobaraensis* transglutaminase (TGase; Washizu, K.; Ando, K.; Koikeda, S.; Hirose, S.; Matsuura, A.; Takagi, H. et al. (1994); Molecular cloning of the gene for microbial transglutaminase from *Streptoverticillium* and its expression in *Streptomyces lividans*. In *Biosci. Biotechnol. Biochem.* 58 (1), pp. 82-87). The genes were expressed from the native *T. reesei* cbh1 (cel7A) promoter. The 20K+CBD encoding gene was directly fused to the cbh1 promoter but the TGase gene (pro/mature protein encoding region) was fused 3-prime to the *T. reesei* Man5A carrier polypeptide encoding sequence (fused to the cbh1 promoter) in a similar way as described for a xylanase gene expression in Paloheimo et al. (Paloheimo, M., A. Mäntylä, J. Kallio, and P. Suominen. 2003. High-yield production of a bacterial xylanase in the filamentous fungus *Trichoderma reesei* requires a carrier polypeptide with an intact domain structure. Appl. Env. Microbiol. 69:7073-7082). The amdS (acetamidase) gene was used as a marker in both the expression cassettes.

The linear expression cassettes were isolated from the vector backbones and were transformed to protoplasts prepared from the low protease strains. The transformations were performed as in Penttilä et al. (Penttilä M, H Nevalainen, M Rättö, E Salminen, and J Knowles. 1987. A versatile transformation system for the cellulolytic filamentous fungus *Trichoderma reesei*. Gene 61:155-164) with the modifications described in Karhunen et al. (Karhunen, T., A. Mäntylä, K, M. H. Nevalainen, and P. L. Suominen. 1993. High frequency one step gene replacement in *Trichoderma reesei*, I. Endoglucanase I overproduction. Mol. Gen. Genet. 241:515-522). The transformants were purified on acetamide selection plates through single conidia prior to sporulating them on PD. The transformants were inoculated from the PD slants to shake flasks containing 50 ml of complex lactose-based cellulase inducing medium (Joutsjoki, V. V., T. K. Torkkeli, and K. M. H. Nevalainen. 1993. Transformation of *Trichoderma reesei* with the *Hormoconis resinae* glucoamylase P (gamP) gene: production of a heterologous glucoamylase by *Trichoderma reesei*. Curr. genet. 24:223-228) buffered with 5% $KH_2PO_4$ and pH adjusted to 5.5 or 6.0. The enzyme production of the transformants was analysed from the culture supernatants after growing them for 7 days at 30° C., 250 rpm. The chosen transformants were also cultivated in laboratory scale bioreactors using cellulase inducing complex medium and analysis of the enzyme production was performed. The production of recombinant proteins and their stability in the culture broths was analysed from the culture supernatants by enzyme activity assays and running samples on SDS-PAGE gels. For the TGase detection also a Western blot analysis was performed using in detection a commercial antibody for the bacterial transglutaminase. The stability of the recombinant protein was analysed by incubating samples of the culture supernatants at different temperatures for different periods of time and analysing them using SDS-PAGE (and/or Western blot) method.

Figure 1:
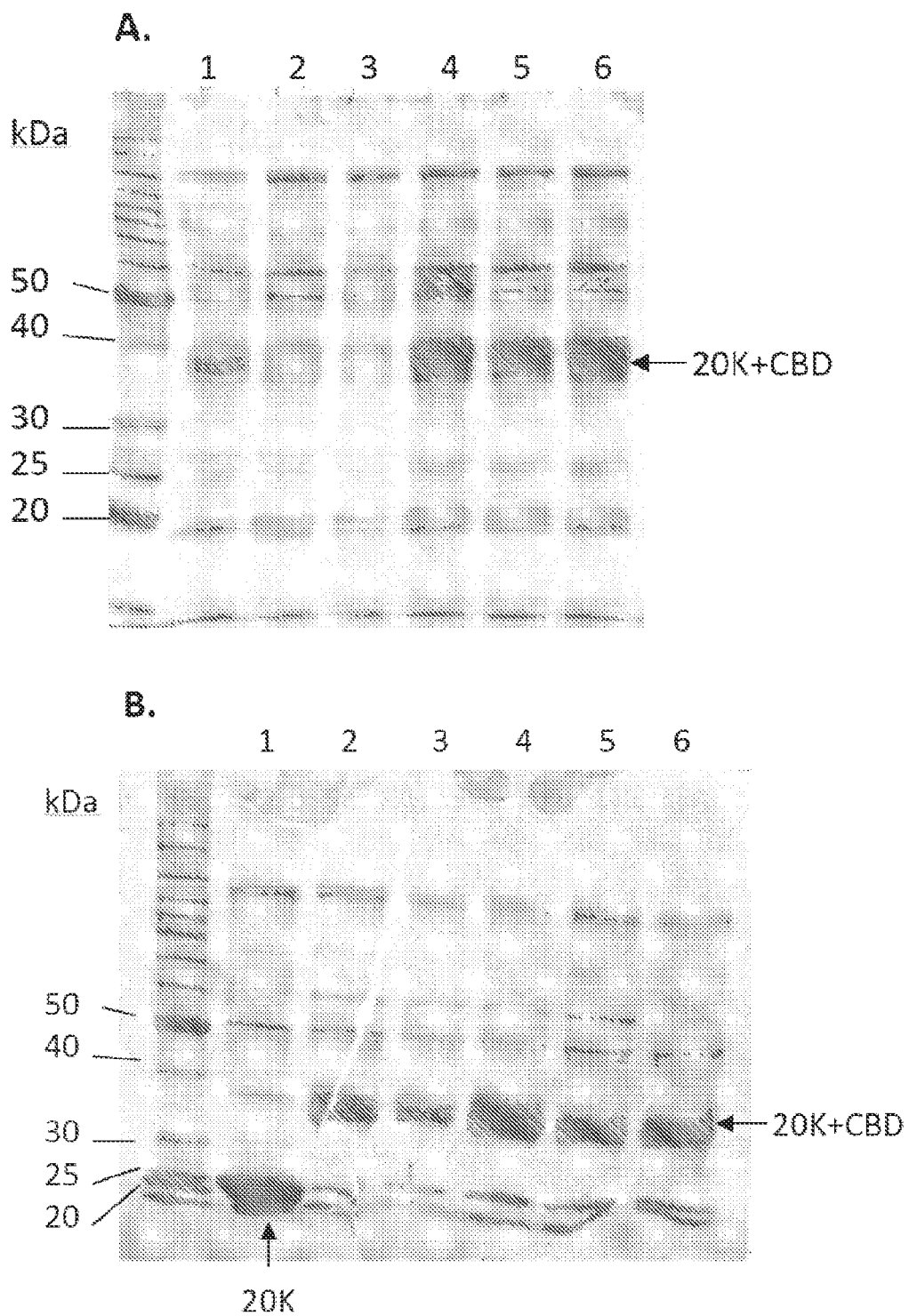
FIG. 1, panel A shows SDS-PAGE analysis of culture supernatants from shake flask cultivations of transformants producing the 20K+CBD protein. Lanes 1-3, samples deriving from the culture of a non-low-protease host of the same strain lineage as the transformation host after 3, 5 and 7 days of cultivation, respectively; 4-6, samples from 33SP #9 pALK1769 transformants #2, #6 and #7, respectively. Equal amounts of the culture supernatants were loaded on each lane.

Increased amount of full-length 20K+CBD protein was produced by several of the transformants obtained, compared to the parent strain (FIG. 1A). In the low protease host the 20K+CBD protein was not degraded after 7 days of cultivation, as was shown to be the case when a host from the same strain lineage (but not a low protease mutant) was used for production of the same protein. The clearly better stability of the 20K+CBD produced in the low protease hosts was also shown in the analysis of the fermentation cultures (FIG. 1B). In these the 20K+CBD remained in the full-length form whereas the CBD was cleaved in the non-low-protease host, resulting to a 20K protein form. According to SDS-PAGE and Western blot analysis, the amounts of TGase produced by the transformants of the low protease strains were somewhat higher than the amounts produced by A31 and A33 parents. Also, the TGase produced by the low protease strains was more stable as less of the TGase degradation products were visible in fermentations samples of these strains compared to corresponding samples produced by the parent strains.

In addition to their use as hosts for heterologous proteins the low protease strains have been successfully used as hosts for homologous *T. reesei* proteins.

Example 4. Proteases Produced and Expressed by the Low Protease Mutant Strains Identification of Proteases not Produced or being Less Abundant in the Low Protease Strains Several low protease mutant strains showed highly reduced protease activities compared to their parent (Examples 1-3). A protease inhibitor study was performed to analyse in more details which type(s) of proteases were not produced or were less abundant in the culture supernatants of the low protease strains compared to their parents. Analysis of the protease activities from the culture supernatants in the absence and presence of protease inhibitors, 0.01 mM E64, 10 mM EDTA, 0.04 mg/ml Leupeptin, 1 mM Pefabloc, 0.01 mM pepstatin and 0.02 tablets/ml of Complete™ for inhibiting cysteine, divalent cation dependent, serine/cysteine, serine, aspartyl and various classes of proteases, respectively, was performed. A reduced effect of a specific inhibitor to the protease activity indicated that the mutant strain was deficient for the type of protease that is known to be inhibited by this inhibitor. The results obtained indicated that the major protease activities in the *T. reesei* culture supernatants were due to aspartyl and serine type of proteases. These activities were clearly reduced in the culture supernatants of several mutant strains. No inhibition of the protease activity was observed in the culture supernatants of several mutants by pepstatin (at pH 5.6), Pefabloc (at pH 4.0) or leupeptin (at pH 5.6) indicating that in these strains aspartyl and/or serine proteases were largely absent. The results obtained showed that several of the low protease strains were affected in multiple proteases. In addition to the above described protease inhibitor studies, various protein separation approaches were carried out to identify from the parents the proteases which were not produced or were less abundant in the culture supernatants of the low protease mutants. These methods included SDS-polyacrylamide gel runs, native PAGE, IEF (isoelectric focusing) gel analysis and zymogram analysis using casein-based protein gels. To reduce the background of cellulases and hemicellulases and allow better identification of the remaining protein bands, the samples for gel/IEF runs and zymogram analysis were first pre-purified (pre-absorption) using cellulose matrices. According to SDS-PAGE analysis of the non-bound protein fraction several protein bands were found to be absent in the samples deriving from the protease mutants compared to the parents. However, also new bands appeared in the samples from the cultivations of protease mutants. Differences in the patterns of secreted proteins between the samples from the parents and the low protease strains were also detected in the IEF analysis. To analyse whether the differential banding identified in the SDS-PAGE and IEF gels were proteases or corresponded to e.g. incorrectly processed proteins, or proteins which in the wildtype samples have undergone proteolytic processing of specific protein domains (e.g. CBM modules), a protease activity based zymogram analysis was carried out. At least six different protein bands with proteolytic activity could be identified using this type of analysis. The zymogram pattern of the wildtype and the mutant samples revealed several differences between these samples. For some of the protease bands it was not clear whether they were absent from the low protease strains or whether they only were less abundant.

The protein bands differing in the strains were extracted from the gels and an MS/MS analysis was performed. The protein sequence data obtainable from the *Trichoderma reesei* QM6a genome version 2.0 (Trire2) at on the world wide web at genome.jgi-psf.org/Trire2/Trire2.home.html (ID numbers derived from this genome are hereafter referred to with a prefix QM_) was used in the identification of the proteases. In total eight different proteases were identified, four of which were clearly absent in one or more of the low protease strains.

To find additional proteases missing or being produced at lower levels by the low protease strains, also a nano-LC-MS analysis (Proxeon nLC2 and Orbitrab Elite, Thermo Fischer) was performed for the full set of proteins in the culture supernatants of several *T. reesei* strains, including e.g. 31UV #22. The MS data obtained was analysed using Proteome Discoverer program against the public *T. reesei* genome sequence (Trire2). In this analysis altogether 13 secreted *T. reesei* proteases were identified. Of these, at least five proteases were clearly missing or being produced in very low levels in the low protease mutant strain compared to the parent.

Expression of Endogenous Proteases in Low Protease Strains, Northern Blot and Microarray Analysis To analyse the expression levels of chosen protein encoding genes, RNA was isolated from samples collected from seven laboratory scale fermentations (parents and five low protease strain), from four time points (both logarithmic and stationary phases included) of the cultivations. The strains chosen for analysis were as follows: A31, A31SP #4, A31UV #22, A33, A33SP #9, A33UV #48 and A33UV #82. The expression of the eight proteases, previously identified from the *T. reesei* culture supernatants, was studied. The probes were prepared by PCR, basing on sequences in the public *T. reesei* database. The probes were about 600 bp in length, in each case and consisted of internal fragments of the coding sequence of the 8 respective protease genes. As a reference probe, an about 600 bp gpd1 (QM_ID119735) PCR fragment was used.

The results from the Northern blot analysis showed that expression of seven out of the eight protease encoding genes was affected (no or very low expression levels) in all the mutants tested. Further transcriptional profiling of one of the low protease strains was performed using oligonucleotide microarray (Roche NimbleGen Inc., USA). Mycelia was harvested from three time points from three replicate laboratory scale fermentations of strains 33SP #9 and the wildtype strain A33 and total RNA was extracted from the samples. The cDNA synthesis, labeling, hybridization, microarray scanning and signal detection of the samples was carried out according to the instruction by Roche Nimble-Gen. Custom microarray slides containing 60-mer probes designed based on the public *T. reesei* genome sequence from on the world wide web at genome.jgi-psf.org/Trire2/Trire2.home.html were used. The microarray data was analysed for differentially expressed protease genes with a statistical significance cut-off at $P<0.01$ by using the R packages Oligo, Limma and Mfuzz (on the world wide web at bioconductor.org/).

Based on the microarray results, the expression of several protease genes was down-regulated in the low protease mutant 33SP #9. In addition to the previously identified proteases, altogether at least 18 additional proteases with clearly lowered expression were discovered.

The results obtained from the protein and RNA analysis are summarised in Table 2.

TABLE 2

Proteases being absent or less abundant in the culture supernatants and/or having lower expression level in the low protease mutants compared to their parents. The proteases were grouped according to the peptide database MEROPS (http://merops.sanger.ac.uk/). No, number of individual proteases belonging to the group.

| Protease Group (MEROPS) | No | Families represented (MEROPS) |
|---|---|---|
| Metallo Peptidase (M) | 11 | M1, M3, M6, M14, M18, M28 |
| Serine Peptidase (S) | 7 | S1, S28, S8/S53 |
| Aspartic Peptidase (A) | 5 | A1 |
| Glutamic Peptidase (G) | 2 | G1 |
| Mixed peptidase (P) | 1 | P1 |

Example 5. Genome Sequencing and Comparison

Genomic DNA was isolated from freeze-dried and ground mycelium of selected low protease strains with E.Z.N.A® SP Fungal DNA Mini Kit (Omega Bio-Tek Inc., USA) according to the manufacturer's instructions. The genomes were sequenced using the Illumina (Solexa) method and the draft genomes were assembled against the public Trichoderma reesei RutC-30 genome version 1.0 (TrireRUTC30_1) available from on the world wide web at genome.jgi.doe.gov/TrireRUTC30_1/TrireRUTC30_1.home.html. The ID numbers derived from this genome are hereinafter referred to with a prefix Rut_. All differences in genomes against the public genome were analysed and the mutation profiles compared between the low protease strains. According to the genome sequencing, three individual low protease strains had mutations in the coding region of a predicted gene Rut_ID85889 (SEQ ID NO: 4-6). The corresponding gene in strain 33SP #9 (SEQ ID NO: 7) contained an insertion of two nucleotides inside the coding region of the predicted gene 840 bp downstream of the start codon. In strain 31UV #22 (SEQ ID NO: 9), the gene had a deletion of one nucleotide from the coding region 968 bp downstream of the start codon. According to the annotation of the gene Rut_ID85889, both the insertion and the deletion described above result in a frame-shift and formation of an early stop codon downstream of the mutations. The mutation in 31SP #4 (SEQ ID NO: 8) is a single point mutation 1224 bp downstream of the start codon resulting in the formation of an early stop codon.

For strain A21, the corresponding full-length gene Rut_ID85889 was PCR amplified from the A21 genomic DNA and sequenced directly from the PCR fragment using the ABI PRISM® 310 Genetic Analyzer by Applied Biosystems (Thermo Fisher Scientific Inc., USA). The nucleotide sequence of the corresponding gene in strain A21 (SEQ ID NO: 10) was found to contain a single point mutation 952 bp downstream of the start codon resulting in the formation of an early stop codon.

All of the mutations described above disrupt the full-length open reading frame of the Rut_ID85889 gene and the mutated genes, when translated, encode truncated protein products. The putative Rut_ID85889 was named as protease expression affecting gene, pea1. The pea1 gene in TrireRUTC30_1 genome is 2749 bp long including the stop codon and contains two introns, a 191 bp long intron 1029 bp downstream of the start codon and a 80 bp long intron 1402 bp downstream of the start codon. The annotation of the RutC-30 pea1 gene differs from the annotation of the gene in the corresponding genome region in the Trire2 genome, QM_ID123125 (SEQ ID NO: 1-3). The sequence of the hypothetical QM6a gene QM_ID123125 corresponds to the C-terminal nucleotide sequence of the Rut_ID85889. QM_ID123125 is 961 bp long and has a 42 bp intron 383 bp downstream of the start site (FIG. 2). Because of the discrepancies in the annotation of the Rut_ID85889 and QM_ID123125 genes, cDNA synthesis and sequencing of the pea1 cDNA was performed from a QM6a RNA sample (Example 6).

Example 6. The Pea1 Gene Annotation and Sequence Comparison

In order to confirm the nucleotide sequence of the pea1 gene and locus, a 4.7 kb fragment was PCR cloned using QM6a genomic DNA as template. The fragment was amplified using primers S-ppea1 (sense primer CGTTGGCTCGAGGCAACTGC (SEQ ID NO: 19)) and AS-3UTRout16 (anti-sense primer TGTCATCATGTCTTT-ATTCA (SEQ ID NO: 20)). The PCR reaction mixtures contained 1×Phusion HF buffer (Thermo Fisher Scientific Inc., USA), 0.23 mM dNTPs, 1.3 µM each primer and 1.3 units of Phusion High-Fidelity DNA polymerase (Thermo Fisher Scientific Inc., USA) per 50 µl reaction volume. The conditions for the PCR reactions were the following: 1 min initial denaturation at 98° C., followed by 29 cycles of 10 s at 98° C., 30 s annealing at 63° C., 1 min extension at 72° C. and a final extension at 72° C. for 5 min. The resulting 4.7 kb PCR fragment was cut from agarose gel and isolated using the QIAquick Gel Extraction Kit (Qiagen GmbH, Germany). The purified fragment was cloned into the PCR®4 Blunt-TOPO® Vector using the Zero Blunt® TOPO® PCR Cloning Kit (Thermo Fisher Scientific Inc., USA). The resulting plasmid was named pALK3535 and the Escherichia coli (TOP10) strain including the plasmid, RF11697, was deposited to the DSM collection under the accession number DSM32007. The PCR fragment in pALK3535 contains the full-length RutC-30 ID: 85889 gene and 1140 bp upstream and 821 bp downstream sequences (SEQ ID NO: 11). This fragment was sequenced using the ABI PRISM® 310 technology as described in Example 5. The sequence was identical to the nucleotide sequence in the public Trire2 and TrireRUTC30-1 genomes.

For the cDNA analysis, total RNA was isolated from deep frozen QM6a mycelium grown in cellulose inducing medium (Joutsjoki et al., 1993) with RNeasy® Plant Mini Kit (Qiagen GmbH, Germany) and mRNA translation to cDNA from the isolated RNA was done with Transcriptor First Strand cDNA Synthesis Kit (Roche Diagnostics GmbH, Germany) according to the manufacturer's instructions. The cDNA was PCR amplified using specific primers S-5UTR26 (sense primer CCAGAACAGCTCCGTCCTGG (SEQ ID NO: 21)) and AS-3UTRout16. The PCR reaction mixtures contained 1×Q5 Reaction buffer (New England Biolabs Inc., USA), 0.2 mM dNTPs, 0.5 µM each primer and 2 units of Q5® High-Fidelity DNA polymerase (New England Biolabs Inc., USA) and approximately 2 µl of cDNA per 50 µl reaction volume. The conditions for the PCR reactions were the following: 1 min initial denaturation at 98° C., followed by 31 cycles of 10 s at 98° C., 30 s annealing at 63° C., 1 min 20 s extension at 72° C. and a final extension at 72° C. for 4 min. The resulting 4.1 kb PCR fragment was cut and isolated from agarose gel. The purified fragment was cloned into the PCR®4 Blunt-TOPO® Vector using the Zero Blunt® TOPO® PCR Cloning Kit (Thermo Fisher Scientific Inc., USA). The resulting plasmid was named pALK3536 and the *Escherichia coli* (TOP10) strain including the plasmid, RF 1698, was deposited to the DSM collection under the accession number DSM32008. The cDNA in pALK3536 includes 654 bps of the 5'UTR (untranslated region) and 821 bps of the 3'UTR (SEQ ID NO: 12). The fragment was sequenced and the sequence was compared to the corresponding pea1 gene cloned from QM6a (SEQ ID NO: 11). The results showed that the pea1 gene start and stop sites and the second intron were as predicted for the Rut_ID85889, but contrary to the Rut_ID85889 annotation, the first intron of pea1 is 62 bp long and located 1158 bp downstream of the start codon (FIG. 3).

The nucleotide sequence of the full-length pea 1 gene (SEQ ID NO: 11, nucleotides 1141-3889) and the deduced amino acid sequence (SEQ ID NO: 13) were used to search similar sequences from public sources. Searches were made using the FASTA search tools at the EMBL-EBI website by using the ENA sequence database for the nucleotide search (on the world wide web at ebi.ac.uk/Tools/sss/fasta/nucleotide.html) and the UniProt Knowledgebase for the protein search (on the world wide web at ebi.ac.uk/Tools/sss/fasta/). The searches were made using the default values. In addition, searches were done from available genome sequences of the strains belonging to *Trichoderma* genus. The *Trichoderma* genome sequences used in the searches were as follows: *Trichoderma citrinoviride* (on the world wide web at genome.jgi.doe.gov/Trici1/Trici1.home.html), *Trichoderma longibrachiatum* (on the world wide web at genome.jgi.doe.gov/Trilo1/Trilo1.home.html), *Trichoderma virens* (on the world wide web at genome.jgi-psf.org/TriviGv29_8_2/TriviGv29_8_2.home.html), *Trichoderma harzianum* (on the world wide web at genome.jgi.doe.gov/Triha1/Triha1.home.html), *Trichoderma asperellum* (on the world wide web at genome.jgi.doe.gov/Triasl/Triasl.home.html), *Trichoderma atroviride* (on the world wide web at genome.jgi.doe.gov/Triat2/Triat2.home.html). The identity values (%) to the most similar sequences identified from the searches were determined using the Pairwise Sequence Alignment tool at the EMBL-EBI website (for nucleotide sequences: on the world wide web at ebi.ac.uk/Tools/psa/emboss_needle/nucleotide.html; for protein sequences: on the world wide web at ebi.ac.uk/Tools/psa/emboss_needle/by using the default values (Gap open: 10 and Gap extend: 0.5). The results are shown in Tables 3A and 3B. The highest identities were to the homologous sequences from other *Trichoderma* species. The highest percentage of identity to a non-*Trichoderma* sequence was obtained with a hypothetical *Ophiocordyceps sinensis* OCS_06053 sequence, with 59.6% identity on the nucleotide level and 58.3% identity on the protein level.

The Pea1 amino acid sequence was aligned with the homologous sequences obtained from other *Trichoderma* species and sequences having over 50% identity to the Pea1 protein, according to the FASTA protein search results. A highly conserved region was detected from the alignment. One sequence per genus was selected from the search results for further analysis. The identity between the *Trichoderma* species in the highly conserved Pea1 region, from Arg402 to Pro533 (132 residues), is at least 97% and similarity 99% whereas this region had at least 90% identity and 96% similarity to the sequences deriving from other filamentous fungal species, selected from the FASTA search results (Table 3C). Corresponding sequence regions were used in determining the degree of identity as shown in FIG. 4. Taxonomically (on the world wide web at mycobank.org), all of the selected sequences originate from species belonging to the Sordariomycetes, subclass Hypocreomycetidae and order Hypocreales, indicating that this region is highly conserved in especially in Hypocreales. High values, 90.2% identity and 96.2% similarity were also found to e.g. *Scedosporium apiospermum* (SAPIO_CDS0483) sequence. The *S. apiospermum* species also belongs to the subclass Hypocreomycetidae, order Microascales.

The highly conserved Pea1 region contains a predicted pfam domain Clr5 (PF14420). The Clr5 domain is located at position Ala410 to Lys462 (53 residues) in Pea1 sequence. The Clr5 domain has been shown to be involved in silencing in fission yeast (Hansen, K. R., Hazan, I., Sreenath, S., Watt, S., Verhein-Hansen, J., Bähler, J., Martienssen R. A., Partridge, J. F., Cohen, A., Thon, G. 2011. H3K9me-independent gene silencing in fission yeast heterochromatin by Clr5 and histone deacetylases. PLOS Genetics 7, el 001268).

TABLE 3A

The identity values (%) obtained from Pairwise Sequence Alignment of the nucleotide sequence of full-length pea1 gene (SEQ ID NO: 11, nucleotides 1141-3889). EMBOSS Needle (EMBL-EBI, EMBOSS-Needle-Pairwise Sequence Alignment, Matrix DNAfull, Gap open 10, gap extend 0.5) at www.ebi.ac.uk/Tools/psa/emboss_needle/nucleotide.html was used for determining the degree of identity.

| Name | Identity |
|---|---|
| Rut_ID85889 | 100 |
| Trichoderma citrinoviride ID:7704 (v1.0) | 90.0 |
| Trichoderma longibrachiatum ID:60713 (v1.0) | 89.7 |
| Trichoderma virens ID:58331 (v2.0) | 81.2 |
| Trichoderma harzianum ID:235354 (v1.0) | 80.6 |
| Trichoderma asperellum ID: 84188 (v1.0) | 76.9 |
| Trichoderma atroviride ID:280821 (v2.0) | 76.7 |
| Ophiocordyceps sinensis OCS_06053 | 59.6 |

TABLE 3B

The identity and similarity values (%) obtained from Pairwise Sequence Alignment of the full-length Pea1 amino acid sequence (SEQ ID NO: 13, amino acids 1-868). EMBOSS Needle (EMBL-EBI, EMBOSS-Needle-Pairwise Sequence Alignment, Matrix BLOSUM62, Gap open 10, gap extend 0.5) at www.ebi.ac.uk/Tools/psa/emboss_needle/ was used for determining the degree of identity and similarity.

| Name | Identity | Similarity |
|---|---|---|
| Rut_ID85889 | 95.0 | 95.0 |
| Trichoderma citrinoviride ID: 7704 (v1.0) | 96.0 | 96.0 |
| Trichoderma longibrachiatum ID: 60713 (v1.0) | 91.5 | 93.9 |
| Trichoderma harzianum ID: 235354 (v1.0) | 88.3 | 93.3 |
| Trichoderma virens ID: 58331 (v2.0) | 85.9 | 90.7 |
| Trichoderma atroviride ID: 280821 (v2.0) | 83.0 | 89.6 |
| Trichoderma asperellum ID: 84188 (v1.0) | 82.9 | 90.1 |
| Ophiocordyceps sinensis OCS_06053 | 58.3 | 69.9 |

TABLE 3C

The identity and similarity values (%) obtained from
Pairwise Sequence Alignment of
the amino acid sequence of the Pea1 highly
conserved region (SEQ ID NO: 13,
amino acids 402-533) with the corresponding
region in other sequences. EMBOSS
Needle (EMBL-EBI, EMBOSS-Needle-
Pairwise Sequence Alignment, Matrix
BLOSUM62, Gap open 10, gap extend 0.5) at
www.ebi.ac.uk/Tools/psa/emboss_needle/
was used for determining the degree of
identity and similarity.

| Name | Identity | Similarity |
|---|---|---|
| Trichoderma citrinoviride ID: 7704 (v1.0) | 100 | 100 |
| Trichoderma longibrachiatum ID: 60713 (v1.0) | 100 | 100 |
| Trichoderma atroviride ID: 280821 (v2.0) | 98.5 | 100 |
| Trichoderma asperellum ID: 84188 (v1.0) | 98.5 | 100 |
| Trichoderma harzianum ID: 235354 (v1.0) | 97.0 | 100 |
| Trichoderma virens ID: 58331 (v2.0) | 97.0 | 99.2 |
| Fusarium oxysporum FOVG_08585 | 95.5 | 97.7 |
| Gibberella fujikuroi FFUJ_12153 | 95.5 | 97.7 |
| Stachybotrys chartarum S40293_07230 | 94.7 | 100 |
| Claviceps purpurea CPUR_05697 | 92.4 | 97.0 |
| Ophiocordyceps sinensis OCS_06053 | 91.7 | 98.5 |
| Nectria haematococca NECHADRAFT_85885 | 91.7 | 98.5 |
| Metarhizium acridum MAC_08836 | 91.7 | 97.7 |
| Villosiclava virens UV8b_6262 | 91.7 | 96.2 |
| Acremonium chrysogenum ACRE_079620 | 90.2 | 97.0 |

Example 7. Construction of Cassettes for Deleting the Full-Length and Partial Pea1 Gene from *T. reesei*

Altogether three deletion cassettes were planned and constructed, pALK4104 (FIG. 5A), pALK4106 (FIG. 5B) and pALK4107 (FIG. 6). The pALK4104 and pALK4107 were constructed for deleting the full-length pea1 gene and pALK4106 for partial pea1 deletion (truncation) from the genomes of *T. reesei* host strains. The length of the deduced amino acid sequence of the truncated Pea1 encoded by pALK4106 (297 amino acids) is in the range of the deduced Pea1 mutant protein in strains A21, 31SP #4, 33SP #9 and 31UV #22 (FIG. 7). All the cassettes contain a selection marker surrounded by flanking regions for targeting the cassette into an intended location in the *T. reesei* genome. For details, see below.

The pUC19 vector was used as a backbone in the plasmid constructions. The common molecular biology methods were used in enzyme treatments of DNA, PCR (polymerase chain reaction), *E. coli* transformations and isolation of plasmid DNA and DNA fragments for ligations and transformations. A genomic DNA preparation isolated from QM6a was used as a template in all the PCR reactions.

The pALK4104 deletion cassette contains:
A pea1 5'-flanking region for targeting the cassette into the pea1 locus for gene replacement, together with the 3'-flanking region (see below). The 5'-flanking region is the 1578 bp SalI-XbaI genomic fragment, the XbaI site locating 531 bp upstream from the pea1 gene start (first Met encoding ATG). The fragment was synthesized by PCR.
Synthetic amdS (acetamidase) encoding the acetamidase selection marker. A cDNA of the native *Aspergillus nidulans* amdS gene with additional modifications (de-letion of chosen restriction sites) was used in the deletion cassette. The gene encodes the original AmdS amino acid sequence.
A pea1 3'-flanking region for targeting the cassette into the pea1 locus for gene replacement, together with the 5'-flanking region (see above). The 3'-flanking region is the 2676 bp KpnI-XbaI genomic fragment, the KpnI site locating 60 bp downstream from the pea1 gene's stop codon (TAG). This fragment was synthesized by PCR. It includes all the genes annotated into this region, according to both the public Trire2 or TrireRUTC30-1 genome sequences. The XbaI site at the 3'-end of the fragment is not available in the final construction due to filling in reaction (by Klenow fragment) done when constructing the plasmid.

The pALK4106 deletion cassette contains:
A pea1 5'-flanking region for targeting the cassette into the pea1 locus/gene for gene replacement, together with the 3'-flanking region (see below). The 5'-flanking region contains a partial pea1 promoter, starting immediately after the XbaI site in the promoter region (526 bps before the gene start codon, the XbaI site is not included) and ending immediately prior to the internal EcoRI site in the pea1 gene (892 bps from the gene start, the EcoRI site is not included). This fragment was synthesized by PCR. It encodes a truncated 297 amino acids Pea1 product (SEQ ID NO: 18).
Synthetic amdS (acetamidase) encoding the acetamidase selection marker. A cDNA of the native *Aspergillus nidulans* amdS gene with additional modifications (de-letion of chosen restriction sites) was used in the deletion cassette. The gene encodes the original AmdS amino acid sequence.
A pea1 3'-flanking region for targeting the cassette into the pea1 locus for gene replacement, together with the 5'-flanking region (see above) was the same as the 3'-flanking fragment used in pALK4104 (see above).

The pALK4107 deletion cassette contains the identical 5'- and 3'-flanking regions to those included in pALK4104. The syn-amdS gene in pALK4104 (XbaI digestion of pALK4104, fill-in by Klenow) was replaced by the ble selection marker gene (with a promoter and terminator originating from *Aspergillus nidulans*) deriving from pAN8-1 (3313 bp BglII-XbaI fragment, the ends filled in using Klenow) and coding for phleomycin resistance (for more details, see the description of FIG. 6). The pALK4107 deletion cassette was used to delete the full-length pea1 gene from such *T. reesei* strains that already include the amdS marker gene, due to e.g. previous transformation of a gene expression cassette into the strain.

The 6756 bp pALK4104 and 6595 bp pALK4106 deletion cassettes for the *T. reesei* transformations were cleaved from the vector backbones by PstI-EcoRI digestions, were isolated from agarose gels and transformed (as described in Example 3) to protoplasts of a selection of *T. reesei* host strains, namely QM6a, RutC-30 and A33. The transformants were selected on acetamide plates and purified via single spores prior to streaking them on PD slants.

The transformations done using the pALK4107 deletion cassette are described in Example 9.

Example 8. Characterisation of the pALK4104 and pALK4106 Transformant

The protease production of a selection of QM6a, RutC-30 and A33 transformants were analysed by growing the strains on skim milk plates. The host strains were used as controls.

Transformants which produced lower amounts of protease in the plate assay compared to their host were found from each set of transformants (Table 4). The pea1 locus from the genomes of a selection of these transformants was analysed by Southern blot method. The pea1 gene was found to be deleted from the genomes of all the low protease pALK4104 transformants and truncated in the genomes of all the low protease pALK4106 transformants analysed by Southern blot. Strains with successful replacement of the pea1 gene with one copy (single-copy replacement) of the syn-amdS selection marker (in pALK4104 transformants) and replacement of the partial pea1 gene with the syn-amdS (in pALK4106 transformants, leading to truncation of the pea1 gene in these strains) were found from each set of transformants (Table 4).

TABLE 4

Summary on the pALK4104 (deletion of the full length pea1) and pALK4106 (partial deletion/truncation of pea1) transformants analysed on skim milk plates and by Southern blot. Amounts of low protease strains (reduced halo compared to host) and single copy (correct replacement) strains of all analysed transformants are shown.

| Host strain | Deletion cassette transformed | Low protease transformants (skim milk plate assay) | Single-copy replacement strains (Southern blot analysis) |
|---|---|---|---|
| QM6a | pALK4104 | 4/18 | 3/4 |
| RutC-30 | " | 11/33 | 6/6 |
| A33 | " | 14/31 | 6/6 |
| QM6a | pALK4106 | 4/18 | 4/4 |
| RutC-30 | " | 10/29 | 4/6 |
| A33 | " | 12/30 | 6/6 |

Three single-copy replacement strains were chosen from each transformation and stored to Roal culture collection. The low protease phenotype of these strains is further analysed by cultivating the transformants and their hosts (for comparison) in laboratory scale bioreactors. A cellulase inducing complex medium is used in the cultivations. The results are expected to correspond to those previously obtained from the cultivations of the low protease mutants (Example 2): the transformants with pea1 gene deletion and truncation produce lower protease activities compared to their hosts. The genetically modified strains with pea1 deletion or truncation are expected to produce similar or better amounts of secreted proteins and/or cellulase activities compared to their hosts as only the pea1 locus has been modified in these strains.

Example 9. Deletion of Pea1 from Strains Overproducing a Cellulase and a Laccase Enzyme The deletion cassette pALK4107 for the *T. reesei* transformations was cleaved from the vector backbone by PstI-EcoRI digestion, was isolated from an agarose gel and transformed to protoplasts of two previously constructed strains producing recombinant enzymes. The strains transformed were as follows: RF5969 producing the 20K+CBD (expression from the pALK1769 cassette, Example 2) and RF5597 producing a laccase TaLcc1, originating from *Thielavia arenaria* (expression from the pALK1667 cassette, U.S. Pat. No. 7,927,849). In both cases, the gene encoding the recombinant enzyme was expressed using the strong native *T. reesei* cbh1 (cel7A) promoter. The transformation of the pALK4107 deletion cassette to RF5969 and RF5597 protoplasts was done as described in Example 3 but using phleomycin selection for screening of the transformants (Harkki et al., 1991). After purification via single spores, the transformants were streaked on PD slants.

The protease production of the transformants was analysed using skim milk plates (as explained in Example 1) using the transformation hosts as controls. Transformants producing lower amounts of proteases compared to their host were obtained from both the transformations.

The RF5969 transformants can be further tested on cellulase indicator plates containing e.g. Azo-CM-cellulose (Megazyme) and the RF5597 transformants on laccase indicator plates containing ABTS (Roche) to confirm the 20K+CBD and laccase production, respectively, of these strains. The transformation hosts are used as controls in the plate assays.

The chosen transformants with low protease production and confirmed production of the recombinant enzyme can be cultivated in shake flasks and/or bioreactors using cellulase inducing conditions. The lowered protease production compared to the hosts can be shown from the culture supernatants by activity assay(s). Increased production and better stability of the recombinant enzymes in the culture supernatant samples of the low protease strains compared to the hosts can be confirmed by known methods.

Example 10. Characterisation of the Production Strains with Pea1 Deletion

A set of RF5597 and RF5969 transformants which produced lower amounts of proteases compared to their hosts in the plate assay (Example 9) were further characterised. A Southern blot analysis confirmed that in all these strains the pea1 gene was replaced with the selection marker. The hosts and chosen transformants with confirmed deletion of the pea1 gene were cultivated in 0.5 L bioreactors using cellulase inducing conditions. The protease activity and other relevant enzyme activities were measured from the culture supernatants. The protease activity (HUT) was measured using haemoglobin substrate (as in Example 2). Cellulase activity (NCU, "neutral cellulase unit") was analysed from RF5969 and its transformants. Carboxymethylcellulose (Sigma, low viscosity CMC) was used as a substrate in this analysis. The enzyme reaction was conducted at pH 7.0, 50° C. for 10 minutes and DNS method was used to measure the liberated reducing ends. As a soluble substrate was used in the analysis, there are no major differences in the specific activities between the 20K cellulase forms with and without the binding domain (CBD/CBM). The laccase activity was measured from RF5597 and its transformants at pH 4.5 using ABTS as a substrate (Niku-Paavola, M. L.; Karhunen, E.; Salola, P.; Raunio, V. (1988): Ligninolytic enzymes of the white-rot fungus *Phlebia radiata*. In *Biochem. J.* 254 (3), pp. 877-883).

The RF5597 and RF5969 transformants with pea1 deletion produced clearly lower protease (HUT) activity compared to their hosts which have the wild type pea1 gene. The protease activities from the culture supernatants of the RF5597 transformants were, in average, only about 50% and of the RF5969 transformants, in average, only about 25% of the activity measured from the hosts culture supernatants. The cellulase (NCU) activity in the culture supernatants of the RF5969 transformants was increased up to 37% compared to the activity measured from the RF5969 cultivation. However, no increases in the laccase activities produced by the RF5597 transformants, compared to RF5597, were detected. To analyse the integrity and stability of the recombinant enzyme products, samples of the culture supernatants were run into SDS-PAGE gel. The TaLcc1 laccase protein band was similar (in mass and amount) from RF5597 and its transformants. However, there were clear differences in the recombinant cellulase protein produced by RF5969 and its transformants with pea1 deletion (FIG. 8). The major protein in the culture supernatant of RF5969 was not the full-length 20K+CBD but the 20K core form from which the CBD had been cleaved off. Only very minor amount of the full-length 20K+CBD was detectable in the gel. The RF5969 transformants with pea1 deletion produced mainly the full-length 20K+CBD and only very low relative amount of the 20K form. This result confirms that the pea1 deletion strains were able to produce higher amounts of the recombinant product and that the recombinant enzyme in the culture supernatants of the pea1 deletion strains was more stable than it was in the culture supernatant of the host.

The stabilities of the TaLcc1 products were further studied by incubating samples of culture supernatants at 30 and 50° C. (at pH 4) for up to three days. After the incubations samples were run into SDS-PAGE gel. The recombinant TaLcc1 was very stable in all the samples. However, after 3 days of incubation at 50° C. the TaLcc1 protein band was clearly more degraded in the culture supernatant of the host (RF5597) compared to the supernatants of the RF5597 Δpea1 transformants. This result further confirms the increased stability of the products obtained from the strains with a non-functional pea1 gene.

Similar results were obtained from RF5597 and RF5969 transformants from which the pea1 gene was deleted using the pALK4116 deletion cassette. In this cassette, the ble marker gene in pALK4107 was replaced by the hph marker gene encoding resistance for hygromycin B (Mach, R. L.; Schindler, M.; Kubicek, C. P. (1994): Transformation of *Trichoderma reesei* based on hygromycin B resistance using homologous expression signals. In *Curr. Genet.* 25 (6), pp. 567-570).

Example 11. Disruption of Pea1 Homologue from *Fusarium* Species

Many fungal species contain a homologue of the *T. reesei* pea1 gene, as described in Example 6. The encoded full-length *T. reesei* Pea1 homologues from *Fusarium oxysporum*, e.g. FOVG_08585 and FOZG_02804 (amino acids 1-887) have identity values of 57.2 and 57.1% and similarity values of 68.8 and 68.7%, respectively, to the full-length *T. reesei* Pea1 (SEQ ID NO:13, amino acids 1-868; alignment done using EMBL-EBI, EMBOSS-Needle-Pairwise Sequence Alignment, Matrix BLOSUM62, Gap open 10, gap extend 0.5 at www.ebi.ac.uk/Tools/psa/emboss_needle/). The corresponding identity and similarity values between the *T. reesei* Pea1 and the full-length *Fusarium* (*Gibberella*) *fujikuroi* Pea1 homologue (e.g. FFUJ_12153, amino acids 1-882) are 57.5 and 68.9%, respectively. The deduced amino acid sequences of the full-length Pea1 homologues from the *F. oxysporum* and *F. fujikuroi* are highly similar with each other, the identity and similarity values between the above full-length amino acid sequences being 96.6 and 97.4%, respectively.

To confirm that the role of the Pea1 homologues in other fungi is similar to that in *T. reesei*, a split marker approach (FIG. 9) was designed to disrupt the pea1 homologues from two *Fusarium* species, *F. oxysporum* and *F. fujikuroi*. The ~3 kb split marker fragment 1 contained a promoter region of the *F. oxysporum* Fo47 pea1 gene (1468 bp, nts from −1483 to −16 from the start codon, to target the fragment to pea1 locus) and the 5' half of the hph marker gene (from nucleotide 1 to 615 and the *Asper*-gillus gpdA promoter). The ~3 kb split marker fragment 2 contained the 3' half of the hph selection marker (from nucleotide 166 to 1026 and the *Aspergillus* trpC terminator region) and partial *F. oxysporum* pea1 gene and its terminator region (1358 bp; starting from the nt 1667 of the gene and ending 380 nts after the pea1 stop codon, to target the fragment to pea1 locus). Thus, both the split marker fragments included the same 450 bp middle part of the hph gene. When the two split marker fragments are transformed into the same host, they recombine with the corresponding pea1 regions in the genome. When they also recombine with each other at the common middle part region of hph, the selection marker becomes functional. Using the designed approach, a functional selection marker in the transformants was expected to be linked to a disrupted pea1 gene at high frequency.

As the sequences of the *F. oxysporum* and *F. fujikuroi* pea1 genes and their 5'- and 3'-regions are highly similar (but not identical) with each other, the same split marker fragments were used for disruption of the pea1 genes from both the species.

Example 12. Transformation of *Fusarium oxysporum* and *F. fujikuroi* and Analysis of the Transformants

*Fusarium oxysporum* Fo47 and *F. fujikuroi* IM158289 strains were transformed using the designed and synthesized split marker fragments (Example 11). The method described in Wiemann et al. (PLos Pathog. 2013; 9(6):e1003475 and refer-ences within) was used in the fungal transformations. Altogether 96 *F. oxysporum* and 46 *F. fujikuroi* transformants were obtained. The targeted DNA modification (disruption of the pea1 homologue) was analysed from 20 *F. oxysporum* and 10 *F. fujikuroi* transformants using diagnostic PCR. The primers in the PCR reaction were designed from the end of the pea1 5'-flank in the split marker fragment 1 (from the pea1 promoter, nucleotides from −38 to −21 from the ATG) and the beginning of the 3'-flank in the split marker fragment 2 (nucleotides 1716-1695 of the *F. oxysporum* pea1 gene). The designed diagnostic PCR reaction results to a 1.6 kb fragment from the native (complete) *Fusarium* pea1 gene whereas the length of the product from a disrupted gene is 2.5 kb.

From most of the transformants a sole 2.5 kb PCR product was obtained indicating a successful integration of the full-length marker into the pea1 locus and disruption of the pea1 gene. The pea1 flanking fragments from *F. oxysporum* could be used for disruption of the pea1 from both the *Fusarium* species.

A selection of transformants were purified which were shown by diagnostic PCR to contain a disrupted pea1 gene. Four transformants from each species and their parent strains were cultivated in shake flasks on casein-based induction medium (FusP) with and without supplementation of 0.5 g/L of CasAmino acids. The FusP medium contained (per 1000 ml): 20 ml of 50×FusP salts (26 g/L KCl, 82 g/L $K_2HPO_4$, 43 g/L $NaH_2PO_4xH_2O$, pH adjusted to 7.5 using NaOH), 10 g/L glucose, 5 g/L casein (Sigma C8654), 2 ml of 1 M $MgSO_4$, 1 ml of 1000×trace elements solution (contains, per 100 ml: 2.2 g $ZnSO_4x7H_2O$, 1.1 g $H_3BO_3$, 0.5 g $MnCl_2x4H_2O$, 0.5 g $FeSO_4x7H_2O$, 0.17 g $CoCl_2x6H_2O$, 0.16 g $CuSO_4x5H_2O$, 0.15 g $Na_2MoO_4x2H_2O$, 5.0 g $Na_2EDTAx2H_2O$, pH adjusted to 6.5 using KOH). Interestingly, the transformants with the disrupted pea1 gene showed hardly any growth on the medium which was not supplemented with the CasAmino acids, indicating that these strains were unable to use casein as a nitrogen source. All the strains, however, grew well in the medium supplemented with the CasAmino acids. Samples were taken from these cultures after 6 days of cultivation at 25° C. Extracellular proteolytic activities were measured from the culture supernatants based on a procedure described by Holm (Holm K. A. 1980. Automated colorimetric determination of acid proteinase activity in fermentation samples using a trinitrobenzenesulphonic acid reagent. Analyst. 105(1246): 18-24).

The protease activities determined from the culture supernatants of all the eight transformants with disrupted pea1 gene were very low compared to the activities from the culture supernatants of the parent strains (FIG. 10). The protease activity in the culture supernatants of the *F. fujikuroi* transformants was about 10-fold lower than that in the culture supernatant of the parent strain. The protease activity measured from the culture supernatants of the *F. oxysporum* transformants was about 40-fold lower than that from the parent strain.

The disruption of the pea1 homologue from *Fusarium* species was successful with the method used. The *Fusarium* transformants with disrupted pea1 show a distinct protease-deficient phenotype, like that of *Trichoderma* strains with non-functional pea1 gene.

The results show that the *Trichoderma* reeseilow protease strains lacking functional pea1 give benefits when used as hosts for production of proteins, and especially protease sensitive proteins. At least similar, or in several cases even higher production yields of proteins can be reached with these strains compared to the yields obtained when the parents of these strains are used as hosts for the same enzyme products. In addition, the enzyme products obtained from the strains lacking a functional pea1 are more stable compared to the corresponding products from the parents of these strains.

The pea1 homologues can be found in the genome of several fungal species. Our results show that disruption of the pea1 homologues from species other than *T. reesei* lead to similar protease deficient phenotypes as shown for the *T. reesei* strains which lack a functional pea1. The results confirm the role of pea1 and its homologues as important factors for affecting protease expression. Significant improvements in protein yields and stability of products can be achieved by disrupting the pea1 from the production strains of different species.

The foregoing description has provided, by way of non-limiting examples of particular implementations and embodiments of the invention, a full and informative description of the best mode presently contemplated by the inventors for carrying out the invention. It is however clear to a person skilled in the art that the invention is not restricted to details of the embodiments presented in the foregoing, but that it can be implemented in other embodiments using equivalent means or in different combinations of embodiments without deviating from the characteristics of the invention.

Furthermore, some of the features of the afore-disclosed embodiments of this invention may be used to advantage without the corresponding use of other features. As such, the foregoing description shall be considered as merely illustrative of the principles of the present invention, and not in limitation thereof. Hence, the scope of the invention is only restricted by the appended patent claims.

The invention claimed is:

1. A protein preparation comprising spent culture broth from production of a heterologous recombinant protein of interest in a host cell having at least one inactivated chromosomal gene wherein:
the at least one inactivated chromosomal gene comprises a nucleic acid sequence encoding a polypeptide comprising a sequence having at least 90% sequence identity with the amino acids 402-533 of SEQ ID NO: 13;
the at least one inactivated chromosomal gene is inactivated by disruption;
and the host cell has reduced protease activity on the heterologous recombinant protein of interest in the host cell compared to protease activity on the heterologous recombinant protein of interest in the host cell without said inactivation, and wherein the spent culture broth has a reduced amount of endogenous proteases compared to a corresponding spent culture broth produced in a host cell with an intact nucleic acid sequence encoding a polypeptide comprising a sequence having at least 90% sequence identity with the amino acids 402-533 of SEQ ID NO: 13;
and wherein the heterologous recombinant protein of interest has an increased stability in the spent culture broth compared to a protein preparation produced in the same host cell without said inactivation.

2. The protein preparation of claim 1, wherein the protein preparation further comprises at least one further component selected from stabilizer, preservative, fragrant, buffer, salt, and colorant.

3. The protein preparation of claim 1, wherein the protein preparation has an improved protein stability compared to a corresponding protein preparation produced in a host cell with an intact nucleic acid sequence encoding a polypeptide comprising a sequence having at least 90% sequence identity with the amino acids 402-533 of SEQ ID NO: 13.

4. The protein preparation of claim 2, wherein the protein preparation has an improved protein stability compared to a corresponding protein preparation produced in a host cell with an intact nucleic acid sequence encoding a polypeptide comprising a sequence having at least 90% sequence identity with the amino acids 402-533 of SEQ ID NO: 13.

5. The protein preparation of claim 1, wherein the protein preparation further comprises at least one recombinant protein produced by the host cell and selected from a pharmacologically active protein, antibody, antibody fragment, therapeutic protein, biosimilar, multi-domain protein, peptide hormone, antimicrobial peptide, peptide, carbohydrate binding module, enzyme, cellulase, protease, protease inhibitor, aminopeptidase, amylase, carbohydrase, carboxypeptidase, catalase, chitinase, cutinase, deoxyribonuclease, esterase, alpha-galactosidase, beta-galactosidase, glucoamylase, alpha-glucosidase, beta-glucosidase, invertase, laccase, lipase, mannanase, mutanase, oxidase, pectinolytic enzyme, peroxidase, phospholipase, phytase, phosphatase, polyphenoloxidase, redox enzyme, proteolytic enzyme, ribonuclease, transglutaminase, and xylanase.

6. The protein preparation of claim 2, wherein the protein preparation further comprises at least one recombinant protein produced by the host cell and selected from a pharmacologically active protein, antibody, antibody fragment, therapeutic protein, biosimilar, multi-domain protein, peptide hormone, antimicrobial peptide, peptide, carbohydrate binding module, enzyme, cellulase, protease, protease inhibitor, aminopeptidase, amylase, carbohydrase, carboxypeptidase, catalase, chitinase, cutinase, deoxyribonuclease, esterase, alpha-galactosidase, beta-galactosidase, glucoamylase, alpha-glucosidase, beta-glucosidase, invertase, laccase, lipase, mannanase, mutanase, oxidase, pectinolytic enzyme, peroxidase, phospholipase, phytase, phosphatase, polyphenoloxidase, redox enzyme, proteolytic enzyme, ribonuclease, transglutaminase, and xylanase.

7. The protein preparation of claim 3, wherein the protein preparation further comprises at least one recombinant protein produced by the host cell and selected from a pharmacologically active protein, antibody, antibody fragment, therapeutic protein, biosimilar, multi-domain protein, peptide hormone, antimicrobial peptide, peptide, carbohydrate binding module, enzyme, cellulase, protease, protease inhibitor, aminopeptidase, amylase, carbohydrase, carboxypeptidase, catalase, chitinase, cutinase, deoxyribonuclease, esterase, alpha-galactosidase, beta-galactosidase, glucoamylase, alpha-glucosidase, beta-glucosidase, invertase, laccase, lipase, mannanase, mutanase, oxidase, pectinolytic enzyme, peroxidase, phospholipase, phytase, phosphatase, polyphenoloxidase, redox enzyme, proteolytic enzyme, ribonuclease, transglutaminase, and xylanase.

8. The protein preparation of claim 4, wherein the protein preparation further comprises at least one recombinant protein produced by the host cell and selected from a pharmacologically active protein, antibody, antibody fragment, therapeutic protein, biosimilar, multi-domain protein, peptide hormone, antimicrobial peptide, peptide, carbohydrate binding module, enzyme, cellulase, protease, protease inhibitor, aminopeptidase, amylase, carbohydrase, carboxypeptidase, catalase, chitinase, cutinase, deoxyribonuclease, esterase, alpha-galactosidase, beta-galactosidase, glucoamylase, alpha-glucosidase, beta-glucosidase, invertase, laccase, lipase, mannanase, mutanase, oxidase, pectinolytic enzyme, peroxidase, phospholipase, phytase, phosphatase, polyphenoloxidase, redox enzyme, proteolytic enzyme, ribonuclease, transglutaminase, and xylanase.

9. The protein preparation of claim 1, wherein the protein preparation further comprises at least one recombinant protein produced by the host cell and selected from a pharmacologically active protein, antibody, antibody fragment, therapeutic protein, biosimilar, multi-domain protein, peptide hormone, antimicrobial peptide, peptide, carbohydrate binding module, enzyme, cellulase, protease, protease inhibitor, aminopeptidase, amylase, carbohydrase, carboxypeptidase, catalase, chitinase, cutinase, deoxyribonuclease, esterase, alpha-galactosidase, beta-galactosidase, glucoamylase, alpha-glucosidase, beta-glucosidase, invertase, laccase, lipase, mannanase, mutanase, oxidase, pectinolytic enzyme, peroxidase, phospholipase, phytase, phosphatase, polyphenoloxidase, redox enzyme, proteolytic enzyme, ribonuclease, transglutaminase, and xylanase.

10. The protein preparation of claim 5, wherein the heterologous recombinant protein has improved protein authenticity compared to a corresponding protein preparation produced in a host cell with an intact nucleic acid sequence encoding a polypeptide comprising a sequence having at least 90% sequence identity with the amino acids 402-533 of SEQ ID NO: 13.

* * * * *

SEQUENCE LISTING

```
<160> NUMBER OF SEQ ID NOS: 30

<210> SEQ ID NO 1
<211> LENGTH: 885
<212> TYPE: DNA
<213> ORGANISM: Trichoderma reesei

<400> SEQUENCE: 1
atggtttggg gtgctggatc gagtgaactc ctggtcgagg ccaacttta cttcgaagct      60 cgcgacgcag atcaaggcgg tgactacctg atgcgagctt tcaagcagct cgagctggac     120
ctcagaaagc tctcgccaca aggcatcatg gaactaatcc tgggtatgat caatcgggat     180
cccggcatga tgacggccct ttgcaagtac cttgcagcat attcgacaac caatctggag     240
cgaacccatc ctctccggca aatcttcact tgtctgtatg aagtgcaaca aaagcatggg     300
gcgcagacgt tgtctgagct cctgtggact agcatctcga caattgcgga ggaactcgag     360
gccatctatg gacgcaagca tccgtatgtg gctcgcacat gggccgatct tgcgctgttt     420
tacagccagg tgaacccgga aaggctggag aagttggttg ttgagcttcg tgtgctccag     480
aggcagctcg agcaacgaca tgggcattcc agtgtcgaag tggtttccat ccgatatgcc     540
attctgctgt tggtctatgc gtcgtctccc cagtcggatg cctcgaagca agccgcaaat     600
gattattgga acctgctgcg gaatatgaac accatgtttc ccatgcgcga ctcccgtccg     660
aatagttact gctatcacag cccgctcaag gtcgatccgt ggacaaagag gtgccgcagg     720
cggtacgaca cactcgtcac catattcgag gagcatgtag gcgttagaat caatccctat     780
```

```
ttcgaagagg acttccacac gaccgagcac gctcaagaaa cgcaggatgc ctgggcggca    840
gctctgcaaa tgggttcgac gaatagatct tggggcttca tctag                   885
```

<210> SEQ ID NO 2
<211> LENGTH: 1344
<212> TYPE: DNA
<213> ORGANISM: Trichoderma reesei

<400> SEQUENCE: 2

```
atggtttggg gtgctggatc gagtgaactc ctggtcgagg ccaactttta cttcgaagct     60
cgcgacgcag atcaaggcgg tgactacctg atgcgagctt tcaagcagct cgagctggac   120
ctcagaaagc tctcgccaca aggcatcatg aactaatcc tgggtatgat caatcgggat    180
cccggcatga tgacggccct ttgcaagtac cttgcagcat attcgacaac caatctggag   240
cgaacccatc ctctccggca atcttcact tgtctgtatg aagtgcaaca aaagcatggg    300
gcgcagacgt tgtctgagct cctgtggact agcatctcga caattgcgga ggaactcgag   360
gccatctatg gacgcaagca tccccaggtg aacccggaaa ggctggagaa gttggttgtt   420
gagcttcgtg tgctccagag gcagctcgag caacgacatg gcattccag tgtcgaagtg     480 gtttccatcc gatatgccat tctgctgttg gtctatgcgt cgtctcccca gtcggatgcc   540
tcgaagcaag ccgcaaatga ttattggaac ctgctgcgga atatgaacac catgtttccc   600
atgcgcgact cccgtccgaa tagttactgc tatcacagcc cgctcaaggt cgatccgtgg   660
acaaagaggt gccgcaggcg gtacgacaca ctcgtcacca tattcgagga gcatgtaggc   720
gttagaatca atccctattt cgaagaggac ttccacacga ccgagcacgc tcaagaaacg   780
caggatgcct gggcggcagc tctgcaaatg ggttcgacga atagatcttg gggcttcatc   840
tagcggtttc gctttcagaa tgttgggtgt gttccacgcc cagctggcgc aaatgtcagg   900
tacccaagat accttgtctc tcgtctccta gcgcgcggtg cagcgagctt ctttttcgag   960 atttctttt ccggaatcta gcgggcggtt aatacccagc atcagaagga ttgcggccga  1020
tctacctagc gacagttttt ttcggttacg tcctgtttgc cacctcacat cgagcctgga  1080
gttttggaca gttgacaatt ctcgccatcg cggaacattt tcctttctca tgtcgccgac  1140
gctgacaagt cgatttcctt ggtctttcca cgcaagttgt tgcacctctc gagccgggcg  1200
ttagggaggg cctttccccc cttggatgcg tcgtcatccg tgtataatag tatccgttgt  1260
tttctgtttt cctttcctgc gtttgatatg cgatgttcag ctttcttgat actgaagacc  1320
acgagggaga ggcgggaaac gagt                                          1344
```

<210> SEQ ID NO 3
<211> LENGTH: 280
<212> TYPE: PRT
<213> ORGANISM: Trichoderma reesei

<400> SEQUENCE: 3

```
Met Val Trp Gly Ala Gly Ser Ser Glu Leu Leu Val Glu Ala Asn Phe
  1               5                  10                  15

Tyr Phe Glu Ala Arg Asp Ala Asp Gln Gly Gly Asp Tyr Leu Met Arg
                 20                  25                  30

Ala Phe Lys Gln Leu Glu Leu Asp Leu Arg Lys Leu Ser Pro Gln Gly
             35                  40                  45

Ile Met Glu Leu Ile Leu Gly Met Ile Asn Arg Asp Pro Gly Met Met
         50                  55                  60

Thr Ala Leu Cys Lys Tyr Leu Ala Ala Tyr Ser Thr Thr Asn Leu Glu
```

```
                65                  70                  75                  80
Arg Thr His Pro Leu Arg Gln Ile Phe Thr Cys Leu Tyr Glu Val Gln
                    85                  90                  95

Gln Lys His Gly Ala Gln Thr Leu Ser Glu Leu Leu Trp Thr Ser Ile
                100                 105                 110

Ser Thr Ile Ala Glu Glu Leu Glu Ala Ile Tyr Gly Arg Lys His Pro
                115                 120                 125

Gln Val Asn Pro Glu Arg Leu Glu Lys Leu Val Val Glu Leu Arg Val
            130                 135                 140

Leu Gln Arg Gln Leu Glu Gln Arg His Gly His Ser Ser Val Glu Val
145                 150                 155                 160

Val Ser Ile Arg Tyr Ala Ile Leu Leu Val Tyr Ala Ser Ser Pro
                165                 170                 175

Gln Ser Asp Ala Ser Lys Gln Ala Ala Asn Asp Tyr Trp Asn Leu Leu
                180                 185                 190

Arg Asn Met Asn Thr Met Phe Pro Met Arg Asp Ser Arg Pro Asn Ser
                195                 200                 205

Tyr Cys Tyr His Ser Pro Leu Lys Val Asp Pro Trp Thr Lys Arg Cys
            210                 215                 220

Arg Arg Arg Tyr Asp Thr Leu Val Thr Ile Phe Glu Glu His Val Gly
225                 230                 235                 240

Val Arg Ile Asn Pro Tyr Phe Glu Glu Asp Phe His Thr Thr Glu His
                245                 250                 255

Ala Gln Glu Thr Gln Asp Ala Trp Ala Ala Ala Leu Gln Met Gly Ser
                260                 265                 270

Thr Asn Arg Ser Trp Gly Phe Ile
                275                 280

<210> SEQ ID NO 4
<211> LENGTH: 2749
<212> TYPE: DNA
<213> ORGANISM: Trichoderma reesei

<400> SEQUENCE: 4
atgttccatc aaccgccgga aaagcctcgc gcgcctggct cgacgatga tccgttcggg      60 tttgtcaccc aggcctggga gagatatggc ctgggcagtg tgtcgtcgcc tccgcctgcg     120
atgcctccgc agcccatcca aggaccggaa cgggcctatt ccaccgcttc ggtaatggac     180
tggacgcccg agatcgatac cacctttcac caccacggcg acggagtggc catgtcgccg     240
gtggaacacg tcgaactgga cagccttggt tcgcctcagg gagggggagg ggttggccgc     300
ttggtcgcgc actttgagaa taaaggctat gtcccgccat gcctccgcg gcccatcaac     360 aatcagccgc atcaaccgca tcacatgggc acagtcctt caatgtcgtc gcagtttggc     420
agtctaaact ctgtagccca tacgcatagg atatcgagtc ccgttgctag cccaggtgaa     480
tcccaatatg gctcgctcgg ggtgcattcg ccccaacac ccacctcaat cgtcaccaac      540
atgaaccgct ccggcagtat aagctatggc agcttccatg acactcagca ggtgcatagt     600
cccggtattg gtacgccttt tgggagcatg gatggcttta tgagttctgc ccgcgtgaac     660
agcccgatgg tggcgacacc aatggcatcg acgcccatga tgcccagtcc catggccgct     720
ccgggagtgc ctggtacccc tggattcgag atttggcgac tcctcccctc gatgactccc     780
aaacctgaac cctctcaaat caccaaccca gccaatttcg gcggctattt cagacctcca     840
gtgccgacga ctcccaagcc ggtagtcaac acaggtaatc agttcatctt ggaattcaac     900
```

```
cccagcgcca aggcagccaa agggaaagct ccggcaaagc ctcccaggcc tcgattgcct    960
cctcggaaac ccaacctttc acaatcacaa ctctcggcac aaacaccagc agcacctgtg   1020
caagcgtcgg tttcaacacc ggcaccggca tcggcaccga caccgacacc agccgttgcc   1080
tcaactccag gtccaatgtc tcctcctcct aaaccgcctc gcccttcaga accgtcttct   1140
tcatccacac ccattgttgt gagcaatgcc gctaaaccaa gagaatcctt gcagctaggt   1200
gtactaacgc gcatgtctag gcacagcggc gggattcgat ggctcttcgt gcccaggcag   1260
gtactaggcc gtcacgggaa caggttcctg cagaggcctg ggagcaatac aaatccacta   1320
tccgtaccct ctatctcgag gagagaaaac ccttgaaaga agtcatgagt gtcatggctg   1380
aacaatatgg gtttcaagca acgtgagtcg aagattgatt cctcttctgc ttcatcgttc   1440
gggttcttgg ttcgttgtaa actaattcga cgcccttct aggccaaaga tgtataaaac   1500
aaggttctct caatggggtt ttgtgaagaa taacacggag gaagaagtga acggctgtt   1560
gtcgatgaag ttccagcgag atgccgaggg caaagtttcc gagtttgttc gaaacggcag   1620
ggtggtgaac ctaggtacct atttgaaacg gaaaggagtg acggagtatg acctcgttga   1680
tttcgaacta ccggccgacc ttccagcaca tatccgatgc agaacaccga caccacctcc   1740
ggctctgcga tcacccgatc tgctccgtgc acaggagta gtcgttggaa atatgcgcaa   1800
ggcattccta cactgtcggc aattcgagat ggagactgag actcagattg gttggccatc   1860
aaccatggtt tggggtgctg gatcgagtga actcctggtc gaggccaact tttacttcga   1920
agctcgcgac gcagatcaag gcggtgacta cctgatgcga gctttcaagc agctcgagct   1980
ggacctcaga aagctctcgc acaaggcat catggaacta atcctgggta tgatcaatcg   2040
ggatcccggc atgatgacgg ccctttgcaa gtaccttgca gcatattcga caaccaatct   2100
ggagcgaacc catcctctcc ggcaaatctt cacttgtctg tatgaagtgc aacaaaagca   2160
tggggcgcag acgttgtctg agctcctgtg gactagcatc tcgacaattg cggaggaact   2220
cgaggccatc tatggacgca agcatccgta tgtggctcgc acatgggccg atcttgcgct   2280
gttttacagc caggtgaacc cggaaaggct ggagaagttg gttgttgagc ttcgtgtgct   2340
ccagaggcag ctcgagcaac gacatgggca ttcagtgtc gaagtggttt ccatccgata   2400
tgccattctg ctgttggtct atgcgtcgtc tccccagtcg gatgcctcga agcaagccgc   2460
aaatgattat tggaacctgc tgcggaatat gaacaccatg tttcccatgc gcgactcccg   2520
tccgaatagt tactgctatc acagcccgct caaggtcgat ccgtggacaa agaggtgccg   2580
caggcggtac gacacactcg tcaccatatt cgaggagcat gtaggcgtta gaatcaatcc   2640
ctatttcgaa gaggacttcc acacgaccga gcacgctcaa gaaacgcagg atgcctgggc   2700
ggcagctctg caaatggggtt cgacgaatag atcttggggc ttcatctag             2749
```

<210> SEQ ID NO 5
<211> LENGTH: 2478
<212> TYPE: DNA
<213> ORGANISM: Trichoderma reesei

<400> SEQUENCE: 5

```
atgttccatc aaccgccgga aaagcctcgc gcgcctggct cgacgatga tccgttcggg     60
tttgtcaccc aggcctggga gagatatggc ctgggcagtg tgtcgtcgcc tccgcctgcg    120
atgcctccgc agcccatcca gaggaccgga cgggcctatt ccaccgcttc ggtaatggac    180
tggacgcccg agatcgatac cacctttcac caccacggcg acgagtggc catgtcgccg    240
gtggaacacg tcgaactgga cagccttggt tcgcctcagg gaggggagg ggttggccgc    300
```

```
ttggtcgcgc actttgagaa taaaggctat gtcccgccat tgcctccgcg gccatcaac    360 aatcagccgc atcaaccgca tcacatgggc cacagtcctt caatgtcgtc gcagtttggc    420
agtctaaact ctgtagccca tacgcatagg atatcgagtc ccgttgctag cccaggtgaa    480
tcccaatatg gctcgctcgg ggtgcattcg cccccaacac ccacctcaat cgtcaccaac    540
atgaaccgct ccggcagtat aagctatggc agcttccatg cactcagca ggtgcatagt    600 cccggtattg gtacgccttt tgggagcatg gatggcttta tgagttctgc ccgcgtgaac    660
agcccgatgg tggcgacacc aatggcatcg acgcccatga tgcccagtcc catggccgct    720
ccgggagtgc ctggtacccc tggattcgag atttggcgac ctcctccctc gatgactccc    780
aaacctgaac cctctcaaat caccaaccca gccaatttcg gcggctattt cagacctcca    840
gtgccgacga ctcccaagcc ggtagtcaac acaggtaatc agttcatctt ggaattcaac    900
cccagcgcca aggcagccaa agggaaagct ccggcaaagc ctcccaggcc tcgattgcct    960
cctcggaaac ccaacctttc acaatcacaa ctctcggcac aaacaccagc agcacctgtg   1020
caagcgtcgg cacagcggcg ggattcgatg gctcttcgtg cccaggcagg tactaggccg   1080
tcacgggaac aggttcctgc agaggcctgg gagcaataca aatccactat ccgtaccctc   1140
tatctcgagg agagaaaacc cttgaaagaa gtcatgagtg tcatggctga acaatatggg   1200
tttcaagcaa cgccaaagat gtataaaaca aggttctctc aatggggttt tgtgaagaat   1260
aacacggagg aagaagtgaa acggctgttg tcgatgaagt tccagcgaga tgccgagggc   1320
aaagtttccg agtttgttcg aaacggcagg gtggtgaacc taggtaccta tttgaaacgg   1380
aaaggagtga cggagtatga cctcgttgat ttcgaactac cggccgacct tccagcacat   1440
atccgatgca gaacaccgac accacctccg gctctgcgat cacccgatct gctccgtgca   1500
caggaggtag tcgttggaaa tatgcgcaag gcattcctac actgtcggca attcgagatg   1560
gagactgaga ctcagattgg ttggccatca accatggttt ggggtgctgg atcgagtgaa   1620
ctcctggtcg aggccaactt ttacttcgaa gctcgcgacg cagatcaagg cggtgactac   1680
ctgatgcgag cttttcaagca gctcgagctg acctcagaa agctctcgcc acaaggcatc   1740
atggaactaa tcctgggtat gatcaatcgg gatcccggca tgatgacggc ctttgcaag   1800 taccttgcag catattcgac aaccaatctg gagcgaaccc atcctctccg gcaaatcttc   1860
acttgtctgt atgaagtgca acaaaagcat ggggcgcaga cgttgtctga gctcctgtgg   1920
actagcatct cgacaattgc ggaggaactc gaggccatct atggacgcaa gcatccgtat   1980
gtggctcgca catgggccga tcttgcgctg ttttacagcc aggtgaaccc ggaaaggctg   2040
gagaagttgg ttgttgagct tcgtgtgctc cagaggcagc tcgagcaacg acatgggcat   2100
tccagtgtcg aagtggttc catccgatat gccattctgc tgttggtcta tgcgtcgtct   2160 cccccagtcgg atgcctcgaa gcaagccgca atgattatt ggaacctgct gcggaatatg   2220
aacaccatgt ttcccatgcg cgactcccgt ccgaatagtt actgctatca cagcccgctc   2280
aaggtcgatc cgtggacaaa gaggtgccgc aggcggtacg acacactcgt caccatattc   2340
gaggagcatg taggcgttag aatcaatccc tatttcgaag aggacttcca cacgaccgag   2400
cacgctcaag aaacgcagga tgcctgggcg gcagctctgc aaatgggttc gacgaataga   2460
tcttggggct tcatctag                                                 2478
```

<210> SEQ ID NO 6
<211> LENGTH: 825
<212> TYPE: PRT

<213> ORGANISM: Trichoderma reesei

<400> SEQUENCE: 6

```
Met Phe His Gln Pro Pro Glu Lys Pro Arg Ala Pro Gly Phe Asp Asp
1               5                   10                  15

Asp Pro Phe Gly Phe Val Thr Gln Ala Trp Glu Arg Tyr Gly Leu Gly
            20                  25                  30

Ser Val Ser Ser Pro Pro Ala Met Pro Pro Gln Pro Ile Gln Arg
        35                  40                  45

Thr Gly Arg Ala Tyr Ser Thr Ala Ser Val Met Asp Trp Thr Pro Glu
    50                  55                  60

Ile Asp Thr Thr Phe His His His Gly Asp Gly Val Ala Met Ser Pro
65                  70                  75                  80

Val Glu His Val Glu Leu Asp Ser Leu Gly Ser Pro Gln Gly Gly Gly
                85                  90                  95

Gly Val Gly Arg Leu Val Ala His Phe Glu Asn Lys Gly Tyr Val Pro
            100                 105                 110

Pro Leu Pro Pro Arg Pro Ile Asn Asn Gln Pro His Gln Pro His His
        115                 120                 125

Met Gly His Ser Pro Ser Met Ser Ser Gln Phe Gly Ser Leu Asn Ser
130                 135                 140

Val Ala His Thr His Arg Ile Ser Ser Pro Val Ala Ser Pro Gly Glu
145                 150                 155                 160

Ser Gln Tyr Gly Ser Leu Gly Val His Ser Pro Pro Thr Pro Thr Ser
                165                 170                 175

Ile Val Thr Asn Met Asn Arg Ser Gly Ser Ile Ser Tyr Gly Ser Phe
            180                 185                 190

His Asp Thr Gln Gln Val His Ser Pro Gly Ile Gly Thr Pro Phe Gly
        195                 200                 205

Ser Met Asp Gly Phe Met Ser Ser Ala Arg Val Asn Ser Pro Met Val
210                 215                 220

Ala Thr Pro Met Ala Ser Thr Pro Met Met Pro Ser Pro Met Ala Ala
225                 230                 235                 240

Pro Gly Val Pro Gly Thr Pro Gly Phe Glu Ile Trp Arg Pro Pro
                245                 250                 255

Ser Met Thr Pro Lys Pro Glu Pro Ser Gln Ile Thr Asn Pro Ala Asn
            260                 265                 270

Phe Gly Gly Tyr Phe Arg Pro Val Pro Thr Thr Pro Lys Pro Val
        275                 280                 285

Val Asn Thr Gly Asn Gln Phe Ile Leu Glu Phe Asn Pro Ser Ala Lys
290                 295                 300

Ala Ala Lys Gly Lys Ala Pro Ala Lys Pro Pro Arg Pro Arg Leu Pro
305                 310                 315                 320

Pro Arg Lys Pro Asn Leu Ser Gln Ser Gln Leu Ser Ala Gln Thr Pro
                325                 330                 335

Ala Ala Pro Val Gln Ala Ser Ala Gln Arg Arg Asp Ser Met Ala Leu
            340                 345                 350

Arg Ala Gln Ala Gly Thr Arg Pro Ser Arg Glu Gln Val Pro Ala Glu
        355                 360                 365

Ala Trp Glu Gln Tyr Lys Ser Thr Ile Arg Thr Leu Tyr Leu Glu Glu
370                 375                 380

Arg Lys Pro Leu Lys Glu Val Met Ser Val Met Ala Glu Gln Tyr Gly
385                 390                 395                 400
```

```
Phe Gln Ala Thr Pro Lys Met Tyr Lys Thr Arg Phe Ser Gln Trp Gly
                405                 410                 415

Phe Val Lys Asn Asn Thr Glu Glu Val Lys Arg Leu Leu Ser Met
                420                 425                 430

Lys Phe Gln Arg Asp Ala Glu Gly Lys Val Ser Glu Phe Val Arg Asn
                435                 440                 445

Gly Arg Val Val Asn Leu Gly Thr Tyr Leu Lys Arg Lys Gly Val Thr
450                 455                 460

Glu Tyr Asp Leu Val Asp Phe Glu Leu Pro Ala Asp Leu Pro Ala His
465                 470                 475                 480

Ile Arg Cys Arg Thr Pro Thr Pro Pro Ala Leu Arg Ser Pro Asp
                485                 490                 495

Leu Leu Arg Ala Gln Glu Val Val Gly Asn Met Arg Lys Ala Phe
                500                 505                 510

Leu His Cys Arg Gln Phe Glu Met Glu Thr Glu Thr Gln Ile Gly Trp
                515                 520                 525

Pro Ser Thr Met Val Trp Gly Ala Gly Ser Glu Leu Leu Val Glu
                530                 535                 540

Ala Asn Phe Tyr Phe Glu Ala Arg Asp Ala Asp Gln Gly Gly Asp Tyr
545                 550                 555                 560

Leu Met Arg Ala Phe Lys Gln Leu Glu Leu Asp Leu Arg Lys Leu Ser
                565                 570                 575

Pro Gln Gly Ile Met Glu Leu Ile Leu Gly Met Ile Asn Arg Asp Pro
                580                 585                 590

Gly Met Met Thr Ala Leu Cys Lys Tyr Leu Ala Ala Tyr Ser Thr Thr
                595                 600                 605

Asn Leu Glu Arg Thr His Pro Leu Arg Gln Ile Phe Thr Cys Leu Tyr
                610                 615                 620

Glu Val Gln Gln Lys His Gly Ala Gln Thr Leu Ser Glu Leu Leu Trp
625                 630                 635                 640

Thr Ser Ile Ser Thr Ile Ala Glu Glu Leu Glu Ala Ile Tyr Gly Arg
                645                 650                 655

Lys His Pro Tyr Val Ala Arg Thr Trp Ala Asp Leu Ala Leu Phe Tyr
                660                 665                 670

Ser Gln Val Asn Pro Glu Arg Leu Glu Lys Leu Val Val Glu Leu Arg
                675                 680                 685

Val Leu Gln Arg Gln Leu Glu Gln Arg His Gly His Ser Ser Val Glu
                690                 695                 700

Val Val Ser Ile Arg Tyr Ala Ile Leu Leu Val Tyr Ala Ser Ser
705                 710                 715                 720

Pro Gln Ser Asp Ala Ser Lys Gln Ala Ala Asn Asp Tyr Trp Asn Leu
                725                 730                 735

Leu Arg Asn Met Asn Thr Met Phe Pro Met Arg Asp Ser Arg Pro Asn
                740                 745                 750

Ser Tyr Cys Tyr His Ser Pro Leu Lys Val Asp Pro Trp Thr Lys Arg
                755                 760                 765

Cys Arg Arg Arg Tyr Asp Thr Leu Val Thr Ile Phe Glu Glu His Val
                770                 775                 780

Gly Val Arg Ile Asn Pro Tyr Phe Glu Glu Asp Phe His Thr Thr Glu
785                 790                 795                 800

His Ala Gln Glu Thr Gln Asp Ala Trp Ala Ala Ala Leu Gln Met Gly
                805                 810                 815

Ser Thr Asn Arg Ser Trp Gly Phe Ile
```

<210> SEQ ID NO 7
<211> LENGTH: 2751
<212> TYPE: DNA
<213> ORGANISM: Trichoderma reesei

<400> SEQUENCE: 7

```
atgttccatc aaccgccgga aaagcctcgc gcgcctggct tcgacgatga tccgttcggg      60
tttgtcaccc aggcctggga gagatatggc ctgggcagtg tgtcgtcgcc tccgcctgcg     120
atgcctccgc agcccatcca gaggaccgga cgggcctatt ccaccgcttc ggtaatggac     180
tggacgcccg agatcgatac cacctttcac caccacggcg acggagtggc catgtcgccg     240
gtggaacacg tcgaactgga cagccttggt tcgcctcagg gagggggagg ggttggccgc     300
ttggtcgcgc actttgagaa taaaggctat gtcccgccat gcctccgcg gcccatcaac      360
aatcagccgc atcaaccgca tcacatgggc cacagtcctt caatgtcgtc gcagtttggc     420
agtctaaact ctgtagccca tacgcatagg atatcgagtc ccgttgctag cccaggtgaa     480
tcccaatatg gctcgctcgg ggtgcattcg cccccaacac ccacctcaat cgtcaccaac     540
atgaaccgct ccggcagtat aagctatggc agcttccatg acactcagca ggtgcatagt     600
cccggtattg gtacgccttt tgggagcatg gatggcttta tgagttctgc ccgcgtgaac     660
agcccgatgg tggcgacacc aatggcatcg acgcccatga tgcccagtcc catggccgct     720
ccgggagtgc ctggtacccc tggattcgag atttggcgac ctcctccctc gatgactccc     780
aaacctgaac cctctcaaat caccaaccca gccaatttcg gcggctattt cagacctcca     840
cagtgccgac gactcccaag ccggtagtca acacaggtaa tcagttcatc ttggaattca     900
accccagcgc caaggcagcc aaagggaaag ctccggcaaa gcctcccagg cctcgattgc     960
ctcctcggaa acccaacctt tcacaatcac aactctcggc acaaacacca gcagcacctg    1020
tgcaagcgtc ggtttcaaca ccggcaccgg catcggcacc gacaccgaca ccagccgttg    1080
cctcaactcc aggtccaatg tctcctcctc ctaaaccgcc tcgcccttca gaaccgtctt    1140
cttcatccac acccattgtt gtgagcaatg ccgctaaacc aagagaatcc ttgcagctag    1200
gtgtactaac gcgcatgtct aggcacagcg gcgggattcg atggctcttc gtgcccaggc    1260
aggtactagg ccgtcacggg aacaggttcc tgcagaggcc tgggagcaat acaaatccac    1320
tatccgtacc ctctatctcg aggagagaaa acccttgaaa gaagtcatga gtgtcatggc    1380
tgaacaatat gggtttcaag caacgtgagt cgaagattga ttcctcttct gcttcatcgt    1440
tcgggttctt ggttcgttgt aaactaattc gacgcccttt ctaggccaaa gatgtataaa    1500
acaaggttct ctcaatgggg ttttgtgaag aataacacgg aggaagaagt gaaacggctg    1560
ttgtcgatga agttccagcg agatgccgag ggcaaagttt ccgagtttgt tcgaaacggc    1620
agggtggtga acctaggtac ctatttgaaa cggaaaggag tgacggagta tgacctcgtt    1680
gatttcgaac taccggccga ccttccagca catatccgat gcagaacacc gacaccacct    1740
ccggctctgc gatcacccga tctgctccgt gcacaggagg tagtcgttgg aaatatgcgc    1800
aaggcattcc tacactgtcg gcaattcgag atggagactg agactcagat tggttggcca    1860
tcaaccatgg tttggggtgc tggatcgagt gaactcctgg tcgaggccaa cttttacttc    1920
gaagctcgcg acgcagatca aggcggtgac tacctgatgc gagctttcaa gcagctcgag    1980
ctggacctca gaaagctctc gccacaaggc atcatggaac taatcctggg tatgatcaat    2040
cgggatcccg gcatgatgac ggccctttgc aagtaccttg cagcatattc gacaaccaat    2100
```

```
ctggagcgaa cccatcctct ccggcaaatc ttcacttgtc tgtatgaagt gcaacaaaag    2160 catgggcgc agacgttgtc tgagctcctg tggactagca tctcgacaat tgcggaggaa    2220
ctcgaggcca tctatggacg caagcatccg tatgtggctc gcacatgggc cgatcttgcg    2280
ctgttttaca gccaggtgaa cccggaaagg ctggagaagt tggttgttga gcttcgtgtg    2340
ctccagaggc agctcgagca acgacatggg cattccagtg tcgaagtggt ttccatccga    2400
tatgccattc tgctgttggt ctatgcgtcg tctccccagt cggatgcctc gaagcaagcc    2460
gcaaatgatt attggaacct gctgcggaat atgaacacca tgtttcccat gcgcgactcc    2520
cgtccgaata gttactgcta tcacagcccg ctcaaggtcg atccgtggac aaagaggtgc    2580
cgcaggcggt acgacacact cgtcaccata ttcgaggagc atgtaggcgt tagaatcaat    2640
ccctatttcg aagaggactt ccacacgacc gagcacgctc aagaaacgca ggatgcctgg    2700
gcggcagctc tgcaaatggg ttcgacgaat agatcttggg gcttcatcta g            2751

<210> SEQ ID NO 8
<211> LENGTH: 2749
<212> TYPE: DNA
<213> ORGANISM: Trichoderma reesei

<400> SEQUENCE: 8
atgttccatc aaccgccgga aaagcctcgc gcgcctggct tcgacgatga tccgttcggg      60
tttgtcaccc aggcctggga gagatatggc ctgggcagtg tgtcgtcgcc tccgcctgcg     120
atgcctccgc agcccatcca gaggaccgga cgggcctatt ccaccgcttc ggtaatggac     180
tggacgcccg agatcgatac cacctttcac caccacggcg acggagtggc catgtcgccg     240
gtggaacacg tcgaactgga cagccttggt tcgcctcagg gagggggagg ggttggccgc     300
ttggtcgcgc actttgagaa taaaggctat gtcccgccat gcctccgcg gcccatcaac     360 aatcagccgc atcaaccgca tcacatgggc cacagtcctt caatgtcgtc gcagtttggc     420 agtctaaaact ctgtagccca tacgcatagg atatcgagtc ccgttgctag cccaggtgaa     480
tcccaatatg gctcgctcgg ggtgcattgc cccccaacac ccacctcaat cgtcaccaac     540
atgaaccgct ccggcagtat aagctatggc agcttccatg acactcagca ggtgcatagt     600
cccggtattg gtacgccttt tgggagcatg gatggcttta tgagttctgc ccgcgtgaac     660
agcccgatgg tggcgacacc aatggcatcg acgcccatga tgcccagtcc catggccgct     720
ccgggagtgc ctggtacccc tggattcgag atttggcgac ctcctccctc gatgactccc     780
aaacctgaac cctctcaaat caccaaccca gccaatttcg gcggctattt cagacctcca     840
gtgccgacga ctcccaagcc ggtagtcaac acaggtaatc agttcatctt ggaattcaac     900
cccagcgcca aggcagccaa agggaaagct ccggcaaagc ctcccaggcc tgattgcct     960 cctcggaaac ccaaccttt acaatcacaa ctctcggcac aaacaccagc agcacctgtg    1020
caagcgtcgg tttcaacacc ggcaccggca tcggcaccga caccgacacc agccgttgcc    1080
tcaactccag gtccaatgtc tcctcctcct aaaccgcctc gcccttcaga accgtcttct    1140
tcatccacac ccattgttgt gagcaatgcc gctaaaccaa gagaatcctt gcagctaggt    1200
gtactaacgc gcatgtctag gcatagcggc gggattcgat ggctcttcgt gcccaggcag    1260
gtactaggcc gtcacgggaa caggttcctg cagaggcctg ggagcaatac aaatccacta    1320
tccgtaccct ctatctcgag gagagaaaac ccttgaaaga agtcatgagt gtcatggctg    1380
aacaatatgg gtttcaagca acgtgagtcg aagattgatt cctcttctgc ttcatcgttc    1440
```

```
gggttcttgg ttcgttgtaa actaattcga cgcccttcct aggccaaaga tgtataaaac    1500
aaggttctct caatgggggtt ttgtgaagaa taacacggag gaagaagtga aacggctgtt    1560
gtcgatgaag ttccagcgag atgccgaggg caaagtttcc gagtttgttc gaaacggcag    1620
ggtggtgaac ctaggtacct atttgaaacg gaaaggagtg acggagtatg acctcgttga    1680
tttcgaacta ccggccgacc ttccagcaca tatccgatgc agaacaccga caccacctcc    1740
ggctctgcga tcacccgatc tgctccgtgc acaggaggta gtcgttggaa atatgcgcaa    1800
ggcattccta cactgtcggc aattcgagat ggagactgag actcagattg gttggccatc    1860
aaccatggtt tggggtgctg gatcgagtga actcctggtc gaggccaact tttacttcga    1920
agctcgcgac gcagatcaag gcggtgacta cctgatgcga gctttcaagc agctcgagct    1980
ggacctcaga aagctctcgc cacaaggcat catggaacta tcctgggta tgatcaatcg    2040 ggatcccggc atgatgacgg ccctttgcaa gtaccttgca gcatattcga caaccaatct    2100
ggagcgaacc catcctctcc ggcaaatctt cacttgtctg tatgaagtgc aacaaaagca    2160
tggggcgcag acgttgtctg agctcctgtg gactagcatc tcgacaattg cggaggaact    2220
cgaggccatc tatggacgca agcatccgta tgtggctcgc acatgggccg atcttgcgct    2280
gttttacagc caggtgaacc cggaaaggct ggagaagttg gttgttgagc ttcgtgtgct    2340
ccagaggcag ctcgagcaac gacatgggca ttccagtgtc gaagtggttt ccatccgata    2400
tgccattctg ctgttggtct atgcgtcgtc tccccagtcg gatgcctcga agcaagccgc    2460
aaatgattat tggaacctgc tgcggaatat gaacaccatg tttcccatgc gcgactcccg    2520
tccgaatagt tactgctatc acagcccgct caaggtcgat ccgtggacaa agaggtgccg    2580
caggcggtac gacacactcg tcaccatatt cgaggagcat gtaggcgtta gatcaatcc    2640 ctatttcgaa gaggacttcc acacgaccga gcacgctcaa gaaacgcagg atgcctgggc    2700
ggcagctctg caaatgggtt cgacgaatag atcttggggc ttcatctag                2749

<210> SEQ ID NO 9
<211> LENGTH: 2748
<212> TYPE: DNA
<213> ORGANISM: Trchoderma reesei

<400> SEQUENCE: 9
atgttccatc aaccgccgga aaagcctcgc gcgcctggct tcgacgatga tccgttcggg      60
tttgtcaccc aggcctggga gagatatggc ctgggcagtg tgtcgtcgcc tccgcctgcg     120
atgcctccgc agcccatcca gaggaccgga cgggcctatt ccaccgcttc ggtaatggac     180
tggacgcccg agatcgatac cacctttcac caccacggcg acggagtggc catgtcgccg     240
gtggaacacg tcgaactgga cagccttggt tcgcctcagg gagggggagg ggttggccgc     300
ttggtcgcgc actttgagaa taaaggctat gtcccgccat tgcctccgcg gcccatcaac     360
aatcagccgc atcaaccgca tcacatgggc acagtccctt caatgtcgtc gcagtttggc     420 agtctaaaact ctgtagccca tacgcatagg atatcgagtc ccgttgctag cccaggtgaa     480
tcccaatatg gctcgctcgg ggtgcattcg cccccaacac ccacctcaat cgtcaccaac     540
atgaaccgct ccggcagtat aagctatggc agcttccatg acactcagca ggtgcatagt     600
cccggtattg gtacgccttt tgggagcatg gatggcttta tgagttctgc ccgcgtgaac     660
agcccgatgg tggcgacacc aatggcatcg acgcccatga tgcccagtcc catggccgct     720
ccgggagtgc ctggtacccc tggattcgag atttggcgac ctcctccctc gatgactccc     780
aaacctgaac cctctcaaat caccaaccca gccaatttcg gcggctattt cagacctcca     840
```

```
gtgccgacga ctcccaagcc ggtagtcaac acaggtaatc agttcatctt ggaattcaac    900
cccagcgcca aggcagccaa agggaaagct ccggcaaagc ctcccaggcc tcgattgcct    960
cctcggaacc caacctttca caatcacaac tctcggcaca aacaccagca gcacctgtgc   1020
aagcgtcggt ttcaacaccg gcaccggcat cggcaccgac accgacacca gccgttgcct   1080
caactccagg tccaatgtct cctcctccta aaccgcctcg cccttcagaa ccgtcttctt   1140
catccacacc cattgttgtg agcaatgccg ctaaaccaag agaatccttg cagctaggtg   1200
tactaacgcg catgtctagg cacagcggcg ggattcgatg gctcttcgtg cccaggcagg   1260
tactaggccg tcacgggaac aggttcctgc agaggcctgg gagcaataca aatccactat   1320
ccgtaccctc tatctcgagg agagaaaacc cttgaaagaa gtcatgagtg tcatggctga   1380
acaatatggg tttcaagcaa cgtgagtcga agattgattc ctcttctgct tcatcgttcg   1440
ggttcttggt tcgttgtaaa ctaattcgac gcccttccta ggccaaagat gtataaaaca   1500
aggttctctc aatggggttt tgtgaagaat aacacggagg aagaagtgaa acggctgttg   1560
tcgatgaagt tccagcgaga tgccgagggc aaagtttccg agtttgttcg aaacggcagg   1620
gtggtgaacc taggtaccta tttgaaacgg aaaggagtga cggagtatga cctcgttgat   1680
ttcgaactac cggccgacct tccagcacat atccgatgca gaacaccgac accacctccg   1740
gctctgcgat caccccgatct gctccgtgca caggaggtag tcgttggaaa tatgcgcaag   1800
gcattcctac actgtcggca attcgagatg gagactgaga ctcagattgg ttggccatca   1860
accatggttt ggggtgctgg atcgagtgaa ctcctggtcg aggccaactt ttacttcgaa   1920
gctcgcgacg cagatcaagg cggtgactac ctgatgcgag cttcaagca gctcgagctg   1980
gacctcagaa agctctcgcc acaaggcatc atggaactaa tcctgggtat gatcaatcgg   2040
gatcccggca tgatgacggc cctttgcaag taccttgcag catattcgac aaccaatctg   2100
gagcgaaccc atcctctccg gcaaatcttc acttgtctgt atgaagtgca acaaaagcat   2160
ggggcgcaga cgttgtctga gctcctgtgg actagcatct cgacaattgc ggaggaactc   2220
gaggccatct atggacgcaa gcatccgtat gtggctcgca catgggccga tcttgcgctg   2280
ttttacagcc aggtgaaccc ggaaaggctg agaagttgg ttgttgagct tcgtgtgctc   2340
cagaggcagc tcgagcaacg acatgggcat ccagtgtcg aagtggtttc catccgatat   2400
gccattctgc tgttggtcta tgcgtcgtct ccccagtcgg atgcctcgaa gcaagccgca   2460
aatgattatt ggaacctgct gcggaatatg aacaccatgt ttcccatgcg cgactcccgt   2520
ccgaatagtt actgctatca cagcccgctc aaggtcgatc cgtggacaaa gaggtgccgc   2580
aggcggtacg acacactcgt caccatattc gaggagcatg taggcgttag aatcaatccc   2640
tatttcgaag aggacttcca cacgaccgag cacgctcaag aaacgcagga tgcctgggcg   2700
gcagctctgc aaatgggttc gacgaataga tcttggggct tcatctag           2748
```

<210> SEQ ID NO 10
<211> LENGTH: 2749
<212> TYPE: DNA
<213> ORGANISM: Trchoderma reesei

<400> SEQUENCE: 10

```
atgttccatc aaccgccgga aaagcctcgc gcgcctggct tcgacgatga tccgttcggg     60
tttgtcaccc aggcctggga gagatatggc ctgggcagtg tgtcgtcgcc tccgcctgcg    120
atgcctccgc agcccatcca gaggaccgga cgggcctatt ccaccgcttc ggtaatggac    180
```

```
tggacgcccg agatcgatac caccttcac caccacggcg acggagtggc catgtcgccg    240
gtggaacacg tcgaactgga cagccttggt tcgcctcagg gagggggagg ggttggccgc    300
ttggtcgcgc actttgagaa taaaggctat gtcccgccat gcctccgcg gcccatcaac     360 aatcagccgc atcaaccgca tcacatgggc cacagtcctt caatgtcgtc gcagtttggc    420
agtctaaact ctgtagccca tacgcatagg atatcgagtc ccgttgctag cccaggtgaa    480
tcccaatatg gctcgctcgg ggtgcattcg cccccaacac ccacctcaat cgtcaccaac    540
atgaaccgct ccggcagtat aagctatggc agcttccatg acactcagca ggtgcatagt    600
cccggtattg gtacgccttt tgggagcatg atggcttta tgagttctgc ccgcgtgaac     660
agcccgatgg tggcgacacc aatggcatcg acgcccatga tgcccagtcc catggccgct    720
ccgggagtgc ctggtacccc tggattcgag atttggcgac ctcctccctc gatgactccc    780
aaacctgaac cctctcaaat caccaaccca gccaatttcg gcggctattt cagacctcca    840
gtgccgacga ctcccaagcc ggtagtcaac acaggtaatc agttcatctt ggaattcaac    900
cccagcgcca aggcagccaa agggaaagct ccggcaaagc ctcccaggcc ttgattgcct    960
cctcggaaac ccaacctttc acaatcacaa ctctcggcac aaacaccagc agcacctgtg   1020
caagcgtcgg tttcaacacc ggcaccggca tcggcaccga caccgacacc agccgttgcc   1080
tcaactccag gtccaatgtc tcctcctcct aaaccgcctc gcccttcaga accgtcttct   1140
tcatccacac ccattgttgt gagcaatgcc gctaaaccaa gagaatcctt gcagctaggt   1200
gtactaacgc gcatgtctag gcacagcggc gggattcgat ggctcttcgt gcccaggcag   1260
gtactaggcc gtcacgggaa caggttcctg cagaggcctg ggagcaatac aaatccacta   1320 tccgtacccct ctatctcgag gagagaaaac ccttgaaaga agtcatgagt gtcatggctg   1380
aacaatatgg gtttcaagca acgtgagtcg aagattgatt cctcttctgc ttcatcgttc   1440
gggttcttgg ttcgttgtaa actaattcga cgcccttct aggccaaaga tgtataaaac   1500
aaggttctct caatggggtt ttgtgaagaa taacacggag gaagaagtga acgggctgtt   1560
gtcgatgaag ttccagcgag atgccgaggg caaagtttcc gagtttgttc gaaacggcag   1620
ggtggtgaac ctaggtacct atttgaaacg gaaaggagtg acggagtatg acctcgttga   1680
tttcgaacta ccggccgacc ttccagcaca tatccgatgc agaacaccga caccacctcc   1740
ggctctgcga tcacccgatc tgctccgtgc acaggaggta gtcgttggaa atatgcgcaa   1800
ggcattccta cactgtcggc aattcgagat ggagactgag actcagattg gttggccatc   1860
aaccatggtt tggggtgctg gatcgagtga actcctggtc gaggccaact tttacttcga   1920
agctcgcgac gcagatcaag gcggtgacta cctgatgcga gctttcaagc agctcgagct   1980 ggaccctcaga aagctctcgc cacaaggcat catggaacta atcctgggta tgatcaatcg   2040
ggatcccggc atgatgacgg cccttttgcaa gtaccttgca gcatattcga caaccaatct   2100
ggagcgaacc catcctctcc ggcaaatctt cacttgtctg tatgaagtgc aacaaaagca   2160
tggggcgcag acgttgtctg agctcctgtg gactagcatc tcgacaattg cggaggaact   2220
cgaggccatc tatggacgca agcatccgta tgtggctcgc acatgggccg atcttgcgct   2280
gttttacagc caggtgaacc cggaaaggct ggagaagttg gttgttgagc ttcgtgtgct   2340
ccagaggcag ctcgagcaac gacatgggca ttccagtgtc gaagtggttt ccatccgata   2400
tgccattctg ctgttggtct atgcgtcgtc tccccagtcg gatgcctcga agcaagccgc   2460
aaatgattat tggaacctgc tgcggaatat gaacaccatg tttcccatgc gcgactcccg   2520
tccgaatagt tactgctatc acagcccgct caaggtcgat ccgtggacaa agaggtgccg   2580
```

```
caggcggtac gacacactcg tcaccatatt cgaggagcat gtaggcgtta gaatcaatcc    2640
ctatttcgaa gaggacttcc acacgaccga gcacgctcaa gaaacgcagg atgcctgggc    2700
ggcagctctg caaatgggtt cgacgaatag atcttggggc ttcatctag                2749
```

<210> SEQ ID NO 11
<211> LENGTH: 4710
<212> TYPE: DNA
<213> ORGANISM: Trichoderma reesei

<400> SEQUENCE: 11

```
cgttggctcg aggcaactgc gtccgtggag gcagaatgcc atcatcgatc ggtcccagca      60
cagtgtcctt gagcgtacgg gcaccagggg gttggtatca gagcgctgcc attgggcgat     120
gtgtcctggc gagtggtggc ttgcgttcat atcaccttct ttttctggcc gatggtggca     180
ttcacacgcc gacccccctg gctactccag ctcaatggcc ggcagcccta cttggtttcc     240
ccggcctgat tatttgcttc gccatcgctg ttgcaatgtt cgttagccac cagcctgcat     300
taggttacat cccctccaat ccaacctctg gctcaccatg ctgctgtctc ttgtctgcta     360
gaggcccctc tctccacctg ctctcgtgcc taggctgtcc ccgtcgtttt gatcccatcg     420
tactagcagc ggcatcagga ctcctagagg caccactcgt actagcccgt agcacaccag     480
ggccagccag aacagctccg tcctggccca gcctgtattt tgagcatctc tggctctctt     540
atctcagcgg gggccttcta aattgaccct ctcgaaaga cggcacatgg gatttccctt      600
cttggcactc tagacgaggg aacttttgct cgctctcttc gctgcgtggc ttggcttggt     660
ttcctcccac gccgctgctg atgcttttgg agctggctgc tcttgttgtt tgtttgtcca     720
aaccacacag cggctgttgc cctatcaagg cgttttccca tcggccga tatctggggg       780 aacgatacgg atatctgccc ctagccagcc agccagccag ccagccagcc agccagccct     840
tgcctgtact ttcgtgctgc gcccgtccca gtaggcctct ccgccgccgt gattccctct     900
ctctttacta tccctctaca ccaggcgatt atgggcacct ttgcccgcct cccatacacg     960
accttcgttt gactgagcaa gcacgctcgc cactctcaga gagtgatgaa tcaccgcgct    1020
ggagactgat tattccagcc gagtcctacg acttgcccag gtccgtcagt tcctgacaga    1080
caagacagcc ggcggactga gcaccactgc tctgtctgct cggtgtgtgg gcacgttgac    1140
atgttccatc aaccgccgga aaagcctcgc gcgcctggct tcgacgatga tccgttcggg    1200
tttgtcaccc aggcctggga gagatatggc ctgggcagtg tgtcgtcgcc tccgcctgcg    1260
atgcctccgc agcccatcca gaggaccgga cgggcctatt ccaccgcttc ggtaatggac    1320
tggacgcccg agatcgatac caccttcac caccacggcg acggagtggc catgtcgccg     1380
gtggaacacg tcgaactgga cagccttggt tcgcctcagg gagggggagg ggttggccgc    1440
ttggtcgcgc actttgagaa taaaggctat gtcccgccat gcctccgcg gcccatcaac     1500 aatcagccgc atcaaccgca tcacatgggc acagtccttc aatgtcgtc gcagtttggc     1560 agtctaaact ctgtagccca tacgcatagg atatcgagtc ccgttgctag cccaggtgaa    1620
tcccaatatg gctcgctcgg ggtgcattcg cccccaacac ccacctcaat cgtcaccaac    1680
atgaaccgct ccggcagtat aagctatggc agcttccatg acactcagca ggtgcatagt    1740
cccggtattg gtacgccttt tgggagcatg gatggcttta tgagttctgc ccgcgtgaac    1800
agcccgatgg tggcgacacc aatggcatcg acgcccatga tgcccagtcc catggccgct    1860
ccgggagtgc ctggtacccc tggattcgag atttggcgac ctcctccctc gatgactccc    1920
```

-continued

```
aaacctgaac cctctcaaat caccaaccca gccaatttcg gcggctattt cagacctcca    1980
gtgccgacga ctcccaagcc ggtagtcaac acaggtaatc agttcatctt ggaattcaac    2040
cccagcgcca aggcagccaa agggaaagct ccggcaaagc ctcccaggcc tcgattgcct    2100
cctcggaaac ccaaccttc acaatcacaa ctctcggcac aaacaccagc agcacctgtg     2160
caagcgtcgg tttcaacacc ggcaccggca tcggcaccga caccgacacc agccgttgcc   2220
tcaactccag gtccaatgtc tcctcctcct aaaccgcctc gcccttcaga accgtcttct    2280
tcatccacac ccattgttgt gagcaatgcc gctaaaccaa gagaatcctt gcagctaggt    2340
gtactaacgc gcatgtctag gcacagcggc gggattcgat ggctcttcgt gcccaggcag   2400
gtactaggcc gtcacgggaa caggttcctg cagaggcctg ggagcaatac aaatccacta   2460
tccgtacccct ctatctcgag gagagaaaac ccttgaaaga agtcatgagt gtcatggctg  2520
aacaatatgg gtttcaagca cgtgagtcg aagattgatt cctcttctgc ttcatcgttc    2580
gggttcttgg ttcgttgtaa actaattcga cgccctttct aggccaaaga tgtataaaac   2640
aaggttctct caatggggtt ttgtgaagaa taacacggag gaagaagtga aacggctgtt   2700
gtcgatgaag ttccagcgag atgccgaggg caaagtttcc gagtttgttc gaaacggcag   2760
ggtggtgaac ctaggtacct atttgaaacg gaaaggagtg acggagtatg acctcgttga   2820
tttcgaacta ccggccgacc ttccagcaca tatccgatgc agaacaccga caccacctcc   2880
ggctctgcga tcacccgatc tgctccgtgc acaggaggta gtcgttggaa atatgcgcaa   2940
ggcattccta cactgtcggc aattcgagat ggagactgag actcagattg gttggccatc   3000
aaccatggtt tgggggtgctg gatcgagtga actcctggtc gaggccaact tttacttcga   3060
agctcgcgac gcagatcaag gcggtgacta cctgatgcga gctttcaagc agctcgagct    3120
ggacctcaga aagctctcgc cacaaggcat catggaacta tcctgggta tgatcaatcg     3180
ggatcccggc atgatgacgg cccttttgcaa gtaccttgca gcatattcga caaccaatct   3240
ggagcgaacc catcctctcc ggcaaatctt cacttgtctg tatgaagtgc aacaaaagca   3300
tggggcgcag acgttgtctg agctcctgtg gactagcatc tcgacaattg cggaggaact   3360
cgaggccatc tatggacgca agcatccgta tgtggctcgc acatgggccg atcttgcgct   3420
gttttacagc caggtgaacc cggaaaggct ggagaagttg gttgttgagc ttcgtgtgct    3480
ccagaggcag ctcgagcaac gacatgggca ttccagtgtc gaagtggttt ccatccgata   3540
tgccattctg ctgttggtct atgcgtcgtc tccccagtcg gatgcctcga agcaagccgc   3600
aaatgattat tggaacctgc tgcggaatat gaacaccatg tttcccatgc gcgactcccg   3660
tccgaatagt tactgctatc acagcccgct caaggtcgat ccgtggacaa agaggtgccg   3720
caggcggtac gacacactcg tcaccatatt cgaggagcat gtaggcgtta gaatcaatcc   3780
ctatttcgaa gaggacttcc acacgaccga gcacgctcaa gaaacgcagg atgcctgggc   3840
ggcagctctg caaatggggtt cgacgaatag atcttgggggc ttcatctagc ggtttcgctt   3900
tcagaatgtt gggtgtgttc cacgcccagc tggcgcaaat gtcaggtacc caagatacct   3960
tgtctctcgt ctcctagcgc gcggtgcagc gagcttcttt ttcgagattt ctttttccgg   4020
aatctagcgg gcggttaata cccagcatca gaaggattgc ggcgcatcta cctagcgaca   4080
gttttttcg gttacgtcct gttttgccacc tcacatcgag cctggagttt tggacagttg    4140
acaattctcg ccatcgcgga acatttcct ttctcatgtc gccgacgctg acaagtcgat     4200
ttccttggtc tttccacgca agttgttgca cctctcgagc cgggcgttag ggagggcctt   4260
ttccccttg gatgcgtcgt catccgtgta taatagtatc cgttgttttc tgttttcctt     4320
```

-continued

| | |
|---|---|
| tcctgcgttt gatatgcgat gttcagcttt cttgatactg aagaccacga gggagaggcg | 4380 |
| ggaaacgagt gttttgaaag aagttggcag tcagactttt tttgttacag ggcgaacgag | 4440 |
| gagttgacgg gaattgagca gaagaaaaaa aataccttta tcgagcattt cctgcttcat | 4500 |
| cgggaaggag aaggcaggcc ggagtttgga tggcaggaac ggacgaggca cttgtcgatt | 4560 |
| gtcgtcattg cagatggtta gaccagaccg accgtccttc tgggaaggag cgggagcaca | 4620 |
| ctgattttct catcgcgcct tcttttcgac ttgacttgcc gttagtataa aaaacttcaa | 4680 |
| ctggtattaa tgaataaaga catgatgaca | 4710 |

<210> SEQ ID NO 12
<211> LENGTH: 4082
<212> TYPE: DNA
<213> ORGANISM: Trichoderma reesei

<400> SEQUENCE: 12

| | |
|---|---|
| ccagaacagc tccgtcctgg cccagcctgt attttgagca tctctggctc tcttatctca | 60 |
| gcgggggcct tctaaattga cccttctcga aagacggcac atgggatttc ccttcttggc | 120 |
| actctagacg agggaacttt tgctcgctct cttcgctgcg tggcttggct tggtttcctc | 180 |
| ccacgccgct gctgatgctt ttggagctgg ctgctcttgt tgtttgtttg tccaaaccac | 240 |
| acagcggctg ttgccctatc aaggcgtttt cccacatcgg ccgatatctg ggggaacgat | 300 |
| acggatatct gcccctagcc agccagccag ccagccagcc agccagccag cccttgcctg | 360 |
| tactttcgtg ctgcgcccgt cccagtaggc ctctccgccg ccgtgattcc ctctctcttt | 420 |
| actatccctc tacaccaggc gattatgggc acctttgccc gcctcccata cacgaccttc | 480 |
| gtttgactga gcaagcacgc tcgccactct cagagagtga tgaatcaccg cgctggagac | 540 |
| tgattattcc agccgagtcc tacgacttgc ccaggtccgt cagttcctga cagacaagac | 600 |
| agccggcgga ctgagcacca ctgctctgtc tgctcggtgt gtgggcacgt tgacatgttc | 660 |
| catcaaccgc cggaaaagcc tcgcgcgcct ggcttcgacg atgatccgtt cgggtttgtc | 720 |
| acccaggcct gggagagata tggcctgggc agtgtgtcgt cgcctccgcc tgcgatgcct | 780 |
| ccgcagccca tccagaggac cggacgggcc tattccaccg cttcggtaat ggactggacg | 840 |
| cccgagatcg ataccacctt tcaccaccac ggcgacggag tggccatgtc gccggtggaa | 900 |
| cacgtcgaac tggacagcct tggttcgcct cagggagggg gaggggttgg ccgcttggtc | 960 |
| gcgcactttg agaataaagg ctatgtcccg ccattgcctc cgcggcccat caacaatcag | 1020 |
| ccgcatcaac cgcatcacat gggccacagt ccttcaatgt cgtcgcagtt tggcagtcta | 1080 |
| aactctgtag cccatacgca taggatatcg agtcccgttg ctagcccagg tgaatcccaa | 1140 |
| tatggctcgc tcggggtgca ttcgccccca acacccacct caatcgtcac caacatgaac | 1200 |
| cgctccggca gtataagcta tggcagcttc catgacactc agcaggtgca tagtcccggt | 1260 |
| attggtacgc cttttgggag catggatggc tttatgagtt ctgcccgcgt gaacagcccg | 1320 |
| atggtggcga caccaatggc atcgacgccc atgatgccca gtccatggcc gctccggga | 1380 |
| gtgcctggta cccctggatt cgagatttgg cgacctcctc cctcgatgac tcccaaacct | 1440 |
| gaaccctctc aaatcaccaa cccagccaat ttcggcggct atttcagacc tccagtgccg | 1500 |
| acgactccca agccggtagt caacacaggt aatcagttca tcttggaatt caaccccagc | 1560 |
| gccaaggcag ccaaagggaa agctccggca aagcctccca ggcctcgatt gcctcctcgg | 1620 |
| aaacccaacc tttcacaatc acaactctcg gcacaaacac cagcagcacc tgtgcaagcg | 1680 |

-continued

| | |
|---|---|
| tcggtttcaa caccggcacc ggcatcggca ccgacaccga caccagccgt tgcctcaact | 1740 |
| ccaggtccaa tgtctcctcc tcctaaaccg cctcgccctt cagaaccgtc ttcttcatcc | 1800 |
| acacccattg ttgcacagcg gcgggattcg atggctcttc gtgcccaggc aggtactagg | 1860 |
| ccgtcacggg aacaggttcc tgcagaggcc tgggagcaat acaaatccac tatccgtacc | 1920 |
| ctctatctcg aggagagaaa acccttgaaa gaagtcatga gtgtcatggc tgaacaatat | 1980 |
| gggtttcaag caacgccaaa gatgtataaa acaaggttct ctcaatgggg ttttgtgaag | 2040 |
| aataacacgg aggaagaagt gaaacggctg ttgtcgatga agttccagcg agatgccgag | 2100 |
| ggcaaagttt ccgagtttgt tcgaaacggc agggtggtga acctaggtac ctatttgaaa | 2160 |
| cggaaaggag tgacggagta tgacctcgtt gatttcgaac taccggccga ccttccagca | 2220 |
| catatccgat gcagaacacc gacaccacct ccggctctgc gatcaccgga tctgctccgt | 2280 |
| gcacaggagg tagtcgttgg aaatatgcgc aaggcattcc tacactgtcg gcaattcgag | 2340 |
| atggagactg agactcagat tggttggcca tcaaccatgg tttggggtgc tggatcgagt | 2400 |
| gaactcctgg tcgaggccaa cttttacttc gaagctcgcg acgcagatca aggcggtgac | 2460 |
| tacctgatgc gagcttttcaa gcagctcgag ctggacctca gaaagctctc gccacaaggc | 2520 |
| atcatggaac taatcctggg tatgatcaat cgggatcccg gcatgatgac ggcccttttgc | 2580 |
| aagtaccttg cagcatattc gacaaccaat ctggagcgaa cccatcctct ccggcaaatc | 2640 |
| ttcacttgtc tgtatgaagt gcaacaaaag catgggcgc agacgttgtc tgagctcctg | 2700 |
| tggactagca tctcgacaat tgcggaggaa ctcgaggcca tctatggacg caagcatccg | 2760 |
| tatgtggctc gcacatgggc cgatcttgcg ctgtttaca gccaggtgaa cccggaaagg | 2820 |
| ctggagaagt tggttgttga gcttcgtgtg ctccagaggc agctcgagca acgacatggg | 2880 |
| cattccagtg tcgaagtggt ttccatccga tatgccattc tgctgttggt ctatgcgtcg | 2940 |
| tctcccccagt cggatgcctc gaagcaagcc gcaaatgatt attggaacct gctgcggaat | 3000 |
| atgaacacca tgtttcccat gcgcgactcc cgtccgaata gttactgcta tcacagcccg | 3060 |
| ctcaaggtcg atccgtggac aaagaggtgc cgcaggcggt acgacacact cgtcaccata | 3120 |
| ttcgaggagc atgtaggcgt tagaatcaat ccctatttcg aagaggactt ccacacgacc | 3180 |
| gagcacgctc aagaaacgca ggatgcctgg gcggcagctc tgcaaatggg ttcgacgaat | 3240 |
| agatcttggg gcttcatcta gcggtttcgc tttcagaatg ttgggtgtgt tccacgccca | 3300 |
| gctggcgcaa atgtcaggta cccaagatac cttgtctctc gtctcctagc gcgcggtgca | 3360 |
| gcgagcttct ttttcgagat ttcttttttcc ggaatctagc gggcggttaa tacccagcat | 3420 |
| cagaaggatt gcggcgcatc tacctagcga cagttttttt cggttacgtc ctgtttgcca | 3480 |
| cctcacatcg agcctggagt tttggacagt tgacaattct cgccatcgcg gaacattttc | 3540 |
| ctttctcatg tcgccgacgc tgacaagtcg atttccttgg tctttccacg caagttgttg | 3600 |
| cacctctcga gccgggcgtt agggagggc ttttcccct tggatgcgtc gtcatccgtg | 3660 |
| tataatagta tccgttgttt tctgttttcc tttcctgcgt ttgatatgcg atgttcagct | 3720 |
| ttcttgatac tgaagaccac gagggagagg cgggaaacga gtgttttgaa agaagttggc | 3780 |
| agtcagactt tttttgttac agggcgaacg aggagttgac gggaattgag cagaagaaaa | 3840 |
| aaaatacctt tatcgagcat ttcctgcttc atcgggaagg agaaggcagg ccggagtttg | 3900 |
| gatggcagga acggacgagg cacttgtcga ttgtcgtcat tgcagatggt tagaccagac | 3960 |
| cgaccgtcct tctgggaagg agcgggagca cactgatttt ctcatcgcgc cttctttcg | 4020 |
| acttgacttg ccgttagtat aaaaaacttc aactggtatt aatgaataaa gacatgatga | 4080 | ca 4082

<210> SEQ ID NO 13
<211> LENGTH: 868
<212> TYPE: PRT
<213> ORGANISM: Trichoderma reesei

<400> SEQUENCE: 13

```
Met Phe His Gln Pro Pro Glu Lys Pro Arg Ala Pro Gly Phe Asp Asp
1               5                   10                  15

Asp Pro Phe Gly Phe Val Thr Gln Ala Trp Glu Arg Tyr Gly Leu Gly
                20                  25                  30

Ser Val Ser Ser Pro Pro Ala Met Pro Pro Gln Pro Ile Gln Arg
            35                  40                  45

Thr Gly Arg Ala Tyr Ser Thr Ala Ser Val Met Asp Trp Thr Pro Glu
    50                  55                  60

Ile Asp Thr Thr Phe His His His Gly Asp Gly Val Ala Met Ser Pro
65                  70                  75                  80

Val Glu His Val Glu Leu Asp Ser Leu Gly Ser Pro Gln Gly Gly Gly
                85                  90                  95

Gly Val Gly Arg Leu Val Ala His Phe Glu Asn Lys Gly Tyr Val Pro
            100                 105                 110

Pro Leu Pro Pro Arg Pro Ile Asn Asn Gln Pro His Gln Pro His His
        115                 120                 125

Met Gly His Ser Pro Ser Met Ser Ser Gln Phe Gly Ser Leu Asn Ser
130                 135                 140

Val Ala His Thr His Arg Ile Ser Ser Pro Val Ala Ser Pro Gly Glu
145                 150                 155                 160

Ser Gln Tyr Gly Ser Leu Gly Val His Ser Pro Pro Thr Pro Thr Ser
                165                 170                 175

Ile Val Thr Asn Met Asn Arg Ser Gly Ser Ile Ser Tyr Gly Ser Phe
            180                 185                 190

His Asp Thr Gln Gln Val His Ser Pro Gly Ile Gly Thr Pro Phe Gly
        195                 200                 205

Ser Met Asp Gly Phe Met Ser Ser Ala Arg Val Asn Ser Pro Met Val
210                 215                 220

Ala Thr Pro Met Ala Ser Thr Pro Met Met Pro Ser Pro Met Ala Ala
225                 230                 235                 240

Pro Gly Val Pro Gly Thr Pro Gly Phe Glu Ile Trp Arg Pro Pro
                245                 250                 255

Ser Met Thr Pro Lys Pro Glu Pro Ser Gln Ile Thr Asn Pro Ala Asn
            260                 265                 270

Phe Gly Gly Tyr Phe Arg Pro Pro Val Pro Thr Thr Pro Lys Pro Val
        275                 280                 285

Val Asn Thr Gly Asn Gln Phe Ile Leu Glu Phe Asn Pro Ser Ala Lys
290                 295                 300

Ala Ala Lys Gly Lys Ala Pro Ala Lys Pro Pro Arg Pro Arg Leu Pro
305                 310                 315                 320

Pro Arg Lys Pro Asn Leu Ser Gln Ser Gln Leu Ser Ala Gln Thr Pro
                325                 330                 335

Ala Ala Pro Val Gln Ala Ser Val Ser Thr Pro Ala Pro Ala Ser Ala
            340                 345                 350

Pro Thr Pro Thr Pro Ala Val Ala Ser Thr Pro Gly Pro Met Ser Pro
        355                 360                 365
```

```
Pro Pro Lys Pro Pro Arg Pro Ser Glu Pro Ser Ser Ser Thr Pro
    370             375             380
Ile Val Ala Gln Arg Arg Asp Ser Met Ala Leu Arg Ala Gln Ala Gly
385             390             395             400
Thr Arg Pro Ser Arg Glu Gln Val Pro Ala Glu Ala Trp Glu Gln Tyr
            405             410             415
Lys Ser Thr Ile Arg Thr Leu Tyr Leu Glu Glu Arg Lys Pro Leu Lys
            420             425             430
Glu Val Met Ser Val Met Ala Glu Gln Tyr Gly Phe Gln Ala Thr Pro
        435             440             445
Lys Met Tyr Lys Thr Arg Phe Ser Gln Trp Gly Phe Val Lys Asn Asn
450             455             460
Thr Glu Glu Val Lys Arg Leu Leu Ser Met Lys Phe Gln Arg Asp
465             470             475             480
Ala Glu Gly Lys Val Ser Glu Phe Val Arg Asn Gly Arg Val Val Asn
            485             490             495
Leu Gly Thr Tyr Leu Lys Arg Lys Gly Val Thr Glu Tyr Asp Leu Val
            500             505             510
Asp Phe Glu Leu Pro Ala Asp Leu Pro Ala His Ile Arg Cys Arg Thr
        515             520             525
Pro Thr Pro Pro Pro Ala Leu Arg Ser Pro Asp Leu Leu Arg Ala Gln
    530             535             540
Glu Val Val Val Gly Asn Met Arg Lys Ala Phe Leu His Cys Arg Gln
545             550             555             560
Phe Glu Met Glu Thr Glu Thr Gln Ile Gly Trp Pro Ser Thr Met Val
            565             570             575
Trp Gly Ala Gly Ser Ser Glu Leu Leu Val Glu Ala Asn Phe Tyr Phe
            580             585             590
Glu Ala Arg Asp Ala Asp Gln Gly Gly Asp Tyr Leu Met Arg Ala Phe
        595             600             605
Lys Gln Leu Glu Leu Asp Leu Arg Lys Leu Ser Pro Gln Gly Ile Met
    610             615             620
Glu Leu Ile Leu Gly Met Ile Asn Arg Asp Pro Gly Met Met Thr Ala
625             630             635             640
Leu Cys Lys Tyr Leu Ala Ala Tyr Ser Thr Thr Asn Leu Glu Arg Thr
            645             650             655
His Pro Leu Arg Gln Ile Phe Thr Cys Leu Tyr Glu Val Gln Gln Lys
            660             665             670
His Gly Ala Gln Thr Leu Ser Glu Leu Leu Trp Thr Ser Ile Ser Thr
        675             680             685
Ile Ala Glu Glu Leu Glu Ala Ile Tyr Gly Arg Lys His Pro Tyr Val
    690             695             700
Ala Arg Thr Trp Ala Asp Leu Ala Leu Phe Tyr Ser Gln Val Asn Pro
705             710             715             720
Glu Arg Leu Glu Lys Leu Val Val Glu Leu Arg Val Leu Gln Arg Gln
            725             730             735
Leu Glu Gln Arg His Gly His Ser Ser Val Glu Val Val Ser Ile Arg
            740             745             750
Tyr Ala Ile Leu Leu Leu Val Tyr Ala Ser Ser Pro Gln Ser Asp Ala
        755             760             765
Ser Lys Gln Ala Ala Asn Asp Tyr Trp Asn Leu Leu Arg Asn Met Asn
    770             775             780
```

```
Thr Met Phe Pro Met Arg Asp Ser Arg Pro Asn Ser Tyr Cys Tyr His
785                 790                 795                 800

Ser Pro Leu Lys Val Asp Pro Trp Thr Lys Arg Cys Arg Arg Arg Tyr
            805                 810                 815

Asp Thr Leu Val Thr Ile Phe Glu Glu His Val Gly Val Arg Ile Asn
                820                 825                 830

Pro Tyr Phe Glu Glu Asp Phe His Thr Thr Glu His Ala Gln Glu Thr
            835                 840                 845

Gln Asp Ala Trp Ala Ala Leu Gln Met Gly Ser Thr Asn Arg Ser
850                 855                 860

Trp Gly Phe Ile
865

<210> SEQ ID NO 14
<211> LENGTH: 288
<212> TYPE: PRT
<213> ORGANISM: Trichoderma reesei

<400> SEQUENCE: 14

Met Phe His Gln Pro Pro Glu Lys Pro Arg Ala Pro Gly Phe Asp Asp
1               5                   10                  15

Asp Pro Phe Gly Phe Val Thr Gln Ala Trp Glu Arg Tyr Gly Leu Gly
                20                  25                  30

Ser Val Ser Ser Pro Pro Ala Met Pro Gln Pro Ile Gln Arg
            35                  40                  45

Thr Gly Arg Ala Tyr Ser Thr Ala Ser Val Met Asp Trp Thr Pro Glu
    50                  55                  60

Ile Asp Thr Thr Phe His His His Gly Asp Gly Val Ala Met Ser Pro
65                  70                  75                  80

Val Glu His Val Glu Leu Asp Ser Leu Gly Ser Pro Gln Gly Gly Gly
                85                  90                  95

Gly Val Gly Arg Leu Val Ala His Phe Glu Asn Lys Gly Tyr Val Pro
            100                 105                 110

Pro Leu Pro Pro Arg Pro Ile Asn Asn Gln Pro His Gln Pro His His
            115                 120                 125

Met Gly His Ser Pro Ser Met Ser Ser Gln Phe Gly Ser Leu Asn Ser
130                 135                 140

Val Ala His Thr His Arg Ile Ser Ser Pro Val Ala Ser Pro Gly Glu
145                 150                 155                 160

Ser Gln Tyr Gly Ser Leu Gly Val His Ser Pro Pro Thr Pro Thr Ser
                165                 170                 175

Ile Val Thr Asn Met Asn Arg Ser Gly Ser Ile Ser Tyr Gly Ser Phe
            180                 185                 190

His Asp Thr Gln Gln Val His Ser Pro Gly Ile Gly Thr Pro Phe Gly
        195                 200                 205

Ser Met Asp Gly Phe Met Ser Ser Ala Arg Val Asn Ser Pro Met Val
210                 215                 220

Ala Thr Pro Met Ala Ser Thr Pro Met Met Pro Ser Pro Met Ala Ala
225                 230                 235                 240

Pro Gly Val Pro Gly Thr Pro Gly Phe Glu Ile Trp Arg Pro Pro
                245                 250                 255

Ser Met Thr Pro Lys Pro Glu Pro Ser Gln Ile Thr Asn Pro Ala Asn
            260                 265                 270

Phe Gly Gly Tyr Phe Arg Pro Pro Gln Cys Arg Arg Leu Pro Ser Arg
            275                 280                 285
```

<210> SEQ ID NO 15
<211> LENGTH: 387
<212> TYPE: PRT
<213> ORGANISM: Trichoderma reesei

<400> SEQUENCE: 15

Met Phe His Gln Pro Pro Glu Lys Pro Arg Ala Pro Gly Phe Asp Asp
1               5                   10                  15

Asp Pro Phe Gly Phe Val Thr Gln Ala Trp Glu Arg Tyr Gly Leu Gly
            20                  25                  30

Ser Val Ser Ser Pro Pro Ala Met Pro Gln Pro Ile Gln Arg
        35                  40                  45

Thr Gly Arg Ala Tyr Ser Thr Ala Ser Val Met Asp Trp Thr Pro Glu
    50                  55                  60

Ile Asp Thr Thr Phe His His His Gly Asp Gly Val Ala Met Ser Pro
65                  70                  75                  80

Val Glu His Val Glu Leu Asp Ser Leu Gly Ser Pro Gln Gly Gly Gly
                85                  90                  95

Gly Val Gly Arg Leu Val Ala His Phe Glu Asn Lys Gly Tyr Val Pro
            100                 105                 110

Pro Leu Pro Pro Arg Pro Ile Asn Asn Gln Pro His Gln Pro His His
        115                 120                 125

Met Gly His Ser Pro Ser Met Ser Ser Gln Phe Gly Ser Leu Asn Ser
    130                 135                 140

Val Ala His Thr His Arg Ile Ser Ser Pro Val Ala Ser Pro Gly Glu
145                 150                 155                 160

Ser Gln Tyr Gly Ser Leu Gly Val His Ser Pro Pro Thr Pro Thr Ser
                165                 170                 175

Ile Val Thr Asn Met Asn Arg Ser Gly Ser Ile Ser Tyr Gly Ser Phe
            180                 185                 190

His Asp Thr Gln Gln Val His Ser Pro Gly Ile Gly Thr Pro Phe Gly
        195                 200                 205

Ser Met Asp Gly Phe Met Ser Ser Ala Arg Val Asn Ser Pro Met Val
    210                 215                 220

Ala Thr Pro Met Ala Ser Thr Pro Met Met Pro Ser Pro Met Ala Ala
225                 230                 235                 240

Pro Gly Val Pro Gly Thr Pro Gly Phe Glu Ile Trp Arg Pro Pro Pro
                245                 250                 255

Ser Met Thr Pro Lys Pro Glu Pro Ser Gln Ile Thr Asn Pro Ala Asn
            260                 265                 270

Phe Gly Gly Tyr Phe Arg Pro Pro Val Pro Thr Thr Pro Lys Pro Val
        275                 280                 285

Val Asn Thr Gly Asn Gln Phe Ile Leu Glu Phe Asn Pro Ser Ala Lys
    290                 295                 300

Ala Ala Lys Gly Lys Ala Pro Ala Lys Pro Pro Arg Pro Arg Leu Pro
305                 310                 315                 320

Pro Arg Lys Pro Asn Leu Ser Gln Ser Gln Leu Ser Ala Gln Thr Pro
                325                 330                 335

Ala Ala Pro Val Gln Ala Ser Val Ser Thr Pro Ala Pro Ala Ser Ala
            340                 345                 350

Pro Thr Pro Thr Pro Ala Val Ala Ser Thr Gly Pro Met Ser Pro
        355                 360                 365

Pro Pro Lys Pro Pro Arg Pro Ser Glu Pro Ser Ser Ser Ser Thr Pro

```
            370                 375                 380
Ile Val Ala
385

<210> SEQ ID NO 16
<211> LENGTH: 430
<212> TYPE: PRT
<213> ORGANISM: Trichoderma reesei

<400> SEQUENCE: 16

Met Phe His Gln Pro Pro Glu Lys Pro Arg Ala Pro Gly Phe Asp Asp
1               5                   10                  15

Asp Pro Phe Gly Phe Val Thr Gln Ala Trp Glu Arg Tyr Gly Leu Gly
            20                  25                  30

Ser Val Ser Ser Pro Pro Pro Ala Met Pro Gln Pro Ile Gln Arg
        35                  40                  45

Thr Gly Arg Ala Tyr Ser Thr Ala Ser Val Met Asp Trp Thr Pro Glu
    50                  55                  60

Ile Asp Thr Thr Phe His His Gly Asp Gly Val Ala Met Ser Pro
65                  70                  75                  80

Val Glu His Val Glu Leu Asp Ser Leu Gly Ser Pro Gln Gly Gly Gly
                85                  90                  95

Gly Val Gly Arg Leu Val Ala His Phe Glu Asn Lys Gly Tyr Val Pro
            100                 105                 110

Pro Leu Pro Pro Arg Pro Ile Asn Asn Gln Pro His Gln Pro His His
        115                 120                 125

Met Gly His Ser Pro Ser Met Ser Ser Gln Phe Gly Ser Leu Asn Ser
130                 135                 140

Val Ala His Thr His Arg Ile Ser Ser Pro Val Ala Ser Pro Gly Glu
145                 150                 155                 160

Ser Gln Tyr Gly Ser Leu Gly Val His Ser Pro Pro Thr Pro Thr Ser
                165                 170                 175

Ile Val Thr Asn Met Asn Arg Ser Gly Ser Ile Ser Tyr Gly Ser Phe
            180                 185                 190

His Asp Thr Gln Gln Val His Ser Pro Gly Ile Gly Thr Pro Phe Gly
        195                 200                 205

Ser Met Asp Gly Phe Met Ser Ser Ala Arg Val Asn Ser Pro Met Val
210                 215                 220

Ala Thr Pro Met Ala Ser Thr Pro Met Met Pro Ser Pro Met Ala Ala
225                 230                 235                 240

Pro Gly Val Pro Gly Thr Pro Gly Phe Glu Ile Trp Arg Pro Pro Pro
                245                 250                 255

Ser Met Thr Pro Lys Pro Glu Pro Ser Gln Ile Thr Asn Pro Ala Asn
            260                 265                 270

Phe Gly Gly Tyr Phe Arg Pro Pro Val Pro Thr Thr Pro Lys Pro Val
        275                 280                 285

Val Asn Thr Gly Asn Gln Phe Ile Leu Glu Phe Asn Pro Ser Ala Lys
290                 295                 300

Ala Ala Lys Gly Lys Ala Pro Ala Lys Pro Pro Arg Pro Arg Leu Pro
305                 310                 315                 320

Pro Arg Asn Pro Thr Phe His Asn His Asn Ser Arg His Lys His Gln
                325                 330                 335

Gln His Leu Cys Lys Arg Arg Phe Gln His Arg His Arg His Arg His
            340                 345                 350
```

```
Arg His Arg His Gln Pro Leu Pro Gln Leu Gln Val Gln Cys Leu Leu
            355                 360                 365

Leu Leu Asn Arg Leu Ala Leu Gln Asn Arg Leu Leu His Pro His Pro
        370                 375                 380

Leu Leu His Ser Gly Gly Ile Arg Trp Leu Phe Val Pro Arg Gln Val
385                 390                 395                 400

Leu Gly Arg His Gly Asn Arg Phe Leu Gln Arg Pro Gly Ser Asn Thr
                405                 410                 415

Asn Pro Leu Ser Val Pro Ser Ile Ser Arg Arg Glu Asn Pro
            420                 425                 430

<210> SEQ ID NO 17
<211> LENGTH: 317
<212> TYPE: PRT
<213> ORGANISM: Trichoderma reesei

<400> SEQUENCE: 17

Met Phe His Gln Pro Pro Glu Lys Pro Arg Ala Pro Gly Phe Asp Asp
1               5                   10                  15

Asp Pro Phe Gly Phe Val Thr Gln Ala Trp Glu Arg Tyr Gly Leu Gly
            20                  25                  30

Ser Val Ser Ser Pro Pro Ala Met Pro Gln Pro Ile Gln Arg
        35                  40                  45

Thr Gly Arg Ala Tyr Ser Thr Ala Ser Val Met Asp Trp Thr Pro Glu
    50                  55                  60

Ile Asp Thr Thr Phe His His His Gly Asp Gly Val Ala Met Ser Pro
65                  70                  75                  80

Val Glu His Val Glu Leu Asp Ser Leu Gly Ser Pro Gln Gly Gly Gly
                85                  90                  95

Gly Val Gly Arg Leu Val Ala His Phe Glu Asn Lys Gly Tyr Val Pro
            100                 105                 110

Pro Leu Pro Pro Arg Pro Ile Asn Asn Gln Pro His Gln Pro His His
        115                 120                 125

Met Gly His Ser Pro Ser Met Ser Ser Gln Phe Gly Ser Leu Asn Ser
    130                 135                 140

Val Ala His Thr His Arg Ile Ser Ser Pro Val Ala Ser Pro Gly Glu
145                 150                 155                 160

Ser Gln Tyr Gly Ser Leu Gly Val His Ser Pro Pro Thr Pro Thr Ser
                165                 170                 175

Ile Val Thr Asn Met Asn Arg Ser Gly Ser Ile Ser Tyr Gly Ser Phe
            180                 185                 190

His Asp Thr Gln Gln Val His Ser Pro Gly Ile Gly Thr Pro Phe Gly
        195                 200                 205

Ser Met Asp Gly Phe Met Ser Ser Ala Arg Val Asn Ser Pro Met Val
    210                 215                 220

Ala Thr Pro Met Ala Ser Thr Pro Met Met Pro Ser Pro Met Ala Ala
225                 230                 235                 240

Pro Gly Val Pro Gly Thr Pro Gly Phe Glu Ile Trp Arg Pro Pro
                245                 250                 255

Ser Met Thr Pro Lys Pro Glu Pro Ser Gln Ile Thr Asn Pro Ala Asn
            260                 265                 270

Phe Gly Gly Tyr Phe Arg Pro Pro Val Pro Thr Thr Pro Lys Pro Val
        275                 280                 285

Val Asn Thr Gly Asn Gln Phe Ile Leu Glu Phe Asn Pro Ser Ala Lys
    290                 295                 300
```

```
Ala Ala Lys Gly Lys Ala Pro Ala Lys Pro Pro Arg Pro
305                 310                 315
```

<210> SEQ ID NO 18
<211> LENGTH: 297
<212> TYPE: PRT
<213> ORGANISM: Trichoderma reesei

<400> SEQUENCE: 18

```
Met Phe His Gln Pro Pro Glu Lys Pro Arg Ala Pro Gly Phe Asp Asp
1               5                   10                  15

Asp Pro Phe Gly Phe Val Thr Gln Ala Trp Glu Arg Tyr Gly Leu Gly
            20                  25                  30

Ser Val Ser Ser Pro Pro Ala Met Pro Pro Gln Pro Ile Gln Arg
        35                  40                  45

Thr Gly Arg Ala Tyr Ser Thr Ala Ser Val Met Asp Trp Thr Pro Glu
    50                  55                  60

Ile Asp Thr Thr Phe His His His Gly Asp Gly Val Ala Met Ser Pro
65                  70                  75                  80

Val Glu His Val Glu Leu Asp Ser Leu Gly Ser Pro Gln Gly Gly
                85                  90                  95

Gly Val Gly Arg Leu Val Ala His Phe Glu Asn Lys Gly Tyr Val Pro
            100                 105                 110

Pro Leu Pro Pro Arg Pro Ile Asn Asn Gln Pro His Gln Pro His His
            115                 120                 125

Met Gly His Ser Pro Ser Met Ser Ser Gln Phe Gly Ser Leu Asn Ser
130                 135                 140

Val Ala His Thr His Arg Ile Ser Ser Pro Val Ala Ser Pro Gly Glu
145                 150                 155                 160

Ser Gln Tyr Gly Ser Leu Gly Val His Ser Pro Pro Thr Pro Thr Ser
                165                 170                 175

Ile Val Thr Asn Met Asn Arg Ser Gly Ser Ile Ser Tyr Gly Ser Phe
            180                 185                 190

His Asp Thr Gln Gln Val His Ser Pro Gly Ile Gly Thr Pro Phe Gly
            195                 200                 205

Ser Met Asp Gly Phe Met Ser Ser Ala Arg Val Asn Ser Pro Met Val
210                 215                 220

Ala Thr Pro Met Ala Ser Thr Pro Met Met Pro Ser Pro Met Ala Ala
225                 230                 235                 240

Pro Gly Val Pro Gly Thr Pro Gly Phe Glu Ile Trp Arg Pro Pro
                245                 250                 255

Ser Met Thr Pro Lys Pro Glu Pro Ser Gln Ile Thr Asn Pro Ala Asn
            260                 265                 270

Phe Gly Gly Tyr Phe Arg Pro Pro Val Pro Thr Thr Pro Lys Pro Val
        275                 280                 285

Val Asn Thr Gly Asn Gln Phe Ile Leu
    290                 295
```

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19

```
cgttggctcg aggcaactgc                                              20
```

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20

```
tgtcatcatg tctttattca                                              20
```

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21

```
ccagaacagc tccgtcctgg                                              20
```

<210> SEQ ID NO 22
<211> LENGTH: 887
<212> TYPE: PRT
<213> ORGANISM: Fusarium oxysporum

<400> SEQUENCE: 22

```
Met Phe Asn His Ser Ala Gly Gly Pro Arg Pro Ser Asp Asn Asn Glu
1               5                   10                  15

Asp Pro Ser Tyr Gly Phe Ala Asp Gln Gly Trp His Arg Phe Thr Met
            20                  25                  30

Asn Asn Asn Asn Thr Asn Ser Phe Ser Ala Gly Asn Ser Gln Ser Tyr
        35                  40                  45

His Asp Ala Gly Ala Ser Tyr Gly Asp Ser Ser Gly Met Asp Trp Ala
    50                  55                  60

Pro Thr Pro Ser Ala Glu Tyr Asp Leu Arg Phe Asp Gln His Asp His
65                  70                  75                  80

Met Ser Gln Asp Val Glu Leu Asp Asn Met Ser Ser Ser His Gly Gly
                85                  90                  95

Gly Gly Gly Val Gly Arg Leu Val Ala His Phe Glu Asn Lys Ser Phe
            100                 105                 110

Ala Pro Pro Leu Pro Pro Arg Pro Ser Asn Val Val Thr Ser Pro Val
        115                 120                 125

His Gln Glu Pro Pro Val Ser Ser Pro Phe Gly Asn Phe Ser Val Thr
    130                 135                 140

Ser Pro Ile Val Thr Ser Pro Leu Ala Ser Pro Ala Glu Pro Asn Tyr
145                 150                 155                 160

Gly Leu Leu Ser Gly His Ser Arg Val Thr Ser Pro Ile Val Ser Pro
                165                 170                 175

Pro Pro Ala Leu Ala Phe Gly Phe His Asp Ile Pro Val His Ser
            180                 185                 190

Pro Gly Val Gly Ser Ser Ser Gly Pro Phe Gly Asn Met Asn Ser Phe
        195                 200                 205

Met Val Asn Asn Asn Arg Val Thr Thr Pro Met Glu Thr Ala Ser Met
    210                 215                 220

Ala Gly Pro Pro Met Met Pro Asn Ser Gly Met Asn Ala Lys Val Thr
225                 230                 235                 240
```

```
Ser Pro Gly Ser Val Thr Pro Gly Val Pro Gly Thr Pro Gly Phe Ala
            245                 250                 255

Ile Trp Arg Pro Pro Val Pro Thr Thr Ser Lys Pro Ser Leu Asp Gln
        260                 265                 270

Pro Gln Gly Ser Ser Thr Ser Ser Asn Ser Gly Tyr Phe Ala Lys Pro
            275                 280                 285

Pro Ile Pro Ser Thr Pro Lys Pro Val Met Asn Ala Gly Ser Gln Leu
        290                 295                 300

Val Leu Asp Phe Asn Thr Asn Ser Thr Phe Asn Ala Lys Gly Lys Ala
305                 310                 315                 320

Pro Ala Lys Pro Val Lys Pro Arg Pro Val Arg Gln Pro Ser
            325                 330                 335

Arg Ser Ser Met Ser Thr Pro Gly Pro Phe Ser Pro Ile Lys Arg
            340                 345                 350

Glu Pro Ser Thr Pro Gln Leu Ser Gln Ala Ser Ala Ser Ser Met Leu
        355                 360                 365

Pro Pro Asn Glu Arg Arg Thr Ser Val Ser Gln Arg Ser Gln Val Gly
        370                 375                 380

Ser Arg Pro Ser Arg Glu Gln Val Pro Ala Glu Ala Trp Glu Ser Phe
385                 390                 395                 400

Lys His Thr Ile Arg Lys Leu Tyr Leu Glu Glu Arg Lys Pro Leu Lys
                405                 410                 415

Glu Val Met Ser Val Met Ala Asp Gln Tyr Gly Phe Gln Ala Thr Pro
            420                 425                 430

Lys Met Tyr Lys Thr Arg Phe Ser Gln Trp Gly Phe Val Lys Asn Asn
        435                 440                 445

Thr Glu Glu Glu Val Lys Arg Leu Leu Ser Met Lys Phe Gln Arg Asp
    450                 455                 460

Ala Glu Gly Lys Val Ser Glu Phe Val Arg Asn Gly Lys Val Val Asn
465                 470                 475                 480

Leu Gly Thr Tyr Leu Lys Arg Lys Gly Val Thr Glu Tyr Asp Leu Val
                485                 490                 495

Asp Phe Glu Leu Pro Ala Asp Leu Pro Ala His Ile Arg Cys Arg Thr
            500                 505                 510

Pro Thr Pro Pro Pro Ala Pro Gly Tyr Leu Gln Ser Pro Asp Leu Leu
        515                 520                 525

Arg Ala Gln Glu Ile Ile Ile Ser Asn Met Arg Lys Ala Phe Leu Gln
        530                 535                 540

Cys Arg Gln Phe Glu Val Glu Thr Asp Ala Gln Val Gly Trp Gln Thr
545                 550                 555                 560

Ile Met Val Trp Gly Ala Gly Ser Ser Asp Leu Leu Leu Glu Ala Asn
                565                 570                 575

His Tyr Phe Glu Met Lys Asp His Asp Gln Gly Gly His Phe Leu Met
            580                 585                 590

Lys Ala Phe Gln Gln Leu Glu Ser Asp Leu Lys Lys Leu Ser Pro Gln
        595                 600                 605

Gly Ile Lys Glu Leu Leu Leu Gly Met Val His Arg Asp Pro Gly Met
        610                 615                 620

Met Thr Ala Leu Cys Lys Tyr Leu Ala Ala Tyr Ser Thr Thr Asn Phe
625                 630                 635                 640

Glu Arg Ser His Pro Leu Arg Gln Ile Phe Ser Cys Leu Tyr Glu Val
                645                 650                 655

Gln Gln Lys His Gly Pro Gly Thr Leu Ser Glu Leu Leu Trp Gly Ser
```

```
                   660                 665                 670
Ile Pro Thr Ile Ala Glu Glu Leu Glu Ala Ile Tyr Gly Arg Lys His
            675                 680                 685

Pro Tyr Val Ala Arg Thr Trp Val Asp Leu Ala Met Phe Tyr Asn His
        690                 695                 700

Val Asn Gln Glu Arg Leu Glu Lys Leu Val Gly Glu Leu Arg Leu Leu
705                 710                 715                 720

Gln Arg Gln Met Glu Gln Arg Leu Gly Pro Glu Ser Val Asp Val Leu
                725                 730                 735

Val Leu Arg Tyr Thr Ile Val Gln Leu Met Phe Ala Ala His Pro Gln
            740                 745                 750

Ser Asp Ala Thr Lys Gln Ala Thr Ile Asp Leu Trp His His Met Arg
        755                 760                 765

Gly Met Gly Leu Leu Phe Pro Ile Arg Ser Gln Gln Pro Asn Met Phe
    770                 775                 780

Cys Tyr His Ser Pro Val Lys Val Asp Pro Trp Thr Lys Arg Cys Arg
785                 790                 795                 800

Arg Arg Tyr Asp Ser Gly Val Gln Phe Leu Glu Glu His Val Gly Val
                805                 810                 815

Arg Val Val Val Tyr Phe Glu Glu Asp Phe His Thr Thr Glu His Ala
            820                 825                 830

Pro Glu His Ile Pro His Gln Gln His Gln Arg Gln His Gln Gln Ser
        835                 840                 845

His Gln Tyr Gln His Arg Gln Ser Gln Gln Gln Gln Arg Pro Gln Gln
    850                 855                 860

Leu Gln Ala Gln Asp Ser Trp Ala Ala Ala Met Glu Gln His Met Ser
865                 870                 875                 880

Ser Ser Lys Tyr Ser Phe Ile
                885

<210> SEQ ID NO 23
<211> LENGTH: 882
<212> TYPE: PRT
<213> ORGANISM: Gibberella fujikori

<400> SEQUENCE: 23

Met Phe Asn His Ser Ala Gly Gly Pro Arg Pro Ser Asp Asn Asn Glu
1               5                   10                  15

Asp Pro Ser Tyr Gly Phe Ala Asp Gln Gly Trp His Arg Phe Thr Met
            20                  25                  30

Asn Asn Asn Asn Thr Asn Ser Phe Ser Thr Gly Asn Ser Gln Ser Tyr
        35                  40                  45

His Asp Gly Gly Ala Ser Tyr Gly Asp Ser Ser Met Asp Trp Ala
    50                  55                  60

Pro Thr Pro Ser Ala Glu Tyr Asp Leu Arg Phe Asp Gln His Asp Pro
65                  70                  75                  80

Ile Ser Gln Asp Val Glu Leu Asp Asn Met Ser Ser His Gly Gly
                85                  90                  95

Gly Gly Gly Val Gly Arg Leu Val Ala His Phe Glu Asn Lys Ser Phe
            100                 105                 110

Ala Pro Pro Leu Pro Pro Arg Pro Ser Asn Val Val Thr Ser Pro Val
        115                 120                 125

His Gln Glu Pro Pro Val Ser Ser Pro Phe Gly Asn Phe Ser Val Thr
    130                 135                 140
```

```
Ser Pro Ile Val Thr Ser Pro Leu Ala Ser Pro Ala Glu Pro Asn Tyr
145                 150                 155                 160

Gly Leu Leu Ser Gly His Ser Arg Val Thr Ser Pro Ile Val Ser Pro
            165                 170                 175

Pro Pro Ala Leu Ala Phe Gly Gly Phe His Asp Ile Pro Val His Ser
        180                 185                 190

Pro Gly Val Gly Ser Pro Ser Gly Pro Phe Gly Ser Met Asn Ser Phe
    195                 200                 205

Met Val Asn Asn Asn Arg Val Thr Thr Pro Met Glu Thr Ala Ser Met
    210                 215                 220

Ala Gly Pro Ser Met Met Pro Asn Ser Asn Met Asn Ala Lys Ile Thr
225                 230                 235                 240

Ser Pro Gly Pro Val Thr Pro Gly Val Pro Gly Thr Pro Gly Phe Ala
            245                 250                 255

Ile Trp Arg Pro Pro Val Pro Met Thr Ser Lys Pro Ser Leu Asp Gln
            260                 265                 270

Pro Gln Gly Ser Ser Thr Ser Ser Asn Ser Gly Tyr Phe Ala Lys Pro
        275                 280                 285

Pro Ile Pro Ser Thr Pro Lys Pro Val Met Asn Ala Gly Ser Gln Leu
    290                 295                 300

Val Leu Asp Phe Asn Thr Asn Ser Thr Phe Asn Ala Lys Gly Lys Ala
305                 310                 315                 320

Pro Ala Lys Pro Pro Val Lys Pro Pro Arg Pro Val Arg Gln Pro Ser
            325                 330                 335

Arg Ser Ser Met Ser Thr Pro Gly Pro Phe Ser Pro Pro Ile Lys Gln
            340                 345                 350

Glu Pro Ser Thr Pro Gln Leu Ser Gln Ala Ser Thr Ser Ser Met Leu
        355                 360                 365

Pro Pro Asn Glu Arg Arg Thr Ser Val Ser Gln Arg Ser Gln Ala Gly
    370                 375                 380

Ser Arg Pro Ser Arg Glu Gln Val Pro Ala Glu Ala Trp Glu Ser Phe
385                 390                 395                 400

Lys His Thr Ile Arg Lys Leu Tyr Leu Glu Glu Arg Lys Pro Leu Lys
            405                 410                 415

Glu Val Met Ser Val Met Ala Asp Gln Tyr Gly Phe Gln Ala Thr Pro
            420                 425                 430

Lys Met Tyr Lys Thr Arg Phe Ser Gln Trp Gly Phe Val Lys Asn Asn
        435                 440                 445

Thr Glu Glu Val Lys Arg Leu Leu Ser Met Lys Phe Gln Arg Asp
    450                 455                 460

Ala Glu Gly Lys Val Ser Glu Phe Val Arg Asn Gly Lys Val Val Asn
465                 470                 475                 480

Leu Gly Thr Tyr Leu Lys Arg Lys Gly Val Thr Glu Tyr Asp Leu Val
            485                 490                 495

Asp Phe Glu Leu Pro Ala Asp Leu Pro Ala His Ile Arg Cys Arg Thr
        500                 505                 510

Pro Thr Pro Pro Pro Thr Pro Gly Tyr Leu Gln Ser Pro Asp Leu Leu
    515                 520                 525

Arg Ala Gln Glu Ile Ile Ser Asn Met Arg Lys Ala Phe Leu Gln
    530                 535                 540

Cys Arg Gln Phe Glu Val Glu Thr Asp Ala Gln Ile Gly Trp Gln Thr
545                 550                 555                 560

Ile Met Val Trp Gly Ala Gly Ser Ser Asp Leu Leu Leu Glu Ala Asn
```

-continued

```
                565                 570                 575

His Tyr Phe Glu Met Lys Asp His Asp Gln Gly Gly His Phe Leu Met
            580                 585                 590

Lys Ala Phe Gln Gln Leu Glu Ser Asp Leu Lys Lys Leu Ser Pro Gln
        595                 600                 605

Gly Ile Lys Glu Leu Leu Leu Gly Met Val His Arg Asp Pro Gly Met
    610                 615                 620

Met Thr Ala Leu Cys Lys Tyr Leu Ala Ala Tyr Ser Thr Thr Asn Phe
625                 630                 635                 640

Glu Arg Ser His Pro Leu Arg Gln Ile Phe Ser Cys Leu Tyr Glu Val
                645                 650                 655

Gln Gln Lys His Gly Pro Gly Thr Leu Ser Glu Leu Leu Trp Gly Ser
            660                 665                 670

Ile Pro Thr Ile Ala Glu Glu Leu Glu Ala Ile Tyr Gly Arg Lys His
        675                 680                 685

Pro Tyr Val Ala Arg Thr Trp Val Asp Leu Ala Met Phe Tyr Asn His
    690                 695                 700

Val Asn Gln Glu Arg Leu Glu Lys Leu Val Gly Glu Leu Arg Leu Leu
705                 710                 715                 720

Gln Arg Gln Met Glu Gln Arg Leu Gly Pro Glu Ser Val Asp Val Leu
                725                 730                 735

Val Leu Arg Tyr Thr Ile Val Gln Leu Met Phe Ala Ala His Pro Gln
            740                 745                 750

Ala Asp Ala Thr Lys Gln Ala Thr Ile Asp Leu Trp His His Leu Arg
        755                 760                 765

Gly Met Gly Leu Leu Phe Pro Ile Arg Ser Gln Gln Pro Asn Met Phe
    770                 775                 780

Cys Tyr His Ser Pro Val Lys Val Asp Pro Trp Thr Lys Arg Cys Arg
785                 790                 795                 800

Arg Arg Tyr Asp Ser Gly Val Gln Phe Leu Glu Glu His Val Gly Val
                805                 810                 815

Arg Val Val Val Tyr Phe Glu Glu Asp Phe His Thr Thr Glu His Ala
            820                 825                 830

Pro Glu His Ile Pro His Gln His Gln Gln Arg Gln Gln Gln Tyr Gln
        835                 840                 845

His Arg Gln Pro Gln Gln Gln Arg Pro Gln Gln Leu Gln Ala Gln Asp
    850                 855                 860

Ser Trp Ala Ala Ala Met Gly Gln Gln Met Ser Ser Ser Lys Tyr Ser
865                 870                 875                 880

Phe Ile

<210> SEQ ID NO 24
<211> LENGTH: 845
<212> TYPE: PRT
<213> ORGANISM: Stratchybortus chartarum

<400> SEQUENCE: 24

Met Phe Asn His Pro Met Gly Lys Thr Arg Ala Ser Gln Tyr Asn Asp
1               5                   10                  15

Asp Gln Phe Ala Tyr Ala Gln Gln Gln Trp Ala Asn Gln Pro Ala Ala
            20                  25                  30

Ala Ser Ser Ser Ser Ser Ser Ala Arg His Pro Pro Gln Leu Ser Gln
        35                  40                  45

Val Ser Asp Arg Ser Phe Leu Gly Asn Ala Gln Gly Gly Gly Gly Gly
```

-continued

```
                50                  55                  60
Met Asp Trp Ala Pro Ala Ser Asp Met Gln Met Gln Phe His His Asp
65                  70                  75                  80

Glu Pro His Ala Thr Thr Pro Ser Asp His His Ile Gln Phe Gln Gly
                85                  90                  95

Leu Asp Gln Asp Ser Ala Gly Gly Val Gly Arg Leu Val Ala His
            100                 105                 110

Phe Glu Asn Lys Ser Phe Gln Pro Pro Leu Pro Pro Arg Pro Leu Gln
            115                 120                 125

Asn Thr Gln Thr His Asn His Val Ala Val Ser Pro Pro Thr Ser Leu
130                 135                 140

Pro Tyr Gly Gly Tyr Leu Asn Ser Thr Ser Ile Asp Arg Val Gln Ser
145                 150                 155                 160

Pro Met Glu Ser Ser Tyr Gly Ser Phe Asp Leu His Gln Ser Arg Val
                165                 170                 175

Ala Ser Pro Ile Ala Ser Ser Pro Pro Met Ser Phe Gly Ser Phe
            180                 185                 190

His Asp Ala Ser Arg Val Pro Ser Pro Val Ala Thr Ser Ser Ser Ala
            195                 200                 205

His Phe Gly Ser Leu Asp Asp Phe Met Ser Ser Asn Arg Val Thr Thr
210                 215                 220

Pro Met Val Ala Ser Pro Met Val Thr Ser Pro Val Ser Ala Ser Pro
225                 230                 235                 240

Met Val Met Asn Pro Ser His Gly Thr Gln Gly Val Pro Gly Thr Pro
                245                 250                 255

Gly Phe Glu Ile Trp Arg Pro Pro Gly Ala Ile Pro Gln Ser Asn His
            260                 265                 270

Ser His Phe Asp Asn His Glu Thr Lys Pro Asn Ile Asn Ser Gly Phe
            275                 280                 285

Leu Lys Pro Pro Val Pro Ser Thr Pro Lys Pro Val Met Asn Ala Gly
            290                 295                 300

Ser Gln Phe Ile Leu Glu Leu Asn Pro Asn Ser Lys Gly Lys Gly Lys
305                 310                 315                 320

Ala Val Ala Lys Pro Thr Lys Pro Arg Val Pro Pro Ile Pro Pro
                325                 330                 335

Pro Ser Ser Lys Pro Pro Gly Leu Lys Gln Glu Pro Glu Asp Leu
            340                 345                 350

Leu Ile Pro Asp Leu Pro Ser Ser Thr Pro Ile Asn Pro Gln Gln Gln
            355                 360                 365

Ser Pro Thr Pro Leu Arg Pro Ser Ala Ser Arg Pro Ser Arg Glu Gln
370                 375                 380

Val Pro Ala Glu Ala Trp Glu Gln Phe Lys Thr Thr Ile Arg Ser Leu
385                 390                 395                 400

Tyr Leu Glu Glu Arg Lys Pro Leu Lys Glu Val Met Ser Ile Met Ala
                405                 410                 415

Asp Lys Tyr Gly Phe Gln Ala Thr Pro Lys Met Tyr Lys Thr Arg Phe
            420                 425                 430

Ser Gln Trp Gly Phe Val Lys Asn Asn Thr Glu Asp Glu Val Lys Arg
            435                 440                 445

Leu Leu Ser Met Lys Phe Gln Arg Asp Ala Glu Gly Lys Val Ser Glu
            450                 455                 460

Phe Val Arg Asn Gly Arg Val Val Asn Leu Gly Thr Tyr Leu Lys Arg
465                 470                 475                 480
```

Lys Gly Val Thr Glu Tyr Asp Leu Val Asp Phe Glu Leu Pro Ala Asp
            485                 490                 495

Leu Pro Ala His Ile Arg Cys Arg Thr Pro Thr Pro Pro Ala Pro
        500                 505                 510

Asp Tyr Leu Lys Ser Pro Asp Leu Leu Arg Ala Gln Glu Leu Val Val
            515                 520                 525

Val Asn Met Arg Lys Ala Phe Leu His Cys Arg Gln Phe Glu Ile Asp
530                 535                 540

Thr Asp Thr His Val Gly Trp Ser Ser Asn Met Val Trp Gly Ala Thr
545                 550                 555                 560

Ser Ser Asp Leu Leu Leu Glu Ala Asn Phe Tyr Phe Glu Ala Arg Asp
            565                 570                 575

Thr Asp Gln Gly Gly Ile Phe Leu Met Arg Ala Phe Lys Gln Leu Glu
            580                 585                 590

Leu Asp Leu Lys Asn Leu Ser Ser Pro Gly Ile Thr Glu Leu Leu Leu
            595                 600                 605

Gly Met Val Asn Arg Asp Pro Gly Leu Met Thr Ala Leu Cys Lys Tyr
            610                 615                 620

Leu Ala Ala Tyr Ser Thr Thr Asn Leu Glu Arg Ala His Pro Leu Arg
625                 630                 635                 640

Leu Ile Phe Thr Cys Leu Tyr Glu Val Gln Gln Lys His Gly Ser Met
            645                 650                 655

Thr Leu Ser Asp Leu Leu Trp Ser Ser Val Pro Thr Ile Ala Glu Glu
            660                 665                 670

Leu Glu Ala Ile Tyr Gly Arg Arg His Pro His Val Ala Arg Leu Trp
            675                 680                 685

Leu Asp Leu Ala Leu Phe Tyr Ser His Ser Ser Pro Glu Arg Met Glu
            690                 695                 700

Lys Leu Val Pro Glu Leu Arg Ile Val Leu Arg Gln Val Asp Gln Glu
705                 710                 715                 720

Gln Gly Gln Gln Thr Val Glu Ala Met Ser Leu Arg Tyr Ala Ile Ala
            725                 730                 735

Gln Leu Leu His Thr Ala Asp Pro Glu Ser Glu Ala Val Lys Gln Ala
            740                 745                 750

Ser Ile Glu Leu Tyr Asn His Ala Lys Ser Phe Gly Leu Ile Phe Pro
            755                 760                 765

Val Arg Gly Arg Pro Asn Ala Val Cys Tyr His Ser Pro Leu Lys Leu
770                 775                 780

Asp Pro Trp Thr Lys Arg Cys Arg Arg Tyr Asp Thr Ala Ser Phe
785                 790                 795                 800

Leu Leu Glu Lys His Val Gly Ile Arg Ala Asn Met Tyr Phe Glu Glu
            805                 810                 815

Asp His His Leu Val Glu His Ala Pro Asp Pro Gln Glu Ala Trp Ala
            820                 825                 830

Ala Ala Met Gln Gln Met Gly Thr Arg Trp Gly Tyr Ile
            835                 840                 845

<210> SEQ ID NO 25
<211> LENGTH: 935
<212> TYPE: PRT
<213> ORGANISM: Claviceps purpurea

<400> SEQUENCE: 25

```
Met Phe Asn Phe Ser Pro Gly Lys Pro Thr Ala Ser Ala Phe Asn Pro
```

-continued

```
1               5                   10                  15
Asp Leu Tyr Gly Arg Ala Ser Trp Pro Ser Phe Asp Ile Gly Asp Asp
                20                  25                  30
Gly Ala Ser Ser Leu Asp Ser Pro Ala Glu His Asn His Gly Gly Arg
                35                  40                  45
Leu Ala Ser His His Gly Gly Met Asp Trp Thr Gln Thr Ser Ser
     50                  55                  60
Gly Ala Gln Asn Asp Gly Tyr His Asn Asn Gln Arg His Ser Asn
 65                  70                  75                  80
Gln Gly Gly Thr Asp Ser Glu Leu Glu Ala Leu Leu His Arg Pro His
                85                  90                  95
Arg Gly Glu Arg Gly Ile Glu Val Gly Arg Leu Ala Ala His Phe Glu
                100                 105                 110
Asn Lys Gly Tyr Asp Pro Phe Glu Gln Lys Ser Ser Val Pro Thr Arg
                115                 120                 125
Leu Pro Ser Arg Pro Ile Tyr Thr Ala Val Ser Asn Ile Ser Ser Phe
     130                 135                 140
Asn Cys Gln Gln His Gln His Ser Leu Asp Leu Glu Cys Ser Ser Val
145                 150                 155                 160
Gly Met Asn Ser Phe Arg Ser Asn Ile Gly Phe Asp Pro Met Pro Leu
                165                 170                 175
Cys Gly Ser Ser Gly Ala Ala Ser Pro Ile Thr Ile Thr Asp Glu
                180                 185                 190
Ser Trp Gly Ser Phe Asp Ser Met Gln Arg Val Thr Ser Pro Val Ser
     195                 200                 205
Ile Ser Pro Pro Pro Trp Ser Tyr Gly Ser Phe Gln Glu His Arg Leu
     210                 215                 220
Ala Ser Pro Ile Ala Met Ser Ser Ser Ala Gln Phe Gly Ser Leu Asp
225                 230                 235                 240
Asn Phe Met Ala Asp Asn Arg Ile Arg Ser Ser Val Ala Gln Ser Pro
                245                 250                 255
Met Ser Asn Ser His Ser Val Ser Ser Pro Thr Ile Leu Ser Ala Ile
                260                 265                 270
Asn Ser Thr Ser Val Ser His Ala Ala Pro Ala Val Gly Gly Thr Pro
     275                 280                 285
Gly Phe Asp Thr Trp Tyr Pro Pro Gly Thr Ile Ser Ala Arg Ile Asn
     290                 295                 300
Gln Ser Pro Pro Asp Gly Phe Asn Thr Asn Arg Asn Gly Asp Ser Gly
305                 310                 315                 320
Ser Asn Asn Thr Thr Ala Ser Ile Thr Gly Ile Ser Asp Phe His Asn
                325                 330                 335
Ser Gly Asn Arg Val Ser Asp Arg Asp Ile Asp Leu Leu Ala Thr Pro
                340                 345                 350
Phe His Pro Glu Asn Asn Asn His Asp Ser Ala Ala Met Ser Ala Cys
                355                 360                 365
Ser Leu Lys Pro Pro Ala Ser Lys Pro Pro Asn Thr Asn Ile Ser Val
     370                 375                 380
Asp Asp Gln Gln Phe Met Leu Glu Met Ser Pro Cys Ala Ile Val Lys
385                 390                 395                 400
Gly Lys Met Pro Ala Arg Pro His Arg Gln Lys Ala Ser Leu Pro Ser
                405                 410                 415
Leu Asn Thr Ser Ser Leu Ala Pro Gln Val Lys Arg Glu Pro Ala Thr
     420                 425                 430
```

-continued

Pro Lys Pro Phe Asp Ile Pro Leu Ala Ser Ser Ala Pro Glu Ser Ser
        435                 440                 445

Phe Phe Met Leu Asp Arg Lys Pro Gly Ser Ile Ala Leu Arg Ser Gln
    450                 455                 460

Thr Gly Ile Arg Pro Arg Glu Gln Val Pro Ala Glu Ala Trp Glu
465                 470                 475                 480

Gln Phe Lys Gly Thr Ile Arg Thr Leu Tyr Leu Glu Glu Arg Lys Pro
                485                 490                 495

Leu Lys Glu Val Met Ser Ile Met Ala Glu Arg Phe Gly Phe Gln Ala
                500                 505                 510

Thr Pro Lys Met Tyr Lys Thr Arg Phe Ser Gln Trp Gly Phe Val Lys
        515                 520                 525

Asn Asn Thr Glu Glu Val Lys Arg Leu Leu Ser Lys Lys Phe Gln
    530                 535                 540

Arg Asp Ala Glu Gly Lys Ile Ser Glu Phe Val Arg Asn Gly Arg Val
545                 550                 555                 560

Val Asn Leu Gly Thr Tyr Leu Lys Arg Lys Gly Val Thr Glu Tyr Asp
                565                 570                 575

Leu Val Asp Phe Glu Leu Ser Ala Asp Leu Pro Ala His Val Arg Cys
            580                 585                 590

Arg Thr Pro Thr Pro Pro Thr Pro Gly Tyr Leu Arg Ser Pro Asp
595                 600                 605

Leu Leu Arg Ala Gln Glu Leu Ile Ile Gly Asn Met Arg Lys Thr Phe
    610                 615                 620

Leu His Cys Arg Gln Cys Glu Val Glu Ala Asp Val Arg Ile Gly Trp
625                 630                 635                 640

Pro Val Ile Met Ala Trp Gly Ala Gly Ser Ser Asp Leu Leu Leu Glu
                645                 650                 655

Ala Asn Val Tyr Phe Glu Ala Arg Asp Ala Glu Lys Gly Gly Ser Phe
                660                 665                 670

Leu Val Lys Ala Phe Thr Gln Leu Glu Gln Asp Leu Lys Gln Leu Ser
            675                 680                 685

Pro Leu Gly Ile Met Glu Leu Leu Leu Gly Met Val His Arg Asp Pro
        690                 695                 700

Gly Met Met Thr Ala Leu Cys Lys Tyr Leu Ala Ala Tyr Ser Thr Thr
705                 710                 715                 720

Asn Phe Glu Arg Ser His Pro Leu Arg Gln Ile Phe Thr Cys Leu Tyr
                725                 730                 735

Asp Val Gln Gln Lys His Gly Ala Ser Thr Val Ser Glu Leu Leu Trp
            740                 745                 750

Gly Gly Ile Pro Thr Ile Ala Glu Glu Leu Glu Ala Ile Tyr Ser Arg
        755                 760                 765

Arg His Pro Tyr Val Ala Arg Thr Trp Ile Asp Leu Ala Leu Phe Tyr
770                 775                 780

Asn Tyr Val Asn Ala Asp Arg Phe Asp Lys Leu Val Pro Glu Leu Arg
785                 790                 795                 800

Leu Gln Gln Arg Gln Val Glu Ala Arg Phe Gly Ser Asn Ser Pro Asp
                805                 810                 815

Ala Leu Thr Leu Arg Tyr Ala Ile Thr Gln Ser Leu Tyr Ala Ala Ser
            820                 825                 830

Pro His Ser Glu Ala Thr Arg His Ala Ala His Glu Met Trp Asn Gln
        835                 840                 845

```
Leu Thr Ser Val Gly Val Val Phe Gly Ile Arg Asp Ala Lys Pro Asn
            850                 855                 860
Ser Tyr Cys Tyr His Ser Pro Val Lys Val Asn Pro Arg Thr Lys Arg
865                 870                 875                 880
Cys Arg Arg Arg Tyr Asp Ser Gly Val Ser Ile Leu Glu Glu His Val
                885                 890                 895
Gly Val Arg Ile Gln Pro Tyr Phe Ala Glu Asp His His Cys Val
            900                 905                 910
His Ile Ser Asp Ala Gln Glu Thr Trp Ser Ala Ala Phe Asp Tyr Val
            915                 920                 925
Gly Ser Gly Lys Phe Val Phe
            930             935
```

<210> SEQ ID NO 26
<211> LENGTH: 865
<212> TYPE: PRT
<213> ORGANISM: Ophiocordyceps sinensis

<400> SEQUENCE: 26

```
Met Phe Asn His Pro Thr Ser Arg Pro His Ala Ser Ala Phe Ala Asn
1               5                   10                  15
Asp Ser Tyr Ala Phe Pro Pro Gln Pro Trp Ala Arg Phe Asp Val Asn
                20                  25                  30
Gln Ala Val Ser Ser Ser Gly Asp Ala Ser Gln Ser His His Ala Ala
            35                  40                  45
Leu Glu Ser Phe Asn Ala Ser Ser Asp Met Asp Trp Thr Pro Ser Ser
    50                  55                  60
Ser Ser Phe His His Gly Gly Thr Asp Val Glu Leu Ser Ser Leu Ser
65                  70                  75                  80
Pro Val Gln His Gln Asp Gly Gly Val Gly Arg Leu Val Ala His
                85                  90                  95
Phe Glu Asn Lys Gly Phe Ala Pro Phe Glu Asn Lys Gly Tyr Ala Pro
            100                 105                 110
Pro Leu Pro Pro Arg Pro Ala Pro Gly Ala Gln Thr Gln Gln Ser Val
            115                 120                 125
Pro Arg Ala Gln Phe Asp Gly Leu Gly Tyr Phe Gly Asn Gly Pro Gly
            130                 135                 140
Leu Ala Ser Ser Phe Asn Pro Asn Arg Ile Ala Thr Pro Ala Gln Ser
145                 150                 155                 160
Pro Ala Glu Ala Gln Trp Glu Asn Phe Gly Leu Gln Ser Pro Met Thr
                165                 170                 175
Ser Pro Val Ala Asn Ser Ser Phe Arg Leu Gln Asp Ala Ser Arg Gly
            180                 185                 190
Asp Asn Ser Gly Ala Gly Gln Leu Thr Gly Gln Phe Gly Cys Leu Asp
            195                 200                 205
His Phe Val Ser Ala Asn Arg Leu Gln Ser Gln Thr Glu Pro Ser Leu
            210                 215                 220
Ser Leu Ser Gln Arg Gly His Ser Ser Met Val Ser Pro Ala Val
225                 230                 235                 240
Val Ser Arg Ala Gln Pro Ser Pro Pro Thr Ser Gly Thr Pro Gly Phe
                245                 250                 255
Asp Ile Trp Arg Pro Pro Gly Ser Val Ser Val Lys Ser Glu Ala Pro
            260                 265                 270
Pro Leu Ala Cys Ser Val Leu Pro Ala Gly Ser Tyr Gly Lys Pro Pro
            275                 280                 285
```

```
Val Pro Asn Thr Pro Lys Pro Asn Leu Asn Ala Pro Gly Ser His Phe
    290                 295                 300
Ile Leu Glu Phe Asn Pro Ser Ala Arg Ala Lys Gly Lys Ala Pro Ala
305                 310                 315                 320
Lys Pro Ala Arg Leu Arg Ala Pro Pro Pro Ser Met Pro Ser Pro
                325                 330                 335
Phe Ser Pro Glu Ile Lys Lys Glu Pro Ala Thr Pro Ser Arg Ser Ser
            340                 345                 350
Pro Ser Ile Ala Ala Leu Pro Val Ser Ser Thr Ser Phe Arg His Arg
        355                 360                 365
Asp Ala Asn Trp Thr Pro Ser Tyr Ser Gln Lys Gln Ala Gln Arg Gln
    370                 375                 380
Pro Ser Val Ser Leu Arg Ala His Ala Ala Gly Ser Arg Pro Ser Arg
385                 390                 395                 400
Glu Gln Val Pro Ala Glu Ala Trp Gly Gln Phe Lys Ser Thr Ile Arg
                405                 410                 415
Ala Leu Tyr Leu Asp Glu Arg Arg Pro Leu Lys Glu Val Met Asn Val
            420                 425                 430
Met Ala Glu Lys Tyr Lys Phe Gln Ala Thr Pro Lys Met Tyr Lys Thr
        435                 440                 445
Arg Phe Ser Gln Trp Gly Phe Val Lys Asn Asn Thr Glu Asp Glu Val
    450                 455                 460
Lys Arg Leu Leu Ser Met Lys Phe Gln Arg Asp Ala Glu Gly Lys Val
465                 470                 475                 480
Ser Glu Phe Val Arg Asn Gly Arg Val Val Asn Leu Gly Thr Tyr Leu
                485                 490                 495
Lys Arg Lys Gly Val Thr Glu Tyr Asp Leu Ile Asp Phe Glu Leu Pro
            500                 505                 510
Ala Asp Leu Pro Ala His Val Lys Cys Arg Thr Pro Thr Pro Pro
        515                 520                 525
Ala Pro Glu Tyr Leu Arg Ser Pro Asp Leu Val Arg Ala Gln Glu Leu
    530                 535                 540
Val Val Gly Asn Met Arg Lys Ala Phe Leu His Cys Arg Gln Val Glu
545                 550                 555                 560
Val Glu Thr Asn Thr Gln Val Gly Trp Ala Ser Thr Met Val Trp Gly
                565                 570                 575
Ala Gly Ser Ser Asp Leu Leu Met Glu Ala Asn Phe Tyr Phe Glu Ala
            580                 585                 590
Arg Asp Ala Asp Gln Gly His Phe Leu Met Arg Ala Phe Lys Gln
        595                 600                 605
Leu Glu Val Asp Leu Arg Lys Leu Ser Pro Leu Gly Ile Lys Glu Leu
    610                 615                 620
Leu Leu Gly Met Val Gln Arg Asp Pro Gly Met Met Thr Ala Leu Cys
625                 630                 635                 640
Lys Tyr Leu Ala Ala Tyr Ser Thr Thr Asn Leu Glu Arg Ser His Pro
                645                 650                 655
Leu Arg Gln Ile Phe Thr Cys Leu Tyr Glu Val Gln Gln Lys His Gly
            660                 665                 670
Pro Gly Thr Leu Ser Asp Leu Leu Trp Gly Ser Ile Pro Ala Ile Ala
        675                 680                 685
Glu Glu Leu Glu Ala Ile Tyr Gly Arg Arg His Pro Tyr Val Ala Arg
    690                 695                 700
```

```
Ala Trp Ile Asp Leu Ala Leu Phe Tyr Asn His Val His Pro Glu Arg
705                 710                 715                 720

Leu Ala Lys Leu Ile Gly Glu Leu Arg Gly Leu Glu Arg Gln Leu Glu
            725                 730                 735

Gln Arg His Gly Ala Ser Ser Val Glu Met Leu Ser Leu Arg Tyr Ser
        740                 745                 750

Ile Leu Gln Leu Leu Tyr Ala Ala Gly Pro Gln Ala Asp Ser Thr Arg
    755                 760                 765

Gln Ala Ala Val Ala Leu Trp Asn His Val Arg Ser Leu Gly Val Val
770                 775                 780

Phe Ser Val Arg Asp Ala Lys Pro Asn Val Tyr Cys Tyr His Ser Pro
785                 790                 795                 800

Leu Lys Val Asp Pro Trp Thr Lys Arg Cys Arg Arg Tyr Asp Ser
                805                 810                 815

Gly Val Ala Ile Met Glu Glu His Val Gly Val Lys Val Leu Pro Tyr
                820                 825                 830

Phe Glu Glu Asp Phe His Thr Val His Ala Pro Asp Cys Gln Glu
            835                 840                 845

Ala Trp Ser Ala Ala Leu Asn His Met Gln Ser Ala Lys Trp Ala Tyr
    850                 855                 860

Ile
865

<210> SEQ ID NO 27
<211> LENGTH: 1355
<212> TYPE: PRT
<213> ORGANISM: Nectria haematococca

<400> SEQUENCE: 27

Met Gly Trp His Met Leu Ile Arg Pro Pro Ala Val Ser Gly Leu Glu
1               5                   10                  15

Leu Val Ala Tyr Gly Gln Cys Pro Trp Ala Ser Val Cys Ser Gly Pro
            20                  25                  30

Ile Ala Leu Phe Glu Arg Gln Phe Ser Ala Ser Ser Gln Pro Gln Val
        35                  40                  45

Lys Pro Lys Asp Thr Trp Thr Ile Gly Glu Ser Arg Leu Gly Tyr Arg
    50                  55                  60

Ala Gly Gln Arg Ser Gln Glu Arg Ala Gly Ser His Lys Thr Pro Thr
65                  70                  75                  80

Trp Leu Cys Pro Phe Cys Asp Pro Ala Ala Glu Leu Leu Gly Ser Cys
                85                  90                  95

Ser Leu Val Asn Val Met Leu Thr Trp Glu Glu Glu Ala Leu Leu Leu
            100                 105                 110

Arg Lys Ser Arg Leu Lys Leu His Lys Gln Pro Thr Pro Leu Thr Asp
        115                 120                 125

His Gly Arg Gln Asp Leu Gly Val Ala Ser Glu Thr Ala Gly Arg Gln
    130                 135                 140

Ser Val Ala Ala Pro Arg Pro Asn Ala Ser Gln Ala Ala Gly Asp Gln
145                 150                 155                 160

Arg Arg Pro Thr Glu Phe Leu Ser Pro Asn Pro Met Ala Ile Pro Ser
                165                 170                 175

Pro Val Asp Asp Ala Met Pro Cys Arg Val Leu Ser Cys Asn Ala Met
            180                 185                 190

Pro Trp Leu Gln Lys Pro Val Ser Ser Asn His Pro Leu Ser Gly His
        195                 200                 205
```

```
Gln Cys Pro Ala Tyr Ala Cys Pro Val Cys Leu Phe Leu Ser Ala Thr
    210             215                 220
Gly Ala Ala Phe Gly Cys Ile Gly Ser Arg Val Leu Gly Ser Ser Val
225                 230                 235                 240
Ala Leu Thr Ala Asn Ala Pro Lys Asp Gly Thr Ser Gln Arg Glu Val
                245                 250                 255
Phe Trp Lys Ile Val Glu Thr Ile Leu Ser Ala Phe Trp Arg Arg Ala
            260                 265                 270
Leu Val Leu Val Cys Ser Leu Leu Ala Ala Thr Lys Thr Leu Ala Gly
        275                 280                 285
Met Gln Met Gln Ala Arg Pro Leu Gly Arg Phe Pro Cys Ser Pro Asp
    290                 295                 300
Gly Ser Arg Gly Cys Ser Leu Leu Val Met Ile Gly Ala Ser Arg Arg
305                 310                 315                 320
Gly Trp Trp Leu Arg Gln Ile His Leu Leu Leu Gln Ala Thr Trp Ser
                325                 330                 335
His Ala Leu Thr Ser Pro Pro Leu Lys Ala Val Leu Ser Leu Ala Gln
            340                 345                 350
Leu Glu Ser Arg Pro Ser Thr Pro Trp Met Ala Leu Pro Cys Cys Leu
        355                 360                 365
Gly Asn Asp Asn Val Ser Lys Pro Trp Pro Phe Ser Leu Ala Val Thr
370                 375                 380
Val Leu Pro Ser Pro Gln Arg Ala Asn Pro Pro Ser Pro Val Pro Ala
385                 390                 395                 400
Gln Ser Thr Pro Gln Pro Glu Pro Arg Pro Ala Leu Cys Leu Ser Leu
                405                 410                 415
Leu Ala Leu Gly Val Gly Ala Gly Pro Ala Ala Leu Leu Leu Leu
            420                 425                 430
Ala Arg Ser Cys Trp Leu Leu Ala Gly Ala Pro Arg Leu Ser Thr Arg
        435                 440                 445
Leu Ser Pro Ser Leu Thr Ala Leu Glu Pro Ala Val Arg Ala Ser Leu
    450                 455                 460
Val Arg Pro Ala Arg Leu Gln Ala Asn Met Phe Asn Gln Pro Ser Gly
465                 470                 475                 480
Gly Pro Arg Ala Ser Asp Ser Asn Gly Gln Pro Ser Tyr Gly Phe Thr
                485                 490                 495
Asp Gln Ala Trp Pro Arg Tyr Gly Leu Ala Asn Asn Ser Ala Ser Phe
            500                 505                 510
Ser Thr Asp His Ser Gln Ser Ile Tyr Ala Ser Asp Arg Gln Tyr Gly
        515                 520                 525
Asp Ser Ser Gly Met Asp Trp Ala Pro Thr Pro Thr Asp Tyr Gln Thr
    530                 535                 540
Arg Phe Gln His Gln Asp Ala Ile Thr Glu Asn Val Glu Leu Asp Asn
545                 550                 555                 560
Met Ser Pro Gln Ala Gly Gly Val Gly Arg Leu Val Ala His Phe
                565                 570                 575
Glu Asn Lys Gly Phe Ala Pro Pro Leu Pro Arg Pro Ser Asn Thr
            580                 585                 590
Ile Ser Ser Pro Val Asn Gln Glu Pro Ser Val Ser Ser Pro Phe Gly
        595                 600                 605
Thr Phe Ser Val Ala Ser Pro Ile Leu Thr Ser Pro Leu Ala Ser Pro
    610                 615                 620
```

-continued

Ser Glu Pro Asn Tyr Gly Leu Leu Gly Asp Gln Ser Arg Val Ala Ser
625                 630                 635                 640

Pro Ile Ala Ser Pro Pro Ile Ala Phe Gly Gly Tyr His Asp Met
    645                 650                 655

Ser Val Ser Ser Pro Gly Val Gly Ser Ser Gly His Phe Gly Ser
    660                 665                 670

Met Asn Ser Phe Met Val Asn Asn Arg Val Ala Thr Pro Met Glu Thr
    675                 680                 685

Thr Met Ala Ala Ser Pro Met Val Ala Ala Ser Met Met Asn Asn Pro
    690                 695                 700

Lys Val Ala Ser Pro Ser Pro Ala Ala Pro Gly Val Pro Gly Thr Pro
705                 710                 715                 720

Gly Phe Ala Ile Trp Arg Pro Val Pro Met Thr Pro Lys Pro Thr
                725                 730                 735

Met Asp Gln Phe Gln Gly Thr Ser Ser Ser Thr Ser Gly Gly Tyr
            740                 745                 750

Phe Ala Lys Pro Pro Ile Pro Ser Thr Pro Lys Pro Val Met Asn Ala
                755                 760                 765

Gly Ser Gln Leu Val Leu Asp Phe Asn Ser Asn Ser Gly Ser Ile Ala
770                 775                 780

Lys Gly Lys Ala Pro Met Arg Pro Pro Ala Lys Pro Arg His Pro Val
785                 790                 795                 800

Arg Gln Pro Ser Arg Ser Gln Ile Ser Thr Pro Ala Ala Phe Ser Pro
                805                 810                 815

Ala Ile Lys Arg Glu Pro Ser Thr Pro His Leu Ser Gln Ala Ser Pro
        820                 825                 830

Ala Pro His Thr Leu Ala Ser Glu Arg Arg Ser Ser Val Ser Gln Arg
            835                 840                 845

Ser Gln Thr Gly Ser Arg Pro Ser Arg Glu Gln Val Pro Ala Glu Ala
    850                 855                 860

Trp Glu Ser Phe Lys Asn Thr Ile Arg Thr Leu Tyr Leu Asp Glu Arg
865                 870                 875                 880

Lys Pro Leu Lys Glu Val Met Ser Ile Met Ala Asp Lys Tyr Gly Phe
                885                 890                 895

Gln Ala Thr Pro Lys Met Tyr Lys Thr Arg Phe Ser Gln Trp Gly Phe
            900                 905                 910

Val Lys Asn Asn Thr Glu Glu Glu Val Lys Arg Leu Leu Ser Lys Lys
        915                 920                 925

Phe Gln Arg Asp Ala Glu Gly Lys Val Ser Phe Val Arg Asn Gly
    930                 935                 940

Lys Val Val Asn Leu Gly Thr Tyr Leu Lys Arg Lys Gly Val Thr Glu
945                 950                 955                 960

Tyr Asp Leu Ile Asp Phe Glu Leu Pro Ala Glu Leu Pro Ala His Ile
                965                 970                 975

Arg Cys Arg Thr Pro Thr Pro Pro Ala Pro Gly Tyr Leu Gln Ser
            980                 985                 990

Pro Asp Leu Leu Arg Ala Gln Glu Thr Ile Ile Ser Asn Met Arg Lys
    995                 1000                1005

Ala Phe Leu Gln Cys Arg Gln Phe Glu Val Glu Thr Asp Ala Gln
        1010                1015                1020

Val Gly Trp Gln Thr Ile Met Val Trp Gly Ala Gly Ser Ser Asp
        1025                1030                1035

Leu Leu Leu Glu Ala Asn His Asn Phe Glu Arg Arg Asp Thr Asp

```
    1040                1045                1050

Gln Gly  Gly His Phe Leu Met  Lys Ala Phe Lys Gln  Leu Glu Val
    1055                1060                1065

Asp Leu  Lys Lys Leu Ser Pro  Gln Gly Ile Gln Glu  Leu Leu Leu
    1070                1075                1080

Gly Met  Val Arg Arg Asp Pro  Gly Met Met Thr Ala  Leu Cys Lys
    1085                1090                1095

Tyr Leu  Ala Ala Tyr Ser Thr  Thr Asn Phe Glu Arg  Ser His Pro
    1100                1105                1110

Leu Arg  Gln Ile Phe Ala Cys  Leu Tyr Glu Val Gln  Gln Lys His
    1115                1120                1125

Gly Pro  Gly Thr Leu Ser Asp  Leu Leu Trp Ala Ser  Ile Pro Thr
    1130                1135                1140

Ile Ala  Glu Glu Leu Glu Ala  Ile Tyr Gly Arg Lys  His Pro Tyr
    1145                1150                1155

Val Ala  Arg Thr Trp Thr Asp  Leu Ala Thr Phe Tyr  Asn His Ala
    1160                1165                1170

Asn Pro  Glu Arg Leu Glu Lys  Leu Val Ala Glu Leu  Arg Leu Leu
    1175                1180                1185

Gln Arg  Gln Met Glu His Arg  Gln Gly Ala Asn Ser  Val Glu Val
    1190                1195                1200

Phe Val  Leu Arg Tyr Thr Ile  Val Gln Leu Met Val  Ala Ala His
    1205                1210                1215

Pro Gln  Ser Asp Ala Thr Lys  Gln Thr Thr Ile Asp  Leu Trp His
    1220                1225                1230

His Ala  Arg Gly Met Gly Leu  Ile Phe Pro Val Arg  Gly Gln Gln
    1235                1240                1245

Pro Asn  Val Phe Cys Tyr His  Ser Pro Val Lys Val  Asp Pro Trp
    1250                1255                1260

Thr Lys  Arg Cys Arg Arg Arg  Tyr Asp Ser Gly Val  Arg Leu Leu
    1265                1270                1275

Glu Glu  His Val Gly Val Gln  Val Ile Pro Tyr Phe  Glu Glu Asp
    1280                1285                1290

Phe His  Thr Thr Glu His Ala  Pro Glu His Met Pro  Gln Gln Gln
    1295                1300                1305

Gln Gln  Gln Gln His His His  His Gln Gln Gln Gln  Gln Gln Gln
    1310                1315                1320

Gln Gln  Gln Gln Gln Arg Ala  Pro Gln Leu Gln Ala  Gln Asp Ser
    1325                1330                1335

Trp Ala  Ala Ala Met Glu Gln  Gln Met Gly Gly Asn  Lys Trp Ser
    1340                1345                1350

Phe Ile
    1355

<210> SEQ ID NO 28
<211> LENGTH: 928
<212> TYPE: PRT
<213> ORGANISM: Metarhizium acridum

<400> SEQUENCE: 28

Met Phe Asn Leu Pro Pro Asp Lys Ser Arg Ala Ser Asp Phe Asn Thr
1               5                   10                  15

Asp Ser Tyr Gly Leu Asn Asn Gln Gly Trp Pro Ala Phe Asp Phe Gly
            20                  25                  30
```

```
Gln Gly Ala Pro Ser Ser Ser Gly Leu Ala Pro Glu His Asn His Asp
             35                  40                  45

Ala Arg Gln Ser Phe Ser His Val Gly Gly Met Glu Trp Ala Pro Thr
 50                  55                  60

Pro Ser Asp Val Gln Pro Asn Tyr Thr His Gly His His Glu His Gln
 65                  70                  75                  80

Asp His Gln Gly Asp Thr Ala Met Glu Leu Glu Ala Leu Ser Ser Pro
                 85                  90                  95

Gln Thr Gly Gly Gly Val Gly Arg Leu Val Ala His Phe Glu Asn Lys
                100                 105                 110

Gly Phe Asn Pro Phe Glu Asn Lys Ser Phe Glu Pro Ala Pro Pro Leu
            115                 120                 125

Pro Pro Arg Pro Val Asn Thr Ser Val Asn Asn Gln Thr His His
            130                 135                 140

Gln Ala His Gln Gln Ser Val Gln Asn Pro Ser Ile Ser Met Asn Ser
145                 150                 155                 160

Phe Gln Ala Ser Leu Ser Phe Asp Pro Leu Ser Tyr Cys Gly Asn Gly
                165                 170                 175

Ile Ser Gly Thr Ala Ser Ser Val Phe Asn Pro Asn Arg Ile Thr Asn
            180                 185                 190

Pro Val Thr Gly Thr Gly Gln Ser Trp Gly Ser Phe Thr Ser Leu Glu
            195                 200                 205

Arg Val Thr Gly Pro Met Ala Ala Ser Pro Pro Ala Met Ser Tyr Asn
            210                 215                 220

Ser Phe Gln Asp Asn Arg Val Thr Ser Pro Gly Leu Gly Ser Ser Ser
225                 230                 235                 240

Ala His Phe Gly Asn Leu Asp Asp Phe Met Ser Asp Asn Arg Ile His
                245                 250                 255

Ser Pro Met Ala His Ser Pro Met Pro Asn Ser His Leu Ala Ser Ser
            260                 265                 270

Pro Met Val Ala Ser Pro Met Thr Gln Ser Leu Ser Asn Ser Asn Ala
            275                 280                 285

Ala Pro Val Gly Gly Thr Pro Gly Phe Glu Ile Trp Arg Pro Pro Gly
            290                 295                 300

Thr Thr Ala Ser Thr Thr Thr Lys Met Asn Gln Ser Gln Pro Asn Asn
305                 310                 315                 320

Phe Thr Thr Pro Leu Ser Ala Thr Asn Thr Phe Met Asn Pro Ser Gly
                325                 330                 335

Ser His Ser Thr Ala Thr Ser Thr Asn Arg Asn Ser Ile Gly Gly
            340                 345                 350

Arg Asn Ser Thr Asn Ser Ala Gly Phe Leu Lys Pro Val Pro Thr
            355                 360                 365

Thr Pro Lys Pro Asn Val Ser Ile Gly Asn Gln Phe Ile Leu Glu Leu
            370                 375                 380

Ile Pro Ser Ala Lys Ala Lys Gly Lys Ala Pro Ala Lys Pro Pro Arg
385                 390                 395                 400

Pro Arg Val Pro Pro Val Pro Ser Ser Phe Ala Ala Glu Ile Lys
                405                 410                 415

Gln Glu Pro Met Thr Pro Thr Pro Ser Glu Ile Pro Leu Ala Ser Ser
                420                 425                 430

Thr Pro Thr Pro Leu Thr Pro Ser Thr Thr Leu Ser Asp Gln Lys Pro
                435                 440                 445

Gly Ser Leu Ser Leu Arg Gly Gln Ala Gly Thr Arg Pro Ser Arg Glu
```

-continued

```
                450             455             460
Gln Val Pro Ala Glu Ala Trp Glu Gln Phe Lys Gly Thr Ile Arg Ser
465                 470                 475                 480

Leu Tyr Leu Glu Asp Arg Lys Pro Leu Lys Glu Val Met Ala Ile Met
                485                 490                 495

Ala Glu Lys Tyr Asn Phe Gln Ala Thr Pro Lys Met Tyr Lys Thr Arg
            500                 505                 510

Phe Ser Gln Trp Gly Phe Val Lys Asn Asn Thr Glu Glu Val Lys
        515                 520                 525

Lys Leu Leu Ser Met Lys Phe Gln Arg Asp Ala Glu Gly Lys Val Ser
    530                 535                 540

Glu Phe Val Arg Asn Gly Arg Val Val Asn Leu Gly Thr Tyr Leu Lys
545                 550                 555                 560

Arg Lys Gly Val Thr Glu Tyr Asp Leu Val Asp Phe Glu Leu Ser Ala
                565                 570                 575

Asp Leu Pro Ala His Val Arg Cys Arg Thr Pro Thr Pro Pro Ala
            580                 585                 590

Pro Gly Tyr Leu Arg Ser Pro Asp Leu Leu Arg Ala Gln Glu Leu Val
        595                 600                 605

Val Gly Asn Met Arg Lys Ala Phe Leu His Cys Arg Gln Phe Glu Val
    610                 615                 620

Glu Thr Asp Ala Arg Ile Gly Trp Pro Ile Thr Met Val Trp Gly Ala
625                 630                 635                 640

Gly Ser Ser Asp Leu Leu Leu Glu Ala Asn Phe Tyr Phe Glu Ala Arg
                645                 650                 655

Asp Ala Asp Gln Gly Gly Asp Phe Leu Met Lys Ala Phe Lys Gln Leu
            660                 665                 670

Glu Leu Asp Leu Lys Lys Leu Ser Pro Leu Gly Ile Asn Glu Leu Leu
        675                 680                 685

Leu Gly Met Val His Arg Asp Pro Gly Met Met Thr Ala Leu Cys Lys
    690                 695                 700

Tyr Leu Ala Ala Tyr Ser Ser Thr Asn Phe Glu Arg Ser His Pro Leu
705                 710                 715                 720

Arg Gln Ile Phe Ala Cys Leu Tyr Glu Val Gln Gln Lys His Gly Ser
                725                 730                 735

Ala Thr Val Ser Glu Leu Leu Trp Gly Ser Met Pro Thr Ile Ala Glu
            740                 745                 750

Glu Leu Glu Ala Ile Tyr Ser Arg Arg His Pro Tyr Val Ala Arg Thr
        755                 760                 765

Trp Ile Asp Leu Ala Leu Phe His Asn His Val Asn Ala Asp Arg Leu
    770                 775                 780

Asp Lys Leu Ala Ser Glu Leu Arg Leu Gln Arg Gln Val Glu Gln
785                 790                 795                 800

Arg Tyr Gly Thr Asn Ser Thr Asp Ala Leu Thr Leu Arg Tyr Ser Ile
                805                 810                 815

Leu Gln Leu Leu Tyr Val Val Asn Ser Gln Ser Asp Leu Thr Arg His
            820                 825                 830

Ala Ala His Asp Leu Trp Asn His Leu Lys Ser Met Gly Val Val Phe
        835                 840                 845

Gly Leu Arg Asp Ala Lys Pro Asn Val Phe Cys Tyr His Ser Pro Val
    850                 855                 860

Lys Val Asp Pro Trp Thr Lys Arg Cys Arg Arg Arg Tyr Asp Ser Gly
865                 870                 875                 880
```

-continued

```
Val Ala Ile Leu Glu Glu His Val Gly Val Arg Val Gln Pro Tyr Phe
                885                 890                 895

Glu Glu Asp Phe His His Ala Val His Ala Pro Asp Ala Gln Glu Ala
            900                 905                 910

Trp Ser Ser Ala Leu Gly His Met Ser Ser Gly Lys Tyr Ser Phe Ile
        915                 920                 925

<210> SEQ ID NO 29
<211> LENGTH: 947
<212> TYPE: PRT
<213> ORGANISM: Villosiclava virens

<400> SEQUENCE: 29

Met Phe Asn Leu Pro Pro Asp Lys Gln Arg Asn Pro Gly Phe His Ala
1               5                   10                  15

Asp Ser Tyr Gly Phe Asn Gly Gln Pro Trp Ser Arg Phe Asp Phe Gly
            20                  25                  30

Gln Ala Thr Met Ser Ser Ser Ser Gly Phe Ser Ala Glu Gln Ala His
        35                  40                  45

Asp Glu Arg Gln Asp Phe Gly Gly Met Gly Gly Met Glu Trp Ala Pro
    50                  55                  60

Thr Pro Ser Ser Val Gln Pro Asp Tyr Tyr Gln Gly His Gln Gln His
65                  70                  75                  80

Pro Gly Asp Thr Asp Met Glu Leu Glu Ala Leu Ser Ser Pro His Ser
                85                  90                  95

Gly Gly Gly Val Gly Arg Leu Val Ala His Phe Glu Asn Lys Gly Phe
            100                 105                 110

Asn Pro Phe Glu Asn Arg Ser Leu Ala Ser Ala Pro Pro Leu Pro Pro
        115                 120                 125

Arg Pro Leu Asn Ala Thr Val Ser Met Asn Asn His Thr Asp Gly Asn
    130                 135                 140

Asp Gln Arg His His His His His Gln Gln Gln Gln Gln Gln His Ala
145                 150                 155                 160

Ala Gln Ser Pro Ser Ile Ser Met Asn Ser Phe Gln Ala Ser Leu Ser
                165                 170                 175

Phe Asp Pro Leu Ser Ser Tyr Cys Gly Asn Gly Val Ser Gly Gly Gly
            180                 185                 190

Gly Gly Ser Ser Pro Ser Phe Asp Ser Asn Arg Ile Ala Ser Pro Val
        195                 200                 205

Thr Ala Ser Gly Glu Ser Trp Gly Gly Pro Phe Pro Ser Ser His Arg
    210                 215                 220

Val Thr Ser Pro Ala Ala Met Ser Pro Thr Cys Met Ala Phe Gly Ser
225                 230                 235                 240

Tyr His Asp Gly Arg Val Ala Ser Pro Gly Ala Gly Pro Ser Pro Ala
                245                 250                 255

Pro Phe Gly Ser Leu Asp Gly Phe Met Pro Gly Asn Arg Met Arg Ser
            260                 265                 270

Pro Val Ala His Gln Pro Asp Met Ala Ser Ser Pro Leu Val Pro Ser
        275                 280                 285

Pro Val Thr Pro Asn Ser Ala Ala His Gln Asn Thr Pro Ala Ile Gly
    290                 295                 300

Gly Thr Pro Gly Phe Glu Ile Trp Arg Pro Pro Gly Ser Ala Asp Thr
305                 310                 315                 320

Lys Ser Leu Asn Arg Asn Leu Ser Asn Ala Leu Gly Ser Ser Ala Asn
```

-continued

```
                325                 330                 335
Pro Ser Ile Ala Gly Phe Arg Ser Ser Ser Arg Arg Gly Thr Ser
                340                 345                 350
Ser Asn Gly Ala Ile Pro Asn His Ala Thr Thr Ser Pro Ala Ala Ser
                355                 360                 365
Asn Asn Asn His Val Ser Ala Thr Asn Ser Ala Gly Phe Leu Lys Pro
            370                 375                 380
Pro Val Pro Thr Thr Pro Lys Pro His Ile Ser Val Gly Asn Gln Phe
385                 390                 395                 400
Ile Leu Glu Leu Asn Pro Ile Thr Lys Ala Lys Ser Arg Ala Ser Thr
                405                 410                 415
Lys Pro Pro Arg Pro Arg Val Pro Pro Ile Pro Leu Pro Phe Val
                420                 425                 430
Pro Glu Ile Lys Gln Glu Pro Glu Thr Pro Arg Pro Leu Glu Met Thr
                435                 440                 445
Pro Ser Cys Pro Ala Glu Val Asn Gly Leu Ser Cys Pro Phe Pro Asp
                450                 455                 460
Gln Lys Pro Ala Ser Ala Ser Leu Arg Gly Gln Ile Gly Thr Arg Pro
465                 470                 475                 480
Ser Arg Glu Gln Val Pro Ala Glu Ala Trp Glu His Phe Lys Gly Ile
                485                 490                 495
Ile Arg Ala Leu Tyr Leu Glu Glu Arg Lys Pro Leu Lys Glu Val Met
                500                 505                 510
Ala Ile Met Ala Asp Lys Tyr Ser Phe Gln Ala Thr Pro Lys Met Tyr
                515                 520                 525
Lys Thr Arg Phe Ser Gln Trp Gly Phe Val Lys Asn Asn Thr Glu Glu
                530                 535                 540
Glu Val Lys Arg Leu Leu Ser Met Lys Phe Gln Arg Asp Ala Glu Gly
545                 550                 555                 560
Lys Val Ser Glu Phe Val Arg Asn Gly Arg Val Val Asn Leu Gly Thr
                565                 570                 575
Tyr Leu Lys Arg Lys Gly Val Thr Glu Tyr Asp Leu Val Asp Phe Glu
                580                 585                 590
Leu Pro Ala Asp Leu Pro Ala His Val Arg Cys Arg Thr Pro Thr Pro
                595                 600                 605
Pro Pro Ala Pro Gly Tyr Leu Arg Ser Pro Asp Leu Leu Arg Ala Gln
                610                 615                 620
Glu Leu Val Val Ser Asn Met Arg Lys Ala Phe Leu His Cys Arg Gln
625                 630                 635                 640
Phe Glu Asp Glu Thr Glu Ala Arg Ile Gly Trp Pro Val Thr Met Val
                645                 650                 655
Trp Gly Ala Gly Ser Ser Glu Leu Leu Leu Glu Ala Asn Phe Tyr Phe
                660                 665                 670
Glu Ala Gln Asp Ala Thr Gln Gly Gly Asn Leu Leu Ile His Ala Phe
                675                 680                 685
Gln Gln Leu Glu Val Asp Leu Lys Lys Leu Thr Pro Leu Gly Ile Asn
            690                 695                 700
Glu Leu Leu Leu Gly Met Val His Arg Asp Pro Gly Met Met Thr Ala
705                 710                 715                 720
Leu Cys Lys Tyr Leu Ala Ala Tyr Ser Thr Thr Asn Phe Glu Arg Ser
                725                 730                 735
His Pro Leu Arg Gln Ile Phe Thr Cys Leu Tyr Glu Ile Gln Gln Lys
                740                 745                 750
```

-continued

```
His Gly Ser Met Thr Val Ser Glu Leu Leu Trp Gly Ser Met Pro Ala
            755                 760                 765
Ile Ala Glu Glu Leu Glu Thr Ile Tyr Gln Arg His His Pro Tyr Val
770                 775                 780
Ala Arg Thr Trp Ile Asp Leu Ala Leu Phe Tyr Asn His Val Asn Val
785                 790                 795                 800
Glu Gln Phe Asp Lys Leu Val Ser Glu Leu Arg Leu Gln Gln His Gln
                805                 810                 815
Val Glu Gln Arg Tyr Gly Leu Ser Ser Ala Asp Ala Leu Ala Leu Arg
            820                 825                 830
Tyr Ala Ile Leu Gln Ser Leu Tyr Ala Ala Asn Pro Arg Ser Glu Ala
                835                 840                 845
Val Arg Gln Ala Ala His Asp Thr Trp Asn His Met Arg Arg Ala Asn
850                 855                 860
Val Val Phe Gly Leu Arg Asp Ala Lys Ala Asn Val Tyr Cys Tyr His
865                 870                 875                 880
Cys Pro Val Lys Val Asp Pro Trp Thr Lys Arg Cys Arg Arg Arg Tyr
                885                 890                 895
Asp Ser Gly Val Ala Ile Leu Glu Gln His Val Gly Val Lys Ile Gln
            900                 905                 910
Pro Tyr Phe Glu Glu Asp Phe His His Ala Val His Val Pro Asp Ala
                915                 920                 925
Gln Glu Ala Trp Ser Ser Ala Leu Asp His Met Gly Ser Gly Lys Tyr
930                 935                 940
Ala Phe Ile
945

<210> SEQ ID NO 30
<211> LENGTH: 1025
<212> TYPE: PRT
<213> ORGANISM: Acremonium chrysogenum

<400> SEQUENCE: 30

Met Phe Asn Gln Arg Gln Trp Asp Glu Leu His Ala Phe Thr Ala Ser
1               5                   10                  15
Phe Ala Ala Gly Pro Asn Ser Asn Ile Ser Asn Glu Pro Pro Pro Ser
            20                  25                  30
Gln Leu His Gln Gln Val Gln Leu Pro Pro Gln Gln Asp Gln Gln Phe
        35                  40                  45
Gln His Pro Ala Asn Pro Asp Asn Pro His Val Leu His Gln Gln His
    50                  55                  60
Gln Gln Pro Pro Pro Gln Phe Phe Gln Gln Gly Ala Gln His Gln
65                  70                  75                  80
His Gln Gln His Gln Gln Asp Gln Ser Phe Gln Tyr Ala Phe Ser
                85                  90                  95
Ser Gln Gln Glu Trp Ala Arg Phe Asp Phe Asn Pro Ser Ser Ala Pro
            100                 105                 110
Ala Asn Thr Ser Gln Pro Val His His Gly Gly Ala Ser Asp Phe
        115                 120                 125
Gly Ala Ala Pro Ser Gly Asp Met Asp Trp Thr Pro Ser Ala Asp Phe
    130                 135                 140
Ser Ser Ser Phe Pro Pro Cys Leu Asp Gly Gly Leu Gln Ser Gly Ser
145                 150                 155                 160
Gln Ala Val Ala Ala Gly Ile Lys Val Glu Pro Asp Ser Leu Asn Gln
```

-continued

```
                165                 170                 175
Asn Tyr Gln Ala Gln Gly Val Gly Asp Gly Gly Gly Thr Thr Gly
                180                 185                 190
Val Gly Arg Leu Ile Ala Gln Phe Glu Asn Lys Gly Tyr Gln Pro Pro
            195                 200                 205
Leu Pro Pro Arg Pro Thr Asp Asn Ala Val Thr Ser Asn Ser Val Thr
210                 215                 220
Ser Pro Ile Pro Ile Asn Gln His Gln Pro Ser Thr His Ser Thr His
225                 230                 235                 240
Phe Asn Ala Thr Pro Gln Gly Thr Ser Phe Thr Asn Asn Ser Phe Asn
                245                 250                 255
Ser His Ser Phe Ala Ser Asn Gly Ile Thr Thr Ser Ser Asp Ser Asn
            260                 265                 270
Phe Gly Ser Tyr Ser Ala Ser His Arg Pro Pro Ala Ser Pro Ile Ala
        275                 280                 285
Thr Ser Pro Pro Pro Thr Ser Phe Gly Gly Phe His Asp Ala Pro Gly
    290                 295                 300
Val Thr Ser Pro Gly Thr Gly Pro Ser Asn Asp Pro Phe Gly Ser Leu
305                 310                 315                 320
Asn Ser Leu Val Arg Asn Asn Pro Met Glu His Ser Met Ala Thr Ser
                325                 330                 335
Pro Met Val Ser Ser Pro Ala Pro Thr Thr Pro Gly His Gly Ala Val
            340                 345                 350
Gly Thr Pro Gly Phe Ala Met Trp Arg Ala Pro Ser Gln Gln Gln Glu
        355                 360                 365
Gln Tyr Gln Gln Leu Ser Gln Pro Gln Pro Arg Ser Gln Pro Gln Ala
    370                 375                 380
His Pro Gln Gln His His His Gln Glu Phe Ser Gln Phe Gln Gln Gln
385                 390                 395                 400
Gln Ser His Gln Ser Gln Gln Ala Pro Glu Pro Met Gln His Gln Phe
                405                 410                 415
His Gln Gln Gln Gln His Phe His Gln Pro Gln Pro Leu Gln
            420                 425                 430
His Gln Gln Ala His His Gln Leu Pro Leu Arg Asn Pro Ser Phe Gly
        435                 440                 445
Gln Asn Asn Asn Val Thr Ser Pro Gly Gly Tyr Phe Arg Pro Asn
    450                 455                 460
Pro Pro Thr Pro Arg Pro Thr Thr Ala Leu Gly Asn Gln Phe Ile Leu
465                 470                 475                 480
Glu Leu Asn Pro Gly Ser Lys Ala Lys Gly Arg Ala Pro Ala Lys Pro
                485                 490                 495
Pro Lys Pro Lys Ala Pro Lys Pro Glu Phe Leu Ser Thr Thr Ser Ser
            500                 505                 510
Thr Ala Pro Phe Ser Pro Ser Ile Lys Gln Glu Pro Ser Thr Pro Gln
        515                 520                 525
Pro Ser Thr Gly Pro Ser Thr Thr Asp Gly Ala Pro Asp Ala Ser Thr
    530                 535                 540
Glu Ser Ile Thr Ser Arg Pro Thr Ile Leu Thr Arg Pro Ser Arg Glu
545                 550                 555                 560
Gln Val Pro Ala Glu Ala Trp Glu Gly Leu Lys Ser Thr Ile Arg Asp
                565                 570                 575
Leu Tyr Leu Glu Gln Arg Lys Pro Leu Lys Glu Val Met Ser Ile Met
            580                 585                 590
```

```
Ala Glu Lys Tyr Asn Phe Gln Ala Thr Pro Lys Met Tyr Lys Thr Arg
        595                 600                 605

Phe Ser Gln Trp Gly Phe Val Lys Asn Asn Thr Glu Asp Glu Val Lys
        610                 615                 620

Lys Leu Leu Ser Met Lys Phe Gln Arg Asp Ala Glu Gly Lys Val Ser
625                 630                 635                 640

Glu Phe Val Arg Asn Gly Lys Ile Val Asn Leu Gly Thr Tyr Leu Lys
                645                 650                 655

Arg Lys Gly Val Thr Glu Tyr Asp Leu Val Asp Phe Glu Leu Pro Ala
        660                 665                 670

Asn Leu Pro Ser His Ile Arg Cys Arg Thr Pro Thr Pro Pro Ala
        675                 680                 685

Pro Glu Tyr Leu Lys Ser Pro Asp Leu Met Arg Ala Gln Glu Leu Val
        690                 695                 700

Val Ser Asn Ile Arg Lys Ala Phe Leu Gln Cys Arg Gln Trp Glu Leu
705                 710                 715                 720

Glu Thr Glu Arg Glu Val Gly Trp Pro Ala Thr Met Val Trp Gly Ala
                725                 730                 735

Pro Ser Ser Glu Met Leu Thr Glu Ala Asn Phe Tyr Phe Glu Ala Gly
        740                 745                 750

Asp Val Asp Ser Gly Gly Gln Cys Leu Met Asn Ala Phe Asn Gln Leu
        755                 760                 765

Glu Ile Asp Leu Lys Gln Leu Ser Pro Gln Ala Ile Leu Glu Val Val
        770                 775                 780

Leu Gly Met Val Arg Arg Asp Pro Gly Leu Met Thr Ala Leu Cys Lys
785                 790                 795                 800

Tyr Val Ala Ala Phe Ser Thr Thr Asn Tyr Asp Arg Ser His Pro Leu
                805                 810                 815

Arg Gln Ile Phe Thr Cys Leu Tyr Asp Val Gln Gln Lys His Gly Ala
        820                 825                 830

Ala Thr Leu Ser Glu Leu Leu Trp Gly Ser Thr Pro Leu Val Ala Glu
        835                 840                 845

Glu Leu Glu Ala Ile Tyr Gly Arg Arg His Pro Tyr Val Ala Arg Thr
        850                 855                 860

Trp Val Asp Leu Ala Ile Phe Tyr Asp Gln Lys Gly Thr Glu Arg Leu
865                 870                 875                 880

Glu Lys Leu Ala Leu Glu Leu Arg Val Gln His Arg Gln Met Glu Asn
                885                 890                 895

Ser Gln Gly Thr Glu Phe Ser Asp Leu Leu Ala Leu Arg Tyr Ala Ile
        900                 905                 910

Ala Gln Leu Phe Tyr Ala Ala Asp Ala Glu Ser Ala Ser Thr Lys Gln
        915                 920                 925

Ala Ala Asp Glu Leu Leu Lys Asp Met Lys Lys Ala Lys Leu Leu Phe
        930                 935                 940

Arg Val Arg Asp Ser Arg Pro Asn Thr Tyr Cys Tyr His Cys Ala Val
945                 950                 955                 960

Lys Asn Asp Pro Trp Thr Lys Arg Cys Arg Arg Arg Tyr Asp Ser Val
                965                 970                 975

Val Glu Leu Leu Glu Lys His Thr Asp Val Lys Ile Gln Pro Tyr Phe
        980                 985                 990

Glu Glu Asp Phe His Thr Thr His  His Glu Leu Glu Ser  Gln Asp Ala
        995                 1000                1005
```

```
Trp Ala Ser Val Met Gly Gly Asn Thr Thr Gln Ser Arg Trp Gly
1010                1015                1020

Phe Leu
    1025
```